US008196796B2

(12) United States Patent
Shelton, IV et al.

(10) Patent No.: US 8,196,796 B2
(45) Date of Patent: *Jun. 12, 2012

(54) SHAFT BASED ROTARY DRIVE SYSTEM FOR SURGICAL INSTRUMENTS

(75) Inventors: Frederick E. Shelton, IV, Hillsboro, OH (US); Richard W. Timm, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/020,053

(22) Filed: Feb. 3, 2011

(65) Prior Publication Data

US 2011/0121051 A1 May 26, 2011

Related U.S. Application Data

(63) Continuation of application No. 11/810,015, filed on Jun. 4, 2007, now Pat. No. 7,905,380.

(51) Int. Cl.
*A61B 17/10* (2006.01)

(52) U.S. Cl. ............... 227/178.1; 227/175.1; 227/176.1; 227/180.1

(58) Field of Classification Search ............... 227/175.1, 227/176.1, 178.1, 180.1
See application file for complete search history.

(56) References Cited

U.S. PATENT DOCUMENTS

| 66,052 | A | 6/1867 | Smith |
| 2,037,727 | A | 4/1936 | La Chapelle |
| 2,214,870 | A | 9/1940 | West |
| 2,441,096 | A | 5/1948 | Happe |
| 2,526,902 | A | 10/1950 | Rublee |
| 2,804,848 | A | 9/1957 | O'Farrell et al. |
| 2,808,482 | A | 10/1957 | Zanichkowsky et al. |
| 2,853,074 | A | 9/1958 | Olson |
| 3,032,769 | A | 5/1962 | Palmer |
| 3,075,062 | A | 1/1963 | Iaccarino |
| 3,078,465 | A | 2/1963 | Bobrov |
| 3,266,494 | A | 8/1966 | Brownigg et al. |
| 3,269,630 | A | 8/1966 | Fleischer |

(Continued)

FOREIGN PATENT DOCUMENTS

CA 2458946 A1 3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Brian D Nash
*Assistant Examiner* — Michelle Lopez

(57) ABSTRACT

A surgical instrument including a drive mechanism configured to advance a staple driver and/or cutting member at a first rate and retract the staple driver and/or cutting member at a different rate. In at least one embodiment, the rate at which the driver and cutting member is advanced and/or retracted is the distance that the driver and/or cutting member is translated per actuation of a trigger, for example. In various embodiments, the cutting member can be retracted at a faster rate as compared to the rate in which it is advanced. In such embodiments, the surgical instrument can, owing to the slower advancing rate, provide a greater torque or advancing force to the cutting member while, owing to the faster retracting rate, reduce the time required for the surgeon to retract the cutting member.

19 Claims, 32 Drawing Sheets

U.S. PATENT DOCUMENTS

| | | |
|---|---|---|
| 3,357,296 A | 12/1967 | Lefever |
| 3,490,675 A | 1/1970 | Green et al. |
| 3,551,987 A | 1/1971 | Wilkinson |
| 3,598,943 A | 8/1971 | Barrett |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,751,902 A | 8/1973 | Kingsbury et al. |
| 3,819,100 A | 6/1974 | Noiles et al. |
| 3,821,919 A | 7/1974 | Knohl |
| 3,892,228 A | 7/1975 | Mitsui |
| 3,894,174 A | 7/1975 | Cartun |
| 3,940,844 A | 3/1976 | Colby et al. |
| 4,129,059 A | 12/1978 | Van Eck |
| 4,213,562 A | 7/1980 | Garrett et al. |
| 4,250,436 A | 2/1981 | Weissman |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,428,376 A | 1/1984 | Mericle |
| 4,429,695 A | 2/1984 | Green |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,475,679 A | 10/1984 | Fleury, Jr. |
| 4,485,816 A | 12/1984 | Krumme |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,548,202 A | 10/1985 | Duncan |
| 4,565,189 A | 1/1986 | Mabuchi |
| 4,566,620 A | 1/1986 | Green et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,664,305 A | 5/1987 | Blake, III et al. |
| 4,665,916 A | 5/1987 | Green |
| 4,667,674 A | 5/1987 | Korthoff et al. |
| 4,671,445 A | 6/1987 | Barker et al. |
| 4,676,245 A | 6/1987 | Fukuda |
| 4,693,248 A | 9/1987 | Failla |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,741,336 A | 5/1988 | Failla et al. |
| 4,752,024 A | 6/1988 | Green et al. |
| 4,754,909 A | 7/1988 | Barker et al. |
| 4,767,044 A | 8/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,892,244 A | 1/1990 | Fox et al. |
| 4,915,100 A | 4/1990 | Green |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,156,315 A | 10/1992 | Green et al. |
| 5,156,614 A | 10/1992 | Green et al. |
| 5,158,567 A | 10/1992 | Green |
| 5,163,598 A | 11/1992 | Peters et al. |
| 5,171,247 A | 12/1992 | Hughett et al. |
| 5,171,249 A | 12/1992 | Stefanchik et al. |
| 5,188,111 A | 2/1993 | Yates et al. |
| 5,190,517 A | 3/1993 | Zieve et al. |
| 5,195,968 A | 3/1993 | Lundquist et al. |
| 5,197,648 A | 3/1993 | Gingold |
| 5,200,280 A | 4/1993 | Karasa |
| 5,205,459 A | 4/1993 | Brinkerhoff et al. |
| 5,207,697 A | 5/1993 | Carusillo et al. |
| 5,211,649 A | 5/1993 | Kohler et al. |
| 5,217,457 A | 6/1993 | Delahuerga et al. |

| | | | | | |
|---|---|---|---|---|---|
| 5,217,478 A | 6/1993 | Rexroth | 5,405,072 A | 4/1995 | Zlock et al. |
| 5,219,111 A | 6/1993 | Bilotti et al. | 5,405,344 A | 4/1995 | Williamson et al. |
| 5,221,036 A | 6/1993 | Takase | 5,409,498 A | 4/1995 | Braddock et al. |
| 5,221,281 A | 6/1993 | Klicek | 5,411,508 A | 5/1995 | Bessler et al. |
| 5,222,963 A | 6/1993 | Brinkerhoff et al. | 5,413,267 A | 5/1995 | Solyntjes et al. |
| 5,222,975 A | 6/1993 | Crainich | 5,413,268 A | 5/1995 | Green et al. |
| 5,222,976 A | 6/1993 | Yoon | 5,413,272 A | 5/1995 | Green et al. |
| 5,223,675 A | 6/1993 | Taft | 5,415,334 A | 5/1995 | Williamson, IV et al. |
| 5,234,447 A | 8/1993 | Kaster et al. | 5,415,335 A | 5/1995 | Knodell, Jr. |
| 5,236,440 A | 8/1993 | Hlavacek | 5,417,361 A | 5/1995 | Williamson, IV |
| 5,240,163 A | 8/1993 | Stein et al. | 5,421,829 A | 6/1995 | Olichney et al. |
| 5,242,457 A | 9/1993 | Akopov et al. | 5,422,567 A | 6/1995 | Matsunaga |
| 5,244,462 A | 9/1993 | Delahuerga et al. | 5,423,809 A | 6/1995 | Klicek |
| 5,246,156 A | 9/1993 | Rothfuss et al. | 5,425,745 A | 6/1995 | Green et al. |
| 5,246,443 A | 9/1993 | Mai | 5,431,322 A | 7/1995 | Green et al. |
| 5,253,793 A | 10/1993 | Green et al. | 5,431,668 A | 7/1995 | Burbank, III et al. |
| 5,258,009 A | 11/1993 | Conners | 5,433,721 A | 7/1995 | Hooven et al. |
| 5,259,366 A | 11/1993 | Reydel et al. | 5,438,302 A | 8/1995 | Goble |
| 5,260,637 A | 11/1993 | Pizzi | 5,441,193 A | 8/1995 | Gravener |
| 5,263,629 A | 11/1993 | Trumbull et al. | 5,441,494 A | 8/1995 | Ortiz |
| 5,263,973 A | 11/1993 | Cook | 5,445,304 A | 8/1995 | Plyley et al. |
| 5,268,622 A | 12/1993 | Philipp | 5,445,644 A | 8/1995 | Pietrafitta et al. |
| 5,271,543 A | 12/1993 | Grant et al. | 5,447,417 A | 9/1995 | Kuhl et al. |
| 5,271,544 A | 12/1993 | Fox et al. | 5,447,513 A | 9/1995 | Davison et al. |
| RE34,519 E | 1/1994 | Fox et al. | 5,449,355 A | 9/1995 | Rhum et al. |
| 5,275,323 A | 1/1994 | Schulze et al. | 5,449,365 A | 9/1995 | Green et al. |
| 5,275,608 A | 1/1994 | Forman et al. | 5,452,836 A | 9/1995 | Huitema et al. |
| 5,281,216 A | 1/1994 | Klicek | 5,454,827 A | 10/1995 | Aust et al. |
| 5,282,806 A | 2/1994 | Haber et al. | 5,456,401 A | 10/1995 | Green et al. |
| 5,282,829 A | 2/1994 | Hermes | 5,458,579 A | 10/1995 | Chodorow et al. |
| 5,297,714 A | 3/1994 | Kramer | 5,462,215 A | 10/1995 | Viola et al. |
| 5,304,204 A | 4/1994 | Bregen | 5,465,894 A | 11/1995 | Clark et al. |
| 5,307,976 A | 5/1994 | Olson et al. | 5,465,895 A | 11/1995 | Knodel et al. |
| 5,309,927 A | 5/1994 | Welch | 5,465,896 A | 11/1995 | Allen et al. |
| 5,312,023 A | 5/1994 | Green et al. | 5,466,020 A | 11/1995 | Page et al. |
| 5,312,329 A | 5/1994 | Beaty et al. | 5,467,911 A | 11/1995 | Tsuruta et al. |
| 5,314,424 A | 5/1994 | Nicholas | 5,470,006 A | 11/1995 | Rodak |
| 5,318,221 A | 6/1994 | Green et al. | 5,470,007 A | 11/1995 | Plyley et al. |
| 5,330,502 A | 7/1994 | Hassler | 5,472,132 A | 12/1995 | Savage et al. |
| 5,332,142 A | 7/1994 | Robinson et al. | 5,472,442 A | 12/1995 | Klicek |
| 5,333,422 A | 8/1994 | Warren et al. | 5,473,204 A | 12/1995 | Temple |
| 5,334,183 A | 8/1994 | Wuchinich | 5,474,057 A | 12/1995 | Makower et al. |
| 5,339,799 A | 8/1994 | Kami et al. | 5,474,566 A | 12/1995 | Alesi et al. |
| 5,341,724 A | 8/1994 | Vatel | 5,476,206 A | 12/1995 | Green et al. |
| 5,342,395 A | 8/1994 | Jarrett et al. | 5,476,479 A | 12/1995 | Green et al. |
| 5,342,396 A | 8/1994 | Cook | 5,478,003 A | 12/1995 | Green et al. |
| 5,344,060 A | 9/1994 | Gravener et al. | 5,478,354 A | 12/1995 | Tovey et al. |
| 5,350,400 A | 9/1994 | Esposito et al. | 5,480,089 A | 1/1996 | Blewett |
| 5,352,235 A | 10/1994 | Koros et al. | 5,480,409 A | 1/1996 | Riza |
| 5,352,238 A | 10/1994 | Green et al. | 5,482,197 A | 1/1996 | Green et al. |
| 5,354,303 A | 10/1994 | Spaeth et al. | 5,484,095 A | 1/1996 | Green et al. |
| 5,356,006 A | 10/1994 | Alpern et al. | 5,484,398 A | 1/1996 | Stoddard |
| 5,358,510 A | 10/1994 | Luscombe et al. | 5,484,451 A | 1/1996 | Akopov et al. |
| 5,359,231 A | 10/1994 | Flowers et al. | 5,485,947 A | 1/1996 | Olson et al. |
| D352,780 S | 11/1994 | Glaeser et al. | 5,485,952 A | 1/1996 | Fontayne |
| 5,360,428 A | 11/1994 | Hutchinson, Jr. | 5,487,499 A | 1/1996 | Sorrentino et al. |
| 5,364,003 A | 11/1994 | Williamson, IV | 5,487,500 A | 1/1996 | Knodel et al. |
| 5,366,134 A | 11/1994 | Green et al. | 5,489,058 A | 2/1996 | Plyley et al. |
| 5,366,479 A | 11/1994 | McGarry et al. | 5,489,256 A | 2/1996 | Adair |
| 5,370,645 A | 12/1994 | Klicek et al. | 5,496,312 A | 3/1996 | Klicek |
| 5,372,596 A | 12/1994 | Klicek et al. | 5,496,317 A | 3/1996 | Goble et al. |
| 5,372,602 A | 12/1994 | Burke | 5,497,933 A | 3/1996 | DeFonzo et al. |
| 5,374,277 A | 12/1994 | Hassler | 5,503,320 A | 4/1996 | Webster et al. |
| 5,379,933 A | 1/1995 | Green et al. | 5,503,635 A | 4/1996 | Sauer et al. |
| 5,381,782 A | 1/1995 | DeLaRama et al. | 5,503,638 A | 4/1996 | Cooper et al. |
| 5,382,247 A | 1/1995 | Cimino et al. | 5,505,363 A | 4/1996 | Green et al. |
| 5,383,880 A | 1/1995 | Hooven | 5,509,596 A | 4/1996 | Green et al. |
| 5,383,881 A | 1/1995 | Green et al. | 5,509,916 A | 4/1996 | Taylor |
| 5,383,888 A | 1/1995 | Zvenyatsky et al. | 5,511,564 A | 4/1996 | Wilk |
| 5,383,895 A | 1/1995 | Holmes et al. | 5,514,129 A | 5/1996 | Smith |
| 5,389,098 A | 2/1995 | Tsuruta et al. | 5,514,157 A | 5/1996 | Nicholas et al. |
| 5,391,180 A | 2/1995 | Tovey et al. | 5,518,163 A | 5/1996 | Hooven |
| 5,392,979 A | 2/1995 | Green et al. | 5,518,164 A | 5/1996 | Hooven |
| 5,395,030 A | 3/1995 | Kuramoto et al. | 5,520,700 A | 5/1996 | Beyar et al. |
| 5,395,033 A | 3/1995 | Byrne et al. | 5,522,817 A | 6/1996 | Sander et al. |
| 5,395,312 A | 3/1995 | Desai | 5,527,320 A | 6/1996 | Carruthers et al. |
| 5,397,046 A | 3/1995 | Savage et al. | 5,529,235 A | 6/1996 | Boiarski et al. |
| 5,397,324 A | 3/1995 | Carroll et al. | D372,086 S | 7/1996 | Grasso et al. |
| 5,403,312 A | 4/1995 | Yates et al. | 5,531,744 A | 7/1996 | Nardella et al. |

| | | | | | |
|---|---|---|---|---|---|
| 5,533,521 A | 7/1996 | Granger | 5,647,526 A | 7/1997 | Green et al. |
| 5,533,581 A | 7/1996 | Barth et al. | 5,647,869 A | 7/1997 | Goble et al. |
| 5,533,661 A | 7/1996 | Main et al. | 5,649,937 A | 7/1997 | Bito et al. |
| 5,535,934 A | 7/1996 | Boiarski et al. | 5,651,491 A | 7/1997 | Heaton et al. |
| 5,535,935 A | 7/1996 | Vidal et al. | 5,653,373 A | 8/1997 | Green et al. |
| 5,535,937 A | 7/1996 | Boiarski et al. | 5,653,374 A | 8/1997 | Young et al. |
| 5,540,375 A | 7/1996 | Bolanos et al. | 5,653,677 A | 8/1997 | Okada et al. |
| 5,541,376 A | 7/1996 | Ladtkow et al. | 5,653,721 A | 8/1997 | Knodel et al. |
| 5,542,594 A | 8/1996 | McKean et al. | 5,655,698 A | 8/1997 | Yoon |
| 5,543,119 A | 8/1996 | Sutter et al. | 5,657,921 A | 8/1997 | Young et al. |
| 5,547,117 A | 8/1996 | Hamblin et al. | 5,658,281 A | 8/1997 | Heard |
| 5,549,628 A | 8/1996 | Cooper et al. | 5,658,300 A | 8/1997 | Bito et al. |
| 5,549,637 A | 8/1996 | Crainich | 5,662,258 A | 9/1997 | Knodel et al. |
| 5,553,675 A | 9/1996 | Pitzen et al. | 5,662,260 A | 9/1997 | Yoon |
| 5,553,765 A | 9/1996 | Knodel et al. | 5,662,662 A | 9/1997 | Bishop et al. |
| 5,554,169 A | 9/1996 | Green et al. | 5,667,517 A | 9/1997 | Hooven |
| 5,556,416 A | 9/1996 | Clark et al. | 5,667,527 A | 9/1997 | Cook |
| 5,558,665 A | 9/1996 | Kieturakis | 5,669,544 A | 9/1997 | Schulze et al. |
| 5,558,671 A | 9/1996 | Yates | 5,669,904 A | 9/1997 | Platt, Jr. et al. |
| 5,560,530 A | 10/1996 | Bolanos et al. | 5,669,907 A | 9/1997 | Platt, Jr. et al. |
| 5,560,532 A | 10/1996 | DeFonzo et al. | 5,669,918 A | 9/1997 | Balazs et al. |
| 5,562,239 A | 10/1996 | Boiarski et al. | 5,673,840 A | 10/1997 | Schulze et al. |
| 5,562,241 A | 10/1996 | Knodel et al. | 5,673,841 A | 10/1997 | Schulze et al. |
| 5,562,682 A | 10/1996 | Oberlin et al. | 5,673,842 A | 10/1997 | Bittner et al. |
| 5,562,701 A | 10/1996 | Huitema et al. | 5,678,748 A | 10/1997 | Plyley et al. |
| 5,562,702 A | 10/1996 | Huitema et al. | 5,680,981 A | 10/1997 | Mililli et al. |
| 5,564,615 A | 10/1996 | Bishop et al. | 5,680,982 A | 10/1997 | Schulze et al. |
| 5,571,090 A | 11/1996 | Sherts | 5,680,983 A | 10/1997 | Plyley et al. |
| 5,571,100 A | 11/1996 | Goble et al. | 5,683,349 A | 11/1997 | Makower et al. |
| 5,571,116 A | 11/1996 | Bolanos et al. | 5,685,474 A | 11/1997 | Seeber |
| 5,573,543 A | 11/1996 | Akopov et al. | 5,688,270 A | 11/1997 | Yates et al. |
| 5,574,431 A | 11/1996 | McKeown et al. | 5,690,269 A | 11/1997 | Bolanos et al. |
| 5,575,789 A | 11/1996 | Bell et al. | 5,692,668 A | 12/1997 | Schulze et al. |
| 5,575,799 A | 11/1996 | Bolanos et al. | 5,693,042 A | 12/1997 | Boiarski et al. |
| 5,575,803 A | 11/1996 | Cooper et al. | 5,693,051 A | 12/1997 | Schulze et al. |
| 5,577,654 A | 11/1996 | Bishop | 5,695,494 A | 12/1997 | Becker |
| 5,579,978 A | 12/1996 | Green et al. | 5,695,504 A | 12/1997 | Gifford, III et al. |
| 5,580,067 A | 12/1996 | Hamblin et al. | 5,697,543 A | 12/1997 | Burdorff |
| 5,582,611 A | 12/1996 | Tsuruta et al. | 5,697,943 A | 12/1997 | Sauer et al. |
| 5,582,617 A | 12/1996 | Klieman et al. | 5,700,270 A | 12/1997 | Peyser et al. |
| 5,584,425 A | 12/1996 | Savage et al. | 5,702,387 A | 12/1997 | Arts et al. |
| 5,586,711 A | 12/1996 | Plyley et al. | 5,702,408 A | 12/1997 | Wales et al. |
| 5,588,579 A | 12/1996 | Schnut et al. | 5,702,409 A | 12/1997 | Rayburn et al. |
| 5,588,580 A | 12/1996 | Paul et al. | 5,704,087 A | 1/1998 | Strub |
| 5,588,581 A | 12/1996 | Conlon et al. | 5,704,534 A | 1/1998 | Huitema et al. |
| 5,591,170 A | 1/1997 | Spievack et al. | 5,706,997 A | 1/1998 | Green et al. |
| 5,591,187 A | 1/1997 | Dekel | 5,706,998 A | 1/1998 | Plyley et al. |
| 5,597,107 A | 1/1997 | Knodel et al. | 5,707,392 A | 1/1998 | Kortenbach |
| 5,599,151 A | 2/1997 | Daum et al. | 5,709,334 A | 1/1998 | Sorrentino et al. |
| 5,599,344 A | 2/1997 | Paterson | 5,709,680 A | 1/1998 | Yates et al. |
| 5,599,350 A | 2/1997 | Schulze et al. | 5,711,472 A | 1/1998 | Bryan |
| 5,601,224 A | 2/1997 | Bishop et al. | 5,713,128 A | 2/1998 | Schrenk et al. |
| 5,603,443 A | 2/1997 | Clark et al. | 5,713,505 A | 2/1998 | Huitema |
| 5,605,272 A | 2/1997 | Witt et al. | 5,713,895 A | 2/1998 | Lontine et al. |
| 5,605,273 A | 2/1997 | Hamblin et al. | 5,715,987 A | 2/1998 | Kelley et al. |
| 5,607,094 A | 3/1997 | Clark et al. | 5,715,988 A | 2/1998 | Palmer |
| 5,607,095 A | 3/1997 | Smith et al. | 5,716,366 A | 2/1998 | Yates |
| 5,607,450 A | 3/1997 | Zvenyatsky et al. | 5,718,359 A | 2/1998 | Palmer et al. |
| 5,609,285 A | 3/1997 | Grant et al. | 5,718,360 A | 2/1998 | Green et al. |
| 5,611,709 A | 3/1997 | McAnulty | 5,718,548 A | 2/1998 | Cotellessa |
| 5,613,966 A | 3/1997 | Makower et al. | 5,720,744 A | 2/1998 | Eggleston et al. |
| 5,618,294 A | 4/1997 | Aust et al. | D393,067 S | 3/1998 | Geary et al. |
| 5,618,303 A | 4/1997 | Marlow et al. | 5,725,536 A | 3/1998 | Oberlin et al. |
| 5,620,289 A | 4/1997 | Curry | 5,725,554 A | 3/1998 | Simon et al. |
| 5,624,452 A | 4/1997 | Yates | 5,728,121 A | 3/1998 | Bimbo et al. |
| 5,626,587 A | 5/1997 | Bishop et al. | 5,730,758 A | 3/1998 | Allgeyer |
| 5,628,446 A | 5/1997 | Geiste et al. | 5,732,871 A | 3/1998 | Clark et al. |
| 5,628,743 A | 5/1997 | Cimino | 5,732,872 A | 3/1998 | Bolduc et al. |
| 5,630,539 A | 5/1997 | Plyley et al. | 5,735,445 A | 4/1998 | Vidal et al. |
| 5,630,540 A | 5/1997 | Blewett | 5,735,848 A | 4/1998 | Yates et al. |
| 5,630,782 A | 5/1997 | Adair | 5,735,874 A | 4/1998 | Measamer et al. |
| 5,632,432 A | 5/1997 | Schulze et al. | 5,738,474 A | 4/1998 | Blewett |
| 5,632,433 A | 5/1997 | Grant et al. | 5,738,648 A | 4/1998 | Lands et al. |
| 5,634,584 A | 6/1997 | Okorocha et al. | 5,743,456 A | 4/1998 | Jones et al. |
| 5,636,779 A | 6/1997 | Palmer | 5,747,953 A | 5/1998 | Philipp |
| 5,636,780 A | 6/1997 | Green et al. | 5,749,889 A | 5/1998 | Bacich et al. |
| 5,639,008 A | 6/1997 | Gallagher et al. | 5,749,893 A | 5/1998 | Vidal et al. |
| 5,643,291 A | 7/1997 | Pier et al. | 5,752,644 A | 5/1998 | Bolanos et al. |
| 5,645,209 A | 7/1997 | Green et al. | 5,752,965 A | 5/1998 | Francis et al. |

| | | | | | |
|---|---|---|---|---|---|
| 5,755,717 A | 5/1998 | Yates et al. | 5,919,198 A | 7/1999 | Graves, Jr. et al. |
| 5,758,814 A | 6/1998 | Gallagher et al. | 5,928,256 A | 7/1999 | Riza |
| 5,762,255 A | 6/1998 | Chrisman et al. | 5,931,847 A | 8/1999 | Bittner et al. |
| 5,762,256 A | 6/1998 | Mastri et al. | 5,931,853 A | 8/1999 | McEwen et al. |
| 5,766,188 A | 6/1998 | Igaki | 5,938,667 A | 8/1999 | Peyser et al. |
| 5,766,205 A | 6/1998 | Zvenyatsky et al. | 5,941,442 A | 8/1999 | Geiste et al. |
| 5,769,892 A | 6/1998 | Kingwell | 5,944,172 A | 8/1999 | Hannula |
| 5,772,578 A | 6/1998 | Heimberger et al. | 5,944,715 A | 8/1999 | Goble et al. |
| 5,772,659 A | 6/1998 | Becker et al. | 5,948,030 A | 9/1999 | Miller et al. |
| 5,776,130 A | 7/1998 | Buysse et al. | 5,951,552 A | 9/1999 | Long et al. |
| 5,779,130 A | 7/1998 | Alesi et al. | 5,951,574 A | 9/1999 | Stefanchik et al. |
| 5,779,131 A | 7/1998 | Knodel et al. | 5,954,259 A | 9/1999 | Viola et al. |
| 5,779,132 A | 7/1998 | Knodel et al. | 5,964,774 A | 10/1999 | McKean et al. |
| 5,782,396 A | 7/1998 | Mastri et al. | 5,988,479 A | 11/1999 | Palmer |
| 5,782,397 A | 7/1998 | Koukline | 6,003,517 A | 12/1999 | Sheffield et al. |
| 5,782,749 A | 7/1998 | Riza | 6,004,319 A | 12/1999 | Goble et al. |
| 5,782,859 A | 7/1998 | Nicholas et al. | 6,010,054 A | 1/2000 | Johnson et al. |
| 5,784,934 A | 7/1998 | Izumisawa | 6,012,494 A | 1/2000 | Balazs |
| 5,785,232 A | 7/1998 | Vidal et al. | 6,013,076 A | 1/2000 | Goble et al. |
| 5,787,897 A | 8/1998 | Kieturakis | 6,015,406 A | 1/2000 | Goble et al. |
| 5,792,135 A | 8/1998 | Madhani et al. | 6,017,356 A | 1/2000 | Frederick et al. |
| 5,792,165 A | 8/1998 | Klieman et al. | 6,022,352 A | 2/2000 | Vandewalle |
| 5,794,834 A | 8/1998 | Hamblin et al. | 6,024,741 A | 2/2000 | Williamson, IV et al. |
| 5,796,188 A | 8/1998 | Bays | 6,024,748 A | 2/2000 | Manzo et al. |
| 5,797,536 A | 8/1998 | Smith et al. | 6,027,501 A | 2/2000 | Goble et al. |
| 5,797,537 A | 8/1998 | Oberlin et al. | 6,032,849 A | 3/2000 | Mastri et al. |
| 5,797,538 A | 8/1998 | Heaton et al. | 6,033,378 A | 3/2000 | Lundquist et al. |
| 5,797,906 A | 8/1998 | Rhum et al. | 6,033,399 A | 3/2000 | Gines |
| 5,797,959 A | 8/1998 | Castro et al. | 6,033,427 A | 3/2000 | Lee |
| 5,799,857 A | 9/1998 | Robertson et al. | 6,039,733 A | 3/2000 | Buysse et al. |
| 5,807,393 A | 9/1998 | Williamson, IV et al. | 6,039,734 A | 3/2000 | Goble |
| 5,809,441 A | 9/1998 | McKee | 6,045,560 A | 4/2000 | McKean et al. |
| 5,810,811 A | 9/1998 | Yates et al. | 6,050,472 A | 4/2000 | Shibata |
| 5,810,855 A | 9/1998 | Rayburn et al. | 6,053,390 A | 4/2000 | Green et al. |
| 5,813,813 A | 9/1998 | Daum et al. | 6,056,746 A | 5/2000 | Goble et al. |
| 5,814,057 A | 9/1998 | Oi et al. | 6,063,097 A | 5/2000 | Oi et al. |
| 5,817,084 A | 10/1998 | Jensen | 6,068,627 A | 5/2000 | Orszulak et al. |
| 5,817,091 A | 10/1998 | Nardella et al. | 6,071,233 A | 6/2000 | Ishikawa et al. |
| 5,817,093 A | 10/1998 | Williamson, IV et al. | 6,074,386 A | 6/2000 | Goble et al. |
| 5,817,109 A | 10/1998 | McGarry et al. | 6,077,286 A | 6/2000 | Cuschieri et al. |
| 5,817,119 A | 10/1998 | Klieman et al. | 6,079,606 A | 6/2000 | Milliman et al. |
| 5,820,009 A | 10/1998 | Melling et al. | 6,082,577 A | 7/2000 | Coates et al. |
| 5,823,066 A | 10/1998 | Huitema et al. | 6,083,234 A | 7/2000 | Nicholas et al. |
| 5,826,776 A | 10/1998 | Schulze et al. | 6,083,242 A | 7/2000 | Cook |
| 5,827,271 A | 10/1998 | Buysse et al. | 6,086,600 A | 7/2000 | Kortenbach |
| 5,829,662 A | 11/1998 | Allen et al. | 6,090,106 A | 7/2000 | Goble et al. |
| 5,833,690 A | 11/1998 | Yates et al. | 6,093,186 A | 7/2000 | Goble |
| 5,833,695 A | 11/1998 | Yoon | 6,099,537 A | 8/2000 | Sugai et al. |
| 5,833,696 A | 11/1998 | Whitfield et al. | 6,099,551 A | 8/2000 | Gabbay |
| 5,836,503 A | 11/1998 | Ehrenfels et al. | 6,102,271 A | 8/2000 | Longo et al. |
| 5,836,960 A | 11/1998 | Kolesa et al. | 6,109,500 A | 8/2000 | Alli et al. |
| 5,839,639 A | 11/1998 | Sauer et al. | 6,117,158 A | 9/2000 | Measamer et al. |
| 5,843,132 A | 12/1998 | Ilvento | 6,119,913 A | 9/2000 | Adams et al. |
| 5,846,254 A | 12/1998 | Schulze et al. | 6,123,241 A | 9/2000 | Walter et al. |
| 5,849,011 A | 12/1998 | Jones et al. | H1904 H | 10/2000 | Yates et al. |
| 5,855,311 A | 1/1999 | Hamblin et al. | 6,126,058 A | 10/2000 | Adams et al. |
| 5,860,975 A | 1/1999 | Goble et al. | 6,126,670 A | 10/2000 | Walker et al. |
| 5,865,361 A | 2/1999 | Milliman et al. | 6,131,789 A | 10/2000 | Schulze et al. |
| 5,868,760 A | 2/1999 | McGuckin, Jr. | 6,132,368 A | 10/2000 | Cooper |
| 5,871,135 A | 2/1999 | Williamson IV et al. | 6,139,546 A | 10/2000 | Koenig et al. |
| 5,873,885 A | 2/1999 | Weidenbenner | 6,155,473 A | 12/2000 | Tompkins et al. |
| 5,876,401 A | 3/1999 | Schulze et al. | 6,156,056 A | 12/2000 | Kearns et al. |
| 5,878,193 A | 3/1999 | Wang et al. | 6,159,146 A | 12/2000 | El Gazayerli |
| 5,878,937 A | 3/1999 | Green et al. | 6,159,200 A | 12/2000 | Verdura et al. |
| 5,878,938 A | 3/1999 | Bittner et al. | 6,162,208 A | 12/2000 | Hipps |
| 5,891,160 A | 4/1999 | Williamson, IV et al. | 6,165,175 A | 12/2000 | Wampler et al. |
| 5,893,506 A | 4/1999 | Powell | 6,168,605 B1 | 1/2001 | Measamer et al. |
| 5,894,979 A | 4/1999 | Powell | 6,171,316 B1 | 1/2001 | Kovac et al. |
| 5,897,562 A | 4/1999 | Bolanos et al. | 6,171,330 B1 | 1/2001 | Benchetrit |
| 5,899,914 A | 5/1999 | Zirps et al. | 6,174,308 B1 | 1/2001 | Goble et al. |
| 5,901,895 A | 5/1999 | Heaton et al. | 6,179,776 B1 | 1/2001 | Adams et al. |
| 5,902,312 A | 5/1999 | Frater et al. | 6,181,105 B1 | 1/2001 | Cutolo et al. |
| 5,904,693 A | 5/1999 | Dicesare et al. | 6,193,129 B1 | 2/2001 | Bittner et al. |
| 5,906,625 A | 5/1999 | Bito et al. | 6,197,042 B1 | 3/2001 | Ginn et al. |
| 5,908,402 A | 6/1999 | Blythe | 6,202,914 B1 | 3/2001 | Geiste et al. |
| 5,908,427 A | 6/1999 | McKean et al. | 6,214,028 B1 | 4/2001 | Yoon et al. |
| 5,911,353 A | 6/1999 | Bolanos et al. | 6,220,368 B1 | 4/2001 | Ark et al. |
| 5,915,616 A | 6/1999 | Viola et al. | 6,223,835 B1 | 5/2001 | Habedank et al. |
| 5,918,791 A | 7/1999 | Sorrentino et al. | 6,228,081 B1 | 5/2001 | Goble |

| Patent | Type | Date | Inventor |
|---|---|---|---|
| 6,228,084 | B1 | 5/2001 | Kirwan, Jr. |
| 6,231,565 | B1 | 5/2001 | Tovey et al. |
| 6,234,178 | B1 | 5/2001 | Goble et al. |
| 6,241,139 | B1 | 6/2001 | Milliman et al. |
| 6,241,723 | B1 | 6/2001 | Heim et al. |
| 6,249,076 | B1 | 6/2001 | Madden et al. |
| 6,250,532 | B1 | 6/2001 | Green et al. |
| 6,258,107 | B1 | 7/2001 | Balázs et al. |
| 6,261,286 | B1 | 7/2001 | Goble et al. |
| 6,264,086 | B1 | 7/2001 | McGuckin, Jr. |
| 6,264,087 | B1 | 7/2001 | Whitman |
| 6,270,508 | B1 | 8/2001 | Klieman et al. |
| 6,273,897 | B1 | 8/2001 | Dalessandro et al. |
| 6,277,114 | B1 | 8/2001 | Bullivant et al. |
| 6,293,942 | B1 | 9/2001 | Goble et al. |
| 6,296,640 | B1 | 10/2001 | Wampler et al. |
| 6,302,311 | B1 | 10/2001 | Adams et al. |
| 6,306,134 | B1 | 10/2001 | Goble et al. |
| 6,309,403 | B1 | 10/2001 | Minor et al. |
| 6,315,184 | B1 | 11/2001 | Whitman |
| 6,320,123 | B1 | 11/2001 | Reimers |
| 6,324,339 | B1 | 11/2001 | Hudson et al. |
| 6,325,799 | B1 | 12/2001 | Goble |
| 6,325,810 | B1 | 12/2001 | Hamilton et al. |
| 6,330,965 | B1 | 12/2001 | Milliman et al. |
| 6,331,761 | B1 | 12/2001 | Kumar et al. |
| 6,336,926 | B1 | 1/2002 | Goble |
| 6,346,077 | B1 | 2/2002 | Taylor et al. |
| 6,352,503 | B1 | 3/2002 | Matsui et al. |
| 6,358,224 | B1 | 3/2002 | Tims et al. |
| 6,364,877 | B1 | 4/2002 | Goble et al. |
| 6,364,888 | B1 | 4/2002 | Niemeyer et al. |
| 6,387,113 | B1 | 5/2002 | Hawkins et al. |
| 6,387,114 | B2 | 5/2002 | Adams |
| 6,398,781 | B1 | 6/2002 | Goble et al. |
| 6,398,797 | B2 | 6/2002 | Bombard et al. |
| 6,406,440 | B1 | 6/2002 | Stefanchik |
| 6,409,724 | B1 | 6/2002 | Penny et al. |
| H2037 | H | 7/2002 | Yates et al. |
| 6,416,486 | B1 | 7/2002 | Wampler |
| 6,416,509 | B1 | 7/2002 | Goble et al. |
| RE37,814 | E | 8/2002 | Allgeyer |
| 6,436,097 | B1 | 8/2002 | Nardella |
| 6,436,107 | B1 | 8/2002 | Wang et al. |
| 6,436,122 | B1 | 8/2002 | Frank et al. |
| 6,440,146 | B2 | 8/2002 | Nicholas et al. |
| 6,443,973 | B1 | 9/2002 | Whitman |
| 6,468,275 | B1 | 10/2002 | Wampler et al. |
| 6,471,106 | B1 | 10/2002 | Reining |
| 6,482,200 | B2 | 11/2002 | Shippert |
| 6,485,490 | B2 | 11/2002 | Wampler et al. |
| 6,488,196 | B1 | 12/2002 | Fenton, Jr. |
| 6,488,197 | B1 | 12/2002 | Whitman |
| 6,491,201 | B1 | 12/2002 | Whitman |
| 6,491,690 | B1 | 12/2002 | Goble et al. |
| 6,492,785 | B1 | 12/2002 | Kasten et al. |
| 6,494,896 | B1 | 12/2002 | D'Alessio et al. |
| 6,503,257 | B2 | 1/2003 | Grant et al. |
| 6,503,259 | B2 | 1/2003 | Huxel et al. |
| 6,505,768 | B2 | 1/2003 | Whitman |
| 6,510,854 | B2 | 1/2003 | Goble |
| 6,511,468 | B1 | 1/2003 | Cragg et al. |
| 6,517,535 | B2 | 2/2003 | Edwards |
| 6,517,565 | B1 | 2/2003 | Whitman et al. |
| 6,522,101 | B2 | 2/2003 | Malackowski |
| 6,543,456 | B1 | 4/2003 | Freeman |
| 6,547,786 | B1 | 4/2003 | Goble |
| 6,550,546 | B2 | 4/2003 | Thurler et al. |
| 6,551,333 | B2 | 4/2003 | Kuhns et al. |
| 6,554,861 | B2 | 4/2003 | Knox et al. |
| 6,558,379 | B1 | 5/2003 | Batchelor et al. |
| 6,565,560 | B1 | 5/2003 | Goble et al. |
| 6,569,085 | B2 | 5/2003 | Kortenbach et al. |
| 6,569,171 | B2 | 5/2003 | DeGuillebon et al. |
| 6,578,751 | B2 | 6/2003 | Hartwick |
| 6,582,427 | B1 | 6/2003 | Goble et al. |
| 6,588,643 | B2 | 7/2003 | Bolduc et al. |
| 6,592,597 | B2 | 7/2003 | Grant et al. |
| 6,596,432 | B2 | 7/2003 | Kawakami et al. |
| D478,665 | S | 8/2003 | Isaacs et al. |
| D478,986 | S | 8/2003 | Johnston et al. |
| 6,601,749 | B2 | 8/2003 | Sullivan et al. |
| 6,602,252 | B2 | 8/2003 | Mollenauer |
| 6,605,078 | B2 | 8/2003 | Adams |
| 6,605,669 | B2 | 8/2003 | Awokola et al. |
| 6,616,686 | B2 | 9/2003 | Coleman et al. |
| 6,619,529 | B2 | 9/2003 | Green et al. |
| 6,620,166 | B1 | 9/2003 | Wenstrom, Jr. et al. |
| 6,629,630 | B2 | 10/2003 | Adams |
| 6,629,974 | B2 | 10/2003 | Penny et al. |
| 6,629,988 | B2 | 10/2003 | Weadock |
| 6,636,412 | B2 | 10/2003 | Smith |
| 6,638,108 | B2 | 10/2003 | Tachi |
| 6,638,285 | B2 | 10/2003 | Gabbay |
| 6,644,532 | B2 | 11/2003 | Green et al. |
| 6,648,816 | B2 | 11/2003 | Irion et al. |
| D484,243 | S | 12/2003 | Ryan et al. |
| D484,595 | S | 12/2003 | Ryan et al. |
| D484,596 | S | 12/2003 | Ryan et al. |
| 6,656,193 | B2 | 12/2003 | Grant et al. |
| 6,666,875 | B1 | 12/2003 | Sakurai et al. |
| 6,669,073 | B2 | 12/2003 | Milliman et al. |
| D484,977 | S | 1/2004 | Ryan et al. |
| 6,676,660 | B2 | 1/2004 | Wampler et al. |
| 6,679,410 | B2 | 1/2004 | Würsch et al. |
| 6,681,978 | B2 | 1/2004 | Geiste et al. |
| 6,681,979 | B2 | 1/2004 | Whitman |
| 6,682,528 | B2 | 1/2004 | Frazier et al. |
| 6,685,727 | B2 | 2/2004 | Fisher et al. |
| 6,695,199 | B2 | 2/2004 | Whitman |
| 6,698,643 | B2 | 3/2004 | Whitman |
| 6,704,210 | B1 | 3/2004 | Myers |
| 6,705,503 | B1 | 3/2004 | Pedicini et al. |
| 6,716,223 | B2 | 4/2004 | Leopold et al. |
| 6,716,232 | B1 | 4/2004 | Vidal et al. |
| 6,716,233 | B1 | 4/2004 | Whitman |
| 6,723,087 | B2 | 4/2004 | O'Neill et al. |
| 6,723,091 | B2 | 4/2004 | Goble et al. |
| 6,726,697 | B2 | 4/2004 | Nicholas et al. |
| 6,740,030 | B2 | 5/2004 | Martone et al. |
| 6,747,121 | B2 | 6/2004 | Gogolewski |
| 6,749,560 | B1 | 6/2004 | Konstorum et al. |
| 6,752,768 | B2 | 6/2004 | Burdorff et al. |
| 6,752,816 | B2 | 6/2004 | Culp et al. |
| 6,755,338 | B2 | 6/2004 | Hahnen et al. |
| 6,758,846 | B2 | 7/2004 | Goble et al. |
| 6,761,685 | B2 | 7/2004 | Adams et al. |
| 6,767,356 | B2 | 7/2004 | Kanner et al. |
| 6,769,594 | B2 | 8/2004 | Orban, III |
| 6,773,438 | B1 | 8/2004 | Knodel et al. |
| 6,780,151 | B2 | 8/2004 | Grabover et al. |
| 6,780,180 | B2 | 8/2004 | Goble et al. |
| 6,783,524 | B2 | 8/2004 | Anderson et al. |
| 6,786,382 | B1 | 9/2004 | Hoffman |
| 6,786,864 | B2 | 9/2004 | Matsuura et al. |
| 6,786,896 | B2 | 9/2004 | Madani et al. |
| 6,790,173 | B2 | 9/2004 | Saadat et al. |
| 6,793,652 | B1 | 9/2004 | Whitman et al. |
| 6,805,273 | B2 | 10/2004 | Bilotti et al. |
| 6,806,808 | B1 | 10/2004 | Watters et al. |
| 6,808,525 | B2 | 10/2004 | Latterell et al. |
| 6,814,741 | B2 | 11/2004 | Bowman et al. |
| 6,817,508 | B1 | 11/2004 | Racenet et al. |
| 6,817,509 | B2 | 11/2004 | Geiste et al. |
| 6,817,974 | B2 | 11/2004 | Cooper et al. |
| 6,821,273 | B2 | 11/2004 | Mollenauer |
| 6,827,725 | B2 | 12/2004 | Batchelor et al. |
| 6,828,902 | B2 | 12/2004 | Casden |
| 6,830,174 | B2 | 12/2004 | Hillstead et al. |
| 6,832,998 | B2 | 12/2004 | Goble |
| 6,834,001 | B2 | 12/2004 | Myono |
| 6,835,199 | B2 | 12/2004 | McGuckin, Jr. et al. |
| 6,843,403 | B2 | 1/2005 | Whitman |
| 6,843,789 | B2 | 1/2005 | Goble |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,849,071 | B2 | 2/2005 | Whitman et al. |

| | | | | | | |
|---|---|---|---|---|---|---|
| RE38,708 E | 3/2005 | Bolanos et al. | | 7,104,741 B2 | 9/2006 | Krohn |
| 6,872,214 B2 | 3/2005 | Sonnenschein et al. | | 7,108,695 B2 | 9/2006 | Witt et al. |
| 6,874,669 B2 | 4/2005 | Adams et al. | | 7,108,701 B2 | 9/2006 | Evens et al. |
| 6,877,647 B2 | 4/2005 | Green et al. | | 7,108,709 B2 | 9/2006 | Cummins |
| 6,878,106 B1 | 4/2005 | Herrmann | | 7,111,769 B2 | 9/2006 | Wales et al. |
| 6,893,435 B2 | 5/2005 | Goble | | 7,112,214 B2 | 9/2006 | Peterson et al. |
| 6,905,057 B2 | 6/2005 | Swayze et al. | | RE39,358 E | 10/2006 | Goble |
| 6,905,497 B2 | 6/2005 | Truckai et al. | | 7,114,642 B2 | 10/2006 | Whitman |
| 6,913,608 B2 | 7/2005 | Liddicoat et al. | | 7,118,582 B1 | 10/2006 | Wang et al. |
| 6,913,613 B2 | 7/2005 | Schwarz et al. | | 7,121,446 B2 * | 10/2006 | Arad et al. .................. 227/176.1 |
| 6,923,803 B2 | 8/2005 | Goble | | 7,122,028 B2 | 10/2006 | Looper et al. |
| 6,929,641 B2 | 8/2005 | Goble et al. | | 7,128,253 B2 | 10/2006 | Mastri et al. |
| 6,931,830 B2 | 8/2005 | Liao | | 7,128,254 B2 | 10/2006 | Shelton, IV et al. |
| 6,939,358 B2 | 9/2005 | Palacios et al. | | 7,128,748 B2 | 10/2006 | Mooradian et al. |
| 6,942,662 B2 | 9/2005 | Goble et al. | | 7,131,445 B2 | 11/2006 | Amoah |
| 6,945,444 B2 | 9/2005 | Gresham et al. | | 7,133,601 B2 | 11/2006 | Phillips et al. |
| 6,953,138 B1 | 10/2005 | Dworak et al. | | 7,140,527 B2 | 11/2006 | Ehrenfels et al. |
| 6,953,139 B2 | 10/2005 | Milliman et al. | | 7,140,528 B2 | 11/2006 | Shelton, IV |
| 6,959,852 B2 | 11/2005 | Shelton, IV et al. | | 7,143,923 B2 | 12/2006 | Shelton, IV et al. |
| 6,960,163 B2 | 11/2005 | Ewers et al. | | 7,143,924 B2 | 12/2006 | Scirica et al. |
| 6,960,220 B2 | 11/2005 | Marino et al. | | 7,143,925 B2 | 12/2006 | Shelton, IV et al. |
| 6,964,363 B2 | 11/2005 | Wales et al. | | 7,143,926 B2 | 12/2006 | Shelton, IV et al. |
| 6,966,907 B2 | 11/2005 | Goble | | 7,147,138 B2 | 12/2006 | Shelton, IV |
| 6,966,909 B2 | 11/2005 | Marshall et al. | | 7,147,139 B2 | 12/2006 | Schwemberger et al. |
| 6,972,199 B2 | 12/2005 | Lebouitz et al. | | 7,147,637 B2 | 12/2006 | Goble |
| 6,974,462 B2 | 12/2005 | Sater | | 7,147,650 B2 | 12/2006 | Lee |
| 6,978,921 B2 | 12/2005 | Shelton, IV et al. | | 7,150,748 B2 | 12/2006 | Ebbutt et al. |
| 6,978,922 B2 | 12/2005 | Bilotti et al. | | 7,153,300 B2 | 12/2006 | Goble |
| 6,981,628 B2 | 1/2006 | Wales | | 7,156,863 B2 | 1/2007 | Sonnenschein et al. |
| 6,981,941 B2 | 1/2006 | Whitman et al. | | 7,159,750 B2 | 1/2007 | Racenet et al. |
| 6,981,978 B2 | 1/2006 | Gannoe | | 7,160,299 B2 | 1/2007 | Baily |
| 6,984,203 B2 | 1/2006 | Tartaglia et al. | | 7,161,036 B2 | 1/2007 | Oikawa et al. |
| 6,984,231 B2 | 1/2006 | Goble et al. | | 7,168,604 B2 | 1/2007 | Milliman et al. |
| 6,986,451 B1 | 1/2006 | Mastri et al. | | 7,172,104 B2 | 2/2007 | Scirica et al. |
| 6,988,649 B2 | 1/2006 | Shelton, IV et al. | | 7,179,223 B2 | 2/2007 | Motoki et al. |
| 6,988,650 B2 | 1/2006 | Schwemberger et al. | | 7,179,267 B2 | 2/2007 | Nolan et al. |
| 6,990,796 B2 | 1/2006 | Schnipke et al. | | 7,182,239 B1 | 2/2007 | Myers |
| 6,997,931 B2 | 2/2006 | Sauer et al. | | 7,188,758 B2 | 3/2007 | Viola et al. |
| 7,000,818 B2 | 2/2006 | Shelton, IV et al. | | 7,195,627 B2 | 3/2007 | Amoah et al. |
| 7,000,819 B2 | 2/2006 | Swayze et al. | | 7,204,835 B2 | 4/2007 | Latterell et al. |
| 7,001,380 B2 | 2/2006 | Goble | | 7,207,233 B2 | 4/2007 | Wadge |
| 7,001,408 B2 | 2/2006 | Knodel et al. | | 7,207,471 B2 | 4/2007 | Heinrich et al. |
| 7,008,435 B2 | 3/2006 | Cummins | | 7,207,472 B2 | 4/2007 | Wukusick et al. |
| 7,018,390 B2 | 3/2006 | Turovskiy et al. | | 7,208,005 B2 | 4/2007 | Frecker et al. |
| 7,025,743 B2 | 4/2006 | Mann et al. | | 7,210,609 B2 | 5/2007 | Leiboff et |
| 7,029,435 B2 | 4/2006 | Nakao | | 7,211,081 B2 | 5/2007 | Goble |
| 7,032,798 B2 | 4/2006 | Whitman et al. | | 7,211,084 B2 | 5/2007 | Goble et al. |
| 7,032,799 B2 | 4/2006 | Viola et al. | | 7,213,736 B2 | 5/2007 | Wales et al. |
| 7,033,356 B2 | 4/2006 | Latterell et al. | | 7,214,224 B2 | 5/2007 | Goble |
| 7,036,680 B1 | 5/2006 | Flannery | | 7,220,260 B2 | 5/2007 | Fleming et al. |
| 7,037,344 B2 | 5/2006 | Kagan et al. | | 7,220,272 B2 | 5/2007 | Weadock |
| 7,044,352 B2 | 5/2006 | Shelton, IV et al. | | 7,225,964 B2 | 6/2007 | Mastri et al. |
| 7,044,353 B2 | 5/2006 | Mastri et al. | | 7,234,624 B2 | 6/2007 | Gresham et al. |
| 7,048,687 B1 | 5/2006 | Reuss et al. | | 7,235,089 B1 | 6/2007 | McGuckin, Jr. |
| 7,052,494 B2 | 5/2006 | Goble et al. | | 7,235,302 B2 | 6/2007 | Jing et al. |
| 7,055,730 B2 | 6/2006 | Ehrenfels et al. | | 7,237,708 B1 | 7/2007 | Guy et al. |
| 7,055,731 B2 | 6/2006 | Shelton, IV et al. | | 7,238,195 B2 | 7/2007 | Viola |
| 7,056,284 B2 | 6/2006 | Martone et al. | | 7,241,288 B2 | 7/2007 | Braun |
| 7,056,330 B2 | 6/2006 | Gayton | | 7,246,734 B2 | 7/2007 | Shelton, IV |
| 7,059,508 B2 | 6/2006 | Shelton, IV et al. | | 7,247,161 B2 | 7/2007 | Johnston et al. |
| 7,063,712 B2 | 6/2006 | Vargas et al. | | 7,252,660 B2 | 8/2007 | Kunz |
| 7,066,944 B2 | 6/2006 | Laufer et al. | | 7,255,696 B2 | 8/2007 | Goble et al. |
| 7,070,083 B2 | 7/2006 | Jankowski | | 7,258,262 B2 | 8/2007 | Mastri et al. |
| 7,070,559 B2 | 7/2006 | Adams et al. | | 7,260,431 B2 | 8/2007 | Libbus et al. |
| 7,071,287 B2 | 7/2006 | Rhine et al. | | 7,265,374 B2 | 9/2007 | Lee et al. |
| 7,075,770 B1 | 7/2006 | Smith | | 7,267,679 B2 | 9/2007 | McGuckin, Jr. et al. |
| 7,077,856 B2 | 7/2006 | Whitman | | 7,278,562 B2 | 10/2007 | Mastri et al. |
| 7,080,769 B2 | 7/2006 | Vresh et al. | | 7,278,563 B1 | 10/2007 | Green |
| 7,081,114 B2 | 7/2006 | Rashidi | | 7,278,994 B2 | 10/2007 | Goble |
| 7,083,073 B2 | 8/2006 | Yoshie et al. | | 7,282,048 B2 | 10/2007 | Goble et al. |
| 7,083,075 B2 | 8/2006 | Swayze et al. | | 7,295,907 B2 | 11/2007 | Lu et al. |
| 7,083,571 B2 | 8/2006 | Wang et al. | | 7,296,724 B2 | 11/2007 | Green et al. |
| 7,087,071 B2 | 8/2006 | Nicholas et al. | | 7,297,149 B2 | 11/2007 | Vitali et al. |
| 7,090,637 B2 | 8/2006 | Danitz et al. | | 7,300,450 B2 | 11/2007 | Vleugels et al. |
| 7,090,673 B2 | 8/2006 | Dycus et al. | | 7,303,106 B2 | 12/2007 | Milliman et al. |
| 7,090,684 B2 | 8/2006 | McGuckin, Jr. et al. | | 7,303,107 B2 | 12/2007 | Milliman et al. |
| 7,094,202 B2 | 8/2006 | Nobis et al. | | 7,303,108 B2 | 12/2007 | Shelton, IV |
| 7,097,089 B2 | 8/2006 | Marczyk | | 7,303,556 B2 | 12/2007 | Metzger |
| 7,098,794 B2 | 8/2006 | Lindsay et al. | | 7,324,572 B2 | 1/2008 | Chang |

| Patent | Type | Date | Inventor |
|---|---|---|---|
| 7,328,828 | B2 | 2/2008 | Ortiz et al. |
| 7,328,829 | B2 | 2/2008 | Arad et al. |
| 7,330,004 | B2 | 2/2008 | DeJonge et al. |
| 7,334,717 | B2 | 2/2008 | Rethy et al. |
| 7,336,184 | B2 | 2/2008 | Smith et al. |
| 7,338,513 | B2 | 3/2008 | Lee et al. |
| 7,343,920 | B2 | 3/2008 | Toby et al. |
| 7,348,763 | B1 | 3/2008 | Reinhart et al. |
| 7,351,258 | B2 | 4/2008 | Ricotta et al. |
| 7,354,447 | B2 | 4/2008 | Shelton, IV et al. |
| 7,364,060 | B2 | 4/2008 | Milliman |
| 7,364,061 | B2 | 4/2008 | Swayze et al. |
| 7,377,928 | B2 | 5/2008 | Zubik et al. |
| 7,380,695 | B2 | 6/2008 | Doll et al. |
| 7,380,696 | B2 | 6/2008 | Shelton, IV et al. |
| 7,388,217 | B2 | 6/2008 | Buschbeck et al. |
| 7,396,356 | B2 | 7/2008 | Mollenauer |
| 7,397,364 | B2 | 7/2008 | Govari |
| 7,398,907 | B2 | 7/2008 | Racenet et al. |
| 7,398,908 | B2 | 7/2008 | Holsten et al. |
| 7,404,508 | B2 | 7/2008 | Smith et al. |
| 7,404,509 | B2 | 7/2008 | Ortiz et al. |
| 7,407,075 | B2 | 8/2008 | Holsten et al. |
| 7,407,078 | B2 | 8/2008 | Shelton, IV et al. |
| 7,410,086 | B2 | 8/2008 | Ortiz et al. |
| 7,416,101 | B2 | 8/2008 | Shelton, IV et al. |
| 7,418,078 | B2 | 8/2008 | Blanz et al. |
| 7,419,080 | B2 | 9/2008 | Smith et al. |
| 7,422,136 | B1 | 9/2008 | Marczyk |
| 7,422,139 | B2 | 9/2008 | Shelton, IV et al. |
| 7,424,965 | B2 | 9/2008 | Racenet et al. |
| 7,431,188 | B1 | 10/2008 | Marczyk |
| 7,431,189 | B2 | 10/2008 | Shelton, IV et al. |
| 7,431,694 | B2 | 10/2008 | Stefanchik et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,438,209 | B1 | 10/2008 | Hess et al. |
| 7,439,354 | B2 | 10/2008 | Lenges et al. |
| 7,441,684 | B2 | 10/2008 | Shelton, IV et al. |
| 7,441,685 | B1 | 10/2008 | Boudreaux |
| 7,448,525 | B2 | 11/2008 | Shelton, IV et al. |
| 7,455,208 | B2 | 11/2008 | Wales et al. |
| 7,461,767 | B2 | 12/2008 | Viola et al. |
| 7,464,846 | B2 | 12/2008 | Shelton, IV et al. |
| 7,464,847 | B2 | 12/2008 | Viola et al. |
| 7,464,849 | B2 | 12/2008 | Shelton, IV et al. |
| 7,467,740 | B2 | 12/2008 | Shelton, IV et al. |
| 7,472,814 | B2 | 1/2009 | Mastri et al. |
| 7,472,815 | B2 | 1/2009 | Shelton, IV et al. |
| 7,473,253 | B2 | 1/2009 | Dycus et al. |
| 7,481,347 | B2 | 1/2009 | Roy |
| 7,481,349 | B2 | 1/2009 | Holsten et al. |
| 7,481,824 | B2 | 1/2009 | Boudreaux et al. |
| 7,485,133 | B2 | 2/2009 | Cannon et al. |
| 7,490,749 | B2 | 2/2009 | Schall et al. |
| 7,494,039 | B2 | 2/2009 | Racenet et al. |
| 7,494,499 | B2 | 2/2009 | Nagase et al. |
| 7,500,979 | B2 | 3/2009 | Hueil et al. |
| 7,506,790 | B2 | 3/2009 | Shelton, IV |
| 7,506,791 | B2 | 3/2009 | Omaits et al. |
| 7,510,107 | B2 | 3/2009 | Timm et al. |
| 7,524,320 | B2 | 4/2009 | Tierney et al. |
| 7,530,985 | B2 | 5/2009 | Takemoto et al. |
| 7,546,940 | B2 | 6/2009 | Milliman et al. |
| 7,547,312 | B2 | 6/2009 | Bauman et al. |
| 7,549,564 | B2 | 6/2009 | Boudreaux |
| 7,552,854 | B2 | 6/2009 | Wixey et al. |
| 7,556,186 | B2 | 7/2009 | Milliman |
| 7,559,450 | B2 | 7/2009 | Wales et al. |
| 7,563,862 | B2 | 7/2009 | Sieg et al. |
| 7,566,300 | B2 | 7/2009 | Devierre et al. |
| 7,568,603 | B2 | 8/2009 | Shelton, IV et al. |
| 7,568,604 | B2 | 8/2009 | Ehrenfels et al. |
| 7,568,619 | B2 | 8/2009 | Todd et al. |
| 7,575,144 | B2 | 8/2009 | Ortiz et al. |
| 7,588,175 | B2 | 9/2009 | Timm et al. |
| 7,588,176 | B2 | 9/2009 | Timm et al. |
| 7,597,229 | B2 | 10/2009 | Boudreaux et al. |
| 7,600,663 | B2 | 10/2009 | Green |
| 7,604,150 | B2 | 10/2009 | Boudreaux |
| 7,604,151 | B2 | 10/2009 | Hess et al. |
| 7,607,557 | B2 | 10/2009 | Shelton, IV et al. |
| 7,611,038 | B2 | 11/2009 | Racenet et al. |
| 7,615,003 | B2 | 11/2009 | Stefanchik et al. |
| 7,631,793 | B2 | 12/2009 | Rethy et al. |
| 7,641,092 | B2 | 1/2010 | Kruszynski et al. |
| 7,641,093 | B2 | 1/2010 | Doll et al. |
| 7,644,848 | B2 | 1/2010 | Swayze et al. |
| 7,651,498 | B2 | 1/2010 | Shifrin et al. |
| 7,658,311 | B2 | 2/2010 | Boudreaux |
| 7,665,646 | B2 | 2/2010 | Prommersberger |
| 7,665,647 | B2 | 2/2010 | Shelton, IV et al. |
| 7,669,746 | B2 | 3/2010 | Shelton, IV |
| 7,669,747 | B2 | 3/2010 | Weisenburgh, II et al. |
| 7,670,334 | B2 | 3/2010 | Hueil et al. |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,674,255 | B2 | 3/2010 | Braun |
| 7,682,307 | B2 | 3/2010 | Danitz et al. |
| 7,686,826 | B2 | 3/2010 | Lee et al. |
| 7,691,098 | B2 | 4/2010 | Wallace et al. |
| 7,699,204 | B2 | 4/2010 | Viola |
| 7,717,312 | B2 | 5/2010 | Beetel |
| 7,721,930 | B2 | 5/2010 | McKenna et al. |
| 7,721,931 | B2 | 5/2010 | Shelton, IV et al. |
| 7,721,934 | B2 | 5/2010 | Shelton, IV et al. |
| 7,721,936 | B2 | 5/2010 | Shalton et al. |
| 7,722,610 | B2 | 5/2010 | Viola et al. |
| 7,726,537 | B2 | 6/2010 | Olson et al. |
| 7,726,538 | B2 | 6/2010 | Holsten et al. |
| 7,731,072 | B2 | 6/2010 | Timm et al. |
| 7,735,703 | B2 | 6/2010 | Morgan et al. |
| 7,738,971 | B2 | 6/2010 | Swayze et al. |
| 7,740,159 | B2 | 6/2010 | Shelton, IV et al. |
| 7,743,960 | B2 | 6/2010 | Whitman et al. |
| 7,744,627 | B2 | 6/2010 | Orban, III et al. |
| 7,753,245 | B2 | 7/2010 | Boudreaux et al. |
| 7,753,904 | B2 | 7/2010 | Shelton, IV et al. |
| 7,766,209 | B2 | 8/2010 | Baxter, III et al. |
| 7,766,210 | B2 | 8/2010 | Shelton, IV et al. |
| 7,770,775 | B2 | 8/2010 | Shelton, IV et al. |
| 7,771,396 | B2 | 8/2010 | Stefanchik et al. |
| 7,780,054 | B2 | 8/2010 | Wales |
| 7,780,685 | B2 | 8/2010 | Hunt et al. |
| 7,784,662 | B2 | 8/2010 | Wales et al. |
| 7,793,812 | B2 | 9/2010 | Moore et al. |
| 7,794,475 | B2 | 9/2010 | Hess et al. |
| 7,798,386 | B2 | 9/2010 | Schall et al. |
| 7,799,039 | B2 | 9/2010 | Shelton, IV et al. |
| 7,806,891 | B2 | 10/2010 | Nowlin et al. |
| 7,810,692 | B2 | 10/2010 | Hall et al. |
| 7,810,693 | B2 | 10/2010 | Broehl et al. |
| 7,815,565 | B2 | 10/2010 | Stefanchik et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,824,401 | B2 | 11/2010 | Manzo et al. |
| 7,828,794 | B2 | 11/2010 | Sartor |
| 7,828,808 | B2 | 11/2010 | Hinman et al. |
| 7,832,408 | B2 * | 11/2010 | Shelton et al. ................. 128/898 |
| 7,832,611 | B2 | 11/2010 | Boyden et al. |
| 7,832,612 | B2 | 11/2010 | Baxter, III et al. |
| 7,836,400 | B2 | 11/2010 | May et al. |
| 7,837,080 | B2 | 11/2010 | Schwemberger |
| 7,845,533 | B2 | 12/2010 | Marczyk et al. |
| 7,845,534 | B2 | 12/2010 | Viola et al. |
| 7,845,537 | B2 | 12/2010 | Shelton, IV et al. |
| 7,846,149 | B2 | 12/2010 | Jankowski |
| 7,857,185 | B2 | 12/2010 | Swayze et al. |
| 7,857,186 | B2 | 12/2010 | Baxter, III et al. |
| 7,861,906 | B2 | 1/2011 | Doll et al. |
| 7,866,527 | B2 | 1/2011 | Hall et al. |
| 7,870,989 | B2 | 1/2011 | Viola et al. |
| 7,887,530 | B2 | 2/2011 | Zemlok et al. |

| Patent/Pub No. | Date | Inventor |
|---|---|---|
| 7,900,805 B2 | 3/2011 | Shelton, IV et al. |
| 7,905,380 B2 * | 3/2011 | Shelton et al. .............. 227/178.1 |
| 7,905,381 B2 | 3/2011 | Baxter, III et al. |
| 7,909,191 B2 | 3/2011 | Baker et al. |
| 7,909,221 B2 | 3/2011 | Viola et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,950,560 B2 | 5/2011 | Zemlok et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,966,799 B2 | 6/2011 | Morgan et al. |
| 7,980,443 B2 | 7/2011 | Scheib et al. |
| 8,002,795 B2 | 8/2011 | Beetel |
| 8,011,551 B2 | 9/2011 | Marczyk et al. |
| D650,074 S | 12/2011 | Hunt et al. |
| 2002/0022836 A1 | 2/2002 | Goble et al. |
| 2002/0029036 A1 | 3/2002 | Goble et al. |
| 2002/0117534 A1 | 8/2002 | Green et al. |
| 2002/0134811 A1 | 9/2002 | Napier et al. |
| 2002/0165541 A1 | 11/2002 | Whitman |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0195387 A1 | 10/2003 | Kortenbach et al. |
| 2003/0216732 A1 | 11/2003 | Truckai et al. |
| 2003/0220660 A1 | 11/2003 | Kortenbach et al. |
| 2004/0002726 A1 | 1/2004 | Nunez et al. |
| 2004/0006340 A1 | 1/2004 | Latterell et al. |
| 2004/0006372 A1 | 1/2004 | Racenet et al. |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068307 A1 | 4/2004 | Goble |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0101822 A1 | 5/2004 | Wiesner et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0222268 A1 | 11/2004 | Bilotti et al. |
| 2004/0230214 A1 | 11/2004 | Donofrio et al. |
| 2004/0232201 A1 | 11/2004 | Wenchell et al. |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0254608 A1 | 12/2004 | Huitema et al. |
| 2004/0267310 A1 | 12/2004 | Racenet et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0080454 A1 | 4/2005 | Drews et al. |
| 2005/0085693 A1 | 4/2005 | Belson et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0154258 A1 | 7/2005 | Tartaglia et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0274768 A1 | 12/2005 | Cummins et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0100643 A1 | 5/2006 | Laufer et al. |
| 2006/0108393 A1 | 5/2006 | Heinrich et al. |
| 2006/0111710 A1 | 5/2006 | Goble et al. |
| 2006/0111711 A1 | 5/2006 | Goble |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0183246 A1 | 8/2006 | Wiesner et al. |
| 2006/0200123 A1 | 9/2006 | Ryan |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0245971 A1 | 11/2006 | Burns et al. |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |

| | | |
|---|---|---|
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0034668 A1 | 2/2007 | Holsten et al. |
| 2007/0055219 A1 | 3/2007 | Whitman et al. |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0135803 A1 | 6/2007 | Belson |
| 2007/0158358 A1 | 7/2007 | Mason, II et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0213750 A1 | 9/2007 | Weadock |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0246505 A1 | 10/2007 | Pace-Floridia et al. |
| 2007/0260278 A1 | 11/2007 | Wheeler et al. |
| 2007/0270784 A1 | 11/2007 | Smith et al. |
| 2007/0288044 A1 | 12/2007 | Jinno et al. |
| 2007/0295780 A1 | 12/2007 | Shelton et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0129253 A1 | 6/2008 | Shiue et al. |
| 2008/0140115 A1 | 6/2008 | Stopek |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0228029 A1 | 9/2008 | Mikkaichi et al. |
| 2008/0237296 A1 | 10/2008 | Boudreaux et al. |
| 2008/0251568 A1 | 10/2008 | Zemlok et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0020958 A1 | 1/2009 | Soul |
| 2009/0054908 A1 | 2/2009 | Zand et al. |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0157067 A1 | 6/2009 | Kane et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0292283 A1 | 11/2009 | Odom |
| 2009/0308907 A1 | 12/2009 | Nalagatla et al. |
| 2010/0001036 A1 | 1/2010 | Marczyk et al. |
| 2010/0023024 A1 | 1/2010 | Zeiner et al. |
| 2010/0032470 A1 | 2/2010 | Hess et al. |
| 2010/0049084 A1 | 2/2010 | Nock et al. |
| 2010/0065605 A1 | 3/2010 | Shelton, IV et al. |
| 2010/0069942 A1 | 3/2010 | Shelton, IV |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |

| | | | | | | | |
|---|---|---|---|---|---|---|---|
| 2010/0301096 | A1 | 12/2010 | Moore et al. | DE | 20121753 | U1 | 4/2003 |
| 2010/0305552 | A1 | 12/2010 | Shelton, IV et al. | DE | 10314072 | A1 | 10/2004 |
| 2010/0308100 | A1 | 12/2010 | Boudreaux | DE | 202007003114 | U1 | 6/2007 |
| 2010/0312261 | A1 | 12/2010 | Suzuki et al. | EP | 0122046 | A1 | 10/1984 |
| 2011/0006099 | A1 | 1/2011 | Hall et al. | EP | 0070230 | B1 | 10/1985 |
| 2011/0006101 | A1 | 1/2011 | Hall et al. | EP | 0387980 | B1 | 10/1985 |
| 2011/0006103 | A1 | 1/2011 | Laurent et al. | EP | 0033548 | B1 | 5/1986 |
| 2011/0011914 | A1 | 1/2011 | Baxter, III et al. | EP | 0276104 | A2 | 7/1988 |
| 2011/0011915 | A1 | 1/2011 | Shelton, IV | EP | 0248844 | B1 | 1/1993 |
| 2011/0017801 | A1 | 1/2011 | Zemlok et al. | EP | 0545029 | A1 | 6/1993 |
| 2011/0022032 | A1 | 1/2011 | Zemlok et al. | EP | 0277959 | B1 | 10/1993 |
| 2011/0024477 | A1 | 2/2011 | Hall et al. | EP | 0233940 | B1 | 11/1993 |
| 2011/0024478 | A1 | 2/2011 | Shelton, IV | EP | 0261230 | B1 | 11/1993 |
| 2011/0024479 | A1 | 2/2011 | Swensgard et al. | EP | 0639349 | A2 | 2/1994 |
| 2011/0036887 | A1 | 2/2011 | Zemlok et al. | EP | 0324636 | B1 | 3/1994 |
| 2011/0042441 | A1 | 2/2011 | Shelton, IV et al. | EP | 0593920 | A1 | 4/1994 |
| 2011/0060363 | A1 | 3/2011 | Hess et al. | EP | 0523174 | B1 | 6/1994 |
| 2011/0062212 | A1 | 3/2011 | Shelton, IV et al. | EP | 0600182 | A2 | 6/1994 |
| 2011/0068145 | A1 | 3/2011 | Bedi et al. | EP | 0310431 | B1 | 11/1994 |
| 2011/0068148 | A1 | 3/2011 | Hall et al. | EP | 0375302 | B1 | 11/1994 |
| 2011/0084112 | A1 | 4/2011 | Kostrzewski | EP | 0376562 | B1 | 11/1994 |
| 2011/0084113 | A1 | 4/2011 | Bedi et al. | EP | 0630612 | A1 | 12/1994 |
| 2011/0084115 | A1 | 4/2011 | Bedi et al. | EP | 0634144 | A1 | 1/1995 |
| 2011/0087276 | A1 | 4/2011 | Bedi et al. | EP | 0646356 | A2 | 4/1995 |
| 2011/0101065 | A1 | 5/2011 | Milliman | EP | 0646357 | A1 | 4/1995 |
| 2011/0114697 | A1 | 5/2011 | Baxter, III et al. | EP | 0653189 | A2 | 5/1995 |
| 2011/0114698 | A1 | 5/2011 | Baxter, III et al. | EP | 0669104 | A1 | 8/1995 |
| 2011/0114699 | A1 | 5/2011 | Baxter, III et al. | EP | 0511470 | B1 | 10/1995 |
| 2011/0114700 | A1 | 5/2011 | Baxter, III et al. | EP | 0679367 | A2 | 11/1995 |
| 2011/0118761 | A1 | 5/2011 | Baxter, III et al. | EP | 0392547 | B1 | 12/1995 |
| 2011/0121052 | A1 | 5/2011 | Shelton, IV et al. | EP | 0685204 | A1 | 12/1995 |
| 2011/0125176 | A1 | 5/2011 | Yates et al. | EP | 0364216 | B1 | 1/1996 |
| 2011/0125177 | A1 | 5/2011 | Yates et al. | EP | 0699418 | A1 | 3/1996 |
| 2011/0132962 | A1 | 6/2011 | Hall et al. | EP | 0702937 | A1 | 3/1996 |
| 2011/0132963 | A1 | 6/2011 | Giordano et al. | EP | 0705571 | A1 | 4/1996 |
| 2011/0132964 | A1 | 6/2011 | Weisenburgh, II et al. | EP | 0711611 | A2 | 5/1996 |
| 2011/0132965 | A1 | 6/2011 | Moore et al. | EP | 0484677 | B2 | 6/1996 |
| 2011/0139852 | A1 | 6/2011 | Zingman | EP | 0541987 | B1 | 7/1996 |
| 2011/0144430 | A1 | 6/2011 | Spivey et al. | EP | 0667119 | B1 | 7/1996 |
| 2011/0147433 | A1 | 6/2011 | Shelton, IV et al. | EP | 0708618 | B1 | 3/1997 |
| 2011/0147434 | A1 | 6/2011 | Hueil et al. | EP | 0770355 | A1 | 5/1997 |
| 2011/0155780 | A1 | 6/2011 | Boudreaux | EP | 0503662 | B1 | 6/1997 |
| 2011/0155781 | A1 | 6/2011 | Swensgard et al. | EP | 0447121 | B1 | 7/1997 |
| 2011/0155785 | A1 | 6/2011 | Laurent et al. | EP | 0625077 | B1 | 7/1997 |
| 2011/0155787 | A1 | 6/2011 | Baxter, III et al. | EP | 0633749 | B1 | 8/1997 |
| 2011/0163147 | A1 | 7/2011 | Laurent et al. | EP | 0710090 | B1 | 8/1997 |
| 2011/0174860 | A1 | 7/2011 | Shelton, IV et al. | EP | 0578425 | B1 | 9/1997 |
| 2011/0174863 | A1 | 7/2011 | Shelton, IV et al. | EP | 0625335 | B1 | 11/1997 |
| 2011/0192882 | A1 | 8/2011 | Hess et al. | EP | 0552423 | B1 | 1/1998 |
| 2011/0226837 | A1 | 9/2011 | Baxter, III et al. | EP | 0592244 | B1 | 1/1998 |
| 2011/0233258 | A1 | 9/2011 | Boudreaux | EP | 0648476 | B1 | 1/1998 |
| 2011/0253766 | A1 | 10/2011 | Baxter, III et al. | EP | 0649290 | B1 | 3/1998 |
| 2011/0288573 | A1 | 11/2011 | Yates et al. | EP | 0598618 | B1 | 9/1998 |
| 2011/0290851 | A1 | 12/2011 | Shelton, IV | EP | 0676173 | B1 | 9/1998 |
| 2011/0290853 | A1 | 12/2011 | Shelton, IV et al. | EP | 0678007 | B1 | 9/1998 |
| 2011/0290854 | A1 | 12/2011 | Timm et al. | EP | 0603472 | B1 | 11/1998 |
| 2011/0290855 | A1 | 12/2011 | Moore et al. | EP | 0605351 | B1 | 11/1998 |
| 2011/0290856 | A1 | 12/2011 | Shelton, IV et al. | EP | 0878169 | A1 | 11/1998 |
| 2011/0290857 | A1 | 12/2011 | Shelton, IV et al. | EP | 0879742 | A1 | 11/1998 |
| 2011/0295242 | A1 | 12/2011 | Spivey et al. | EP | 0695144 | B1 | 12/1998 |
| 2011/0295269 | A1 | 12/2011 | Swensgard et al. | EP | 0722296 | B1 | 12/1998 |
| 2011/0295270 | A1 | 12/2011 | Giordano et al. | EP | 0760230 | B1 | 2/1999 |
| 2011/0295295 | A1 | 12/2011 | Shelton, IV et al. | EP | 0623316 | B1 | 3/1999 |
| | | | | EP | 0650701 | B1 | 3/1999 |
| | FOREIGN PATENT DOCUMENTS | | | EP | 0537572 | B1 | 6/1999 |
| CA | 2512960 | A1 | 1/2006 | EP | 0923907 | A1 | 6/1999 |
| CA | 2514274 | A1 | 1/2006 | EP | 0843906 | B1 | 3/2000 |
| CN | 1868411 | A | 11/2006 | EP | 0552050 | B1 | 5/2000 |
| CN | 1915180 | A | 2/2007 | EP | 0833592 | B1 | 5/2000 |
| DE | 273689 | C | 5/1914 | EP | 0830094 | B1 | 9/2000 |
| DE | 1775926 | A | 1/1972 | EP | 1034747 | A1 | 9/2000 |
| DE | 3210466 | A1 | 9/1983 | EP | 1034748 | A1 | 9/2000 |
| DE | 9412228 | U | 9/1994 | EP | 0694290 | B1 | 11/2000 |
| DE | 19509116 | A1 | 9/1996 | EP | 1050278 | A1 | 11/2000 |
| DE | 19851291 | A1 | 1/2000 | EP | 1053719 | A1 | 11/2000 |
| DE | 19924311 | A1 | 11/2000 | EP | 1053720 | A1 | 11/2000 |
| DE | 69328576 | T2 | 1/2001 | EP | 1055399 | A1 | 11/2000 |
| DE | 10052679 | A1 | 5/2001 | EP | 1055400 | A1 | 11/2000 |
| DE | 20112837 | U1 | 10/2001 | EP | 1080694 | A1 | 3/2001 |

| | | | | | | | |
|---|---|---|---|---|---|---|---|
| EP | 1090592 | A1 | 4/2001 | EP | 1702567 | A2 | 9/2006 |
| EP | 1095627 | A1 | 5/2001 | EP | 1129665 | B1 | 11/2006 |
| EP | 1256318 | B1 | 5/2001 | EP | 1400206 | B1 | 11/2006 |
| EP | 0806914 | B1 | 9/2001 | EP | 1721568 | A1 | 11/2006 |
| EP | 0768840 | B1 | 12/2001 | EP | 1256317 | B1 | 12/2006 |
| EP | 0908152 | B1 | 1/2002 | EP | 1728473 | A1 | 12/2006 |
| EP | 0872213 | B1 | 5/2002 | EP | 1728475 | A2 | 12/2006 |
| EP | 0862386 | B1 | 6/2002 | EP | 1479346 | B1 | 1/2007 |
| EP | 0949886 | B1 | 9/2002 | EP | 1484024 | B1 | 1/2007 |
| EP | 1238634 | A2 | 9/2002 | EP | 1754445 | A2 | 2/2007 |
| EP | 0858295 | B1 | 12/2002 | EP | 1759812 | A1 | 3/2007 |
| EP | 0656188 | B1 | 1/2003 | EP | 1767163 | A1 | 3/2007 |
| EP | 1284120 | A1 | 2/2003 | EP | 1769756 | A1 | 4/2007 |
| EP | 1287788 | A1 | 2/2003 | EP | 1769758 | A1 | 4/2007 |
| EP | 0717966 | B1 | 4/2003 | EP | 1581128 | B1 | 5/2007 |
| EP | 0869742 | B1 | 5/2003 | EP | 1785097 | A2 | 5/2007 |
| EP | 0829235 | B1 | 6/2003 | EP | 1790293 | A2 | 5/2007 |
| EP | 0887046 | B1 | 7/2003 | EP | 1800610 | A1 | 6/2007 |
| EP | 0852480 | B1 | 8/2003 | EP | 1300117 | B1 | 8/2007 |
| EP | 0891154 | B1 | 9/2003 | EP | 1813199 | A1 | 8/2007 |
| EP | 0813843 | B1 | 10/2003 | EP | 1813201 | A1 | 8/2007 |
| EP | 0873089 | B1 | 10/2003 | EP | 1813203 | A2 | 8/2007 |
| EP | 0856326 | B1 | 11/2003 | EP | 1813207 | A1 | 8/2007 |
| EP | 1374788 | A1 | 1/2004 | EP | 1813209 | A1 | 8/2007 |
| EP | 0741996 | B1 | 2/2004 | EP | 1487359 | A1 | 10/2007 |
| EP | 0814712 | B1 | 2/2004 | EP | 1599146 | B1 | 10/2007 |
| EP | 1025807 | B1 | 2/2004 | EP | 1839596 | A1 | 10/2007 |
| EP | 1402837 | A1 | 3/2004 | EP | 1402821 | B1 | 12/2007 |
| EP | 0705570 | B1 | 4/2004 | EP | 1872727 | A1 | 1/2008 |
| EP | 0959784 | B1 | 4/2004 | EP | 1897502 | A1 | 3/2008 |
| EP | 1407719 | A2 | 4/2004 | EP | 1330201 | B1 | 6/2008 |
| EP | 1086713 | B1 | 5/2004 | EP | 1702568 | B1 | 7/2008 |
| EP | 0996378 | B1 | 6/2004 | EP | 1943976 | A2 | 7/2008 |
| EP | 1426012 | A1 | 6/2004 | EP | 1593337 | B1 | 8/2008 |
| EP | 0833593 | B2 | 7/2004 | EP | 1970014 | A1 | 9/2008 |
| EP | 1442694 | A1 | 8/2004 | EP | 1980213 | A2 | 10/2008 |
| EP | 0888749 | B1 | 9/2004 | EP | 1759645 | B1 | 11/2008 |
| EP | 0959786 | B1 | 9/2004 | EP | 1693008 | B1 | 12/2008 |
| EP | 1459695 | A1 | 9/2004 | EP | 1759640 | B1 | 12/2008 |
| EP | 1447119 | A1 | 11/2004 | EP | 2000102 | A2 | 12/2008 |
| EP | 1473819 | A1 | 11/2004 | EP | 1736104 | B1 | 3/2009 |
| EP | 1479345 | A1 | 11/2004 | EP | 1749486 | B1 | 3/2009 |
| EP | 1479347 | A1 | 11/2004 | EP | 1721576 | B1 | 4/2009 |
| EP | 1479348 | A1 | 11/2004 | EP | 1733686 | B1 | 4/2009 |
| EP | 0754437 | B2 | 12/2004 | EP | 1745748 | B1 | 8/2009 |
| EP | 1001710 | B1 | 1/2005 | EP | 2090256 | A2 | 8/2009 |
| EP | 1520521 | A1 | 4/2005 | EP | 1607050 | B1 | 12/2009 |
| EP | 1520523 | A1 | 4/2005 | EP | 1566150 | B1 | 4/2010 |
| EP | 1520525 | A1 | 4/2005 | EP | 1813206 | B1 | 4/2010 |
| EP | 1522264 | A1 | 4/2005 | EP | 1769754 | B1 | 6/2010 |
| EP | 1523942 | A2 | 4/2005 | EP | 1535565 | B1 | 10/2010 |
| EP | 1550408 | A1 | 7/2005 | EP | 1702570 | B1 | 10/2010 |
| EP | 1557129 | A1 | 7/2005 | EP | 1785098 | B1 | 10/2010 |
| EP | 1064883 | B1 | 8/2005 | FR | 999646 | A | 2/1952 |
| EP | 1067876 | B1 | 8/2005 | FR | 1112936 | A | 3/1956 |
| EP | 0870473 | B1 | 9/2005 | FR | 2765794 | A | 1/1999 |
| EP | 1157666 | B1 | 9/2005 | GB | 939929 | A | 10/1963 |
| EP | 0880338 | B1 | 10/2005 | GB | 1210522 | A | 10/1970 |
| EP | 1158917 | B1 | 11/2005 | GB | 1217159 | A | 12/1970 |
| EP | 1344498 | A1 | 11/2005 | GB | 1339394 | A | 12/1973 |
| EP | 1330989 | B1 | 12/2005 | GB | 2109241 | A | 6/1983 |
| EP | 0771176 | B2 | 1/2006 | GB | 2272159 | A | 5/1994 |
| EP | 1621138 | A2 | 2/2006 | GB | 2284242 | A | 5/1995 |
| EP | 1621139 | A2 | 2/2006 | GB | 2336214 | A | 10/1999 |
| EP | 1621141 | A2 | 2/2006 | GB | 2425903 | A | 11/2006 |
| EP | 1621145 | A2 | 2/2006 | JP | 6007357 | A | 1/1994 |
| EP | 1621151 | A2 | 2/2006 | JP | 7051273 | A | 2/1995 |
| EP | 1034746 | A1 | 3/2006 | JP | 8033641 | A | 2/1996 |
| EP | 1632191 | A2 | 3/2006 | JP | 8229050 | A | 9/1996 |
| EP | 1065981 | B1 | 5/2006 | JP | 2000033071 | A | 2/2000 |
| EP | 1082944 | B1 | 5/2006 | JP | 2000171730 | A | 6/2000 |
| EP | 1652481 | A2 | 5/2006 | JP | 2000287987 | A | 10/2000 |
| EP | 1382303 | B1 | 6/2006 | JP | 2000325303 | A | 11/2000 |
| EP | 1253866 | B1 | 7/2006 | JP | 2001286477 | A | 10/2001 |
| EP | 1032318 | B1 | 8/2006 | JP | 2002143078 | A | 5/2002 |
| EP | 1045672 | B1 | 8/2006 | JP | 2002369620 | A | 12/2002 |
| EP | 1617768 | B1 | 8/2006 | JP | 2005505322 | T | 2/2005 |
| EP | 1693015 | A2 | 8/2006 | JP | 2005103293 | A | 4/2005 |
| EP | 1400214 | B1 | 9/2006 | JP | 2005131163 | A | 5/2005 |

| | | | | | | | |
|---|---|---|---|---|---|---|---|
| JP | 2005131164 | A | 5/2005 | WO | WO 98/30153 | A1 | 7/1998 |
| JP | 2005131173 | A | 5/2005 | WO | WO 98/47436 | A1 | 10/1998 |
| JP | 2005131211 | A | 5/2005 | WO | WO 99/03407 | A1 | 1/1999 |
| JP | 2005131212 | A | 5/2005 | WO | WO 99/03408 | A1 | 1/1999 |
| JP | 2005137423 | A | 6/2005 | WO | WO 99/03409 | A1 | 1/1999 |
| JP | 2005152416 | A | 6/2005 | WO | WO 99/12483 | A1 | 3/1999 |
| JP | 2006-281405 | A | 10/2006 | WO | WO 99/12487 | A1 | 3/1999 |
| RU | 2187249 | C2 | 8/2002 | WO | WO 99/12488 | A1 | 3/1999 |
| RU | 2225170 | C2 | 3/2004 | WO | WO 99/15086 | A1 | 4/1999 |
| SU | 189517 | A | 1/1967 | WO | WO 99/15091 | A1 | 4/1999 |
| SU | 328636 | A | 9/1972 | WO | WO 99/23933 | A2 | 5/1999 |
| SU | 886900 | A1 | 12/1981 | WO | WO 99/23959 | A1 | 5/1999 |
| SU | 1333318 | A2 | 8/1987 | WO | WO 99/25261 | A1 | 5/1999 |
| SU | 1377053 | A1 | 2/1988 | WO | WO 99/29244 | A1 | 6/1999 |
| SU | 1561964 | A1 | 5/1990 | WO | WO 99/34744 | A1 | 7/1999 |
| SU | 1722476 | A1 | 3/1992 | WO | WO 99/45849 | A1 | 9/1999 |
| WO | WO 91/15157 | A1 | 10/1991 | WO | WO 99/48430 | A1 | 9/1999 |
| WO | WO 92/20295 | A1 | 11/1992 | WO | WO 99/51158 | A1 | 10/1999 |
| WO | WO 92/21300 | A1 | 12/1992 | WO | WO 00/24322 | A1 | 5/2000 |
| WO | WO 93/08755 | A1 | 5/1993 | WO | WO 00/24330 | A1 | 5/2000 |
| WO | WO 93/13718 | A1 | 7/1993 | WO | WO 00/41638 | A1 | 7/2000 |
| WO | WO 93/14690 | A1 | 8/1993 | WO | WO 00/48506 | A1 | 8/2000 |
| WO | WO 93/15648 | A1 | 8/1993 | WO | WO 00/53112 | A2 | 9/2000 |
| WO | WO 93/15850 | A1 | 8/1993 | WO | WO 00/54653 | A1 | 9/2000 |
| WO | WO 93/19681 | A1 | 10/1993 | WO | WO 00/57796 | A1 | 10/2000 |
| WO | WO 94/00060 | A1 | 1/1994 | WO | WO 00/64365 | A1 | 11/2000 |
| WO | WO 94/11057 | A1 | 5/1994 | WO | WO 00/72762 | A1 | 12/2000 |
| WO | WO 94/12108 | A1 | 6/1994 | WO | WO 00/72765 | A1 | 12/2000 |
| WO | WO 94/18893 | A1 | 9/1994 | WO | WO 01/03587 | A1 | 1/2001 |
| WO | WO 94/22378 | A1 | 10/1994 | WO | WO 01/05702 | A1 | 1/2001 |
| WO | WO 94/23659 | A1 | 10/1994 | WO | WO 01/10482 | A1 | 2/2001 |
| WO | WO 95/02369 | A1 | 1/1995 | WO | WO 01/35845 | A1 | 5/2001 |
| WO | WO 95/03743 | A1 | 2/1995 | WO | WO 01/54594 | A1 | 8/2001 |
| WO | WO 95/06817 | A1 | 3/1995 | WO | WO 01/58371 | A1 | 8/2001 |
| WO | WO 95/09576 | A1 | 4/1995 | WO | WO 01/62158 | A2 | 8/2001 |
| WO | WO 95/09577 | A1 | 4/1995 | WO | WO 01/62161 | A1 | 8/2001 |
| WO | WO 95/14436 | A1 | 6/1995 | WO | WO 01/62162 | A1 | 8/2001 |
| WO | WO 95/17855 | A1 | 7/1995 | WO | WO 01/62164 | A2 | 8/2001 |
| WO | WO 95/18383 | A1 | 7/1995 | WO | WO 01/62169 | A1 | 8/2001 |
| WO | WO 95/18572 | A1 | 7/1995 | WO | WO 01/78605 | A2 | 10/2001 |
| WO | WO 95/19739 | A1 | 7/1995 | WO | WO 01/91646 | A1 | 12/2001 |
| WO | WO 95/20360 | A1 | 8/1995 | WO | WO 02/07608 | A2 | 1/2002 |
| WO | WO 95/23557 | A1 | 9/1995 | WO | WO 02/07618 | A1 | 1/2002 |
| WO | WO 95/24865 | A1 | 9/1995 | WO | WO 02/17799 | A1 | 3/2002 |
| WO | WO 95/25471 | A3 | 9/1995 | WO | WO 02/19920 | A1 | 3/2002 |
| WO | WO 95/26562 | A1 | 10/1995 | WO | WO 02/19932 | A1 | 3/2002 |
| WO | WO 95/29639 | A1 | 11/1995 | WO | WO 02/30297 | A2 | 4/2002 |
| WO | WO 96/04858 | A1 | 2/1996 | WO | WO 02/32322 | A2 | 4/2002 |
| WO | WO 96/19151 | A1 | 6/1996 | WO | WO 02/36028 | A1 | 5/2002 |
| WO | WO 96/19152 | A1 | 6/1996 | WO | WO 02/43571 | A2 | 6/2002 |
| WO | WO 96/20652 | A1 | 7/1996 | WO | WO 02/058568 | A1 | 8/2002 |
| WO | WO 96/21119 | A1 | 7/1996 | WO | WO 02/060328 | A1 | 8/2002 |
| WO | WO 96/22055 | A1 | 7/1996 | WO | WO 02/067785 | A2 | 9/2002 |
| WO | WO 96/23448 | A1 | 8/1996 | WO | WO 02/098302 | A1 | 12/2002 |
| WO | WO 96/24301 | A1 | 8/1996 | WO | WO 03/000138 | A2 | 1/2003 |
| WO | WO 96/27337 | A1 | 9/1996 | WO | WO 03/001329 | A2 | 1/2003 |
| WO | WO 96/31155 | A1 | 10/1996 | WO | WO 03/013363 | A1 | 2/2003 |
| WO | WO 96/35464 | A1 | 11/1996 | WO | WO 03/015604 | A2 | 2/2003 |
| WO | WO 96/39085 | A1 | 12/1996 | WO | WO 03/020106 | A2 | 3/2003 |
| WO | WO 96/39086 | A1 | 12/1996 | WO | WO 03/020139 | A2 | 3/2003 |
| WO | WO 96/39087 | A1 | 12/1996 | WO | WO 03/024339 | A1 | 3/2003 |
| WO | WO 96/39088 | A1 | 12/1996 | WO | WO 03/079909 | A3 | 3/2003 |
| WO | WO 96/39089 | A1 | 12/1996 | WO | WO 03/030743 | A2 | 4/2003 |
| WO | WO 97/00646 | A1 | 1/1997 | WO | WO 03/037193 | A1 | 5/2003 |
| WO | WO 97/00647 | A1 | 1/1997 | WO | WO 03/047436 | A3 | 6/2003 |
| WO | WO 97/06582 | A1 | 2/1997 | WO | WO 03/055402 | A1 | 7/2003 |
| WO | WO 97/10763 | A1 | 3/1997 | WO | WO 03/057048 | A1 | 7/2003 |
| WO | WO 97/10764 | A1 | 3/1997 | WO | WO 03/057058 | A1 | 7/2003 |
| WO | WO 97/11648 | A2 | 4/1997 | WO | WO 03/063694 | A1 | 8/2003 |
| WO | WO 97/11649 | A1 | 4/1997 | WO | WO 03/077769 | A1 | 9/2003 |
| WO | WO 97/15237 | A1 | 5/1997 | WO | WO 03/079911 | A1 | 10/2003 |
| WO | WO 97/24073 | A1 | 7/1997 | WO | WO 03/082126 | A1 | 10/2003 |
| WO | WO 97/24993 | A1 | 7/1997 | WO | WO 03/088845 | A2 | 10/2003 |
| WO | WO 97/30644 | A1 | 8/1997 | WO | WO 03/090630 | A2 | 11/2003 |
| WO | WO 97/34533 | A1 | 9/1997 | WO | WO 03/094743 | A1 | 11/2003 |
| WO | WO 97/37598 | A1 | 10/1997 | WO | WO 03/094745 | A1 | 11/2003 |
| WO | WO 97/39688 | A2 | 10/1997 | WO | WO 03/094746 | A1 | 11/2003 |
| WO | WO 98/17180 | A1 | 4/1998 | WO | WO 03/094747 | A1 | 11/2003 |
| WO | WO 98/27880 | A1 | 7/1998 | WO | WO 03/101313 | A1 | 12/2003 |

| | | |
|---|---|---|
| WO | WO 03/105698 A2 | 12/2003 |
| WO | WO 03/105702 A2 | 12/2003 |
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115261 A2 | 12/2005 |
| WO | WO 2005/117735 A1 | 12/2005 |
| WO | WO 2005/122936 A1 | 12/2005 |
| WO | WO 2006027014 A1 * | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132092 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |
| WO | WO 2010/063795 A1 | 6/2010 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal.119040681/ abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.iwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print. cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

* cited by examiner

FIG. 8  FIRST HANDLE STROKE COMPRESSION

SHAFT BASED ROTARY DRIVE SYSTEM FOR SURGICAL INSTRUMENTS

CROSS-REFERENCE TO RELATED APPLICATIONS

This non-provisional patent application is a continuation patent application of and claims the benefit from U.S. patent application Ser. No. 11/810,015, filed Jun. 4, 2007, entitled "Surgical Instrument Having a Multiple Rate Directional Switching Mechanism", U.S. Patent Publication No. US 2008/0300613 A1, now U.S. Pat. No. 7,905,380 the entire disclosure of which is herein incorporated by reference and which is related to the following commonly-owned U.S. Patent Applications and which are hereby incorporated by reference in their entirety:

(1) U.S. patent application Ser. No. 11/810,016, entitled SURGICAL INSTRUMENT HAVING A DIRECTIONAL SWITCHING MECHANISM, now U.S. Pat. No. 7,832,408; and
(2) U.S. patent application Ser. No. 11/809,935, entitled SURGICAL INSTRUMENT HAVING A COMMON TRIGGER FOR ACTUATING AN END EFFECTOR CLOSING SYSTEM AND A STAPLE FIRING SYSTEM, now U.S. Pat. No. 7,819,299.

BACKGROUND

1. Field of the Invention

The present invention generally relates to surgical stapling instruments and, more particularly, to surgical staplers having an end effector closing system and a firing system for deploying staples.

2. Description of the Related Art

As known in the art, surgical staplers are often used to deploy staples into soft tissue to reduce or eliminate bleeding from the soft tissue, especially as the tissue is being transected, for example. Surgical staplers, such as an endocutter, for example, often comprise an end effector which is configured to secure the soft tissue between first and second jaw members. The first jaw member often includes a staple cartridge which is configured to removably store staples therein and the second jaw member often includes an anvil. In use, the staples are typically deployed from the staple cartridge by a driver which traverses a channel in the staple cartridge and causes the staples to be deformed against the anvil and secure layers of the soft tissue together. Often, as known in the art, the staples are deployed in several staple lines, or rows, in order to more reliably secure the layers of tissue together. The end effector may also include a cutting member, such as a knife, for example, which is advanced between two rows of the staples to resect the soft tissue after the layers of the soft tissue have been stapled together.

After the driver and the cutting member have been advanced within the end effector, it is often necessary to retract the driver and/or cutting member to their starting positions. Previous surgical staplers have included a return spring which retracts the cutting member relative to the staple cartridge after a release button or toggle switch on the surgical stapler has been actuated by the surgeon. Such staplers, however, are unable to partially retract the cutting member and, as a result, the cutting member must be fully retracted before it can be readvanced. Other previous surgical staplers have included a plurality of triggers which are operatively engaged with systems for closing a jaw member and for advancing and/or retracting the driver and cutting member. Such devices, while suitable for their intended purposes, often require a surgeon to release a trigger operably engaged with the closing system and reposition their hand to grasp a different trigger which is operatively engaged with a system for advancing the staple driver and cutting member. While previous surgical staplers have been developed which have a single trigger for both closing the jaw member and advancing the driver and cutting member, such devices perform both functions upon the initial actuation of the trigger. While suitable in some circumstances, devices which perform both functions in the same trigger actuation are often exceedingly difficult to operate owing to the high degree of force required to actuate the trigger. Furthermore, such devices, as they close the jaw member and deploy staples in the same trigger actuation, do not afford the surgeon with an opportunity to evaluate the position of the closed jaw member and reposition the jaw member before the staples are deployed into the soft tissue. What is needed is an improvement over the foregoing.

SUMMARY

In at least one form of the invention, a surgical instrument can include a switching mechanism which can allow a surgeon, or other clinician, to selectively advance or retract a staple driver and/or cutting member within a staple cartridge. In various embodiments, the surgical instrument can include a handle, a trigger operatively coupled to the handle, a firing drive, and an end effector. In at least one embodiment, the firing drive can include a first ratchet assembly configured to advance a cutting member in the end effector and a second ratchet assembly configured to retract the cutting member. In various embodiments, the trigger can include first and second pawls pivotably mounted thereon which are configured to be selectively engaged with the first and second ratchet assemblies, respectively. In at least one such embodiment, the trigger can be configured to slide between a first position in which the first pawl is engaged with the first ratchet assembly and a second position in which the second pawl is engaged with the second ratchet assembly. In such embodiments, a surgeon can quickly and conveniently select between advancing and retracting motions of the cutting member.

In at least one form of the invention, a surgical instrument can include a drive mechanism configured to advance a staple driver and/or cutting member at a first rate and retract the staple driver and/or cutting member at a different rate. In at least one embodiment, the rate at which the driver and cutting member are advanced and/or retracted is the distance that the driver and cutting member are translated per actuation, or stroke, of a trigger, for example. Accordingly, in such embodiments, a first rate is considered to be faster than a second rate if the trigger advances or retracts the cutting member a greater distance per actuation. In various embodiments, the cutting member can be retracted at a faster rate as compared to the rate in which it is advanced. In such embodiments, the surgical instrument can, owing to the slower advancing rate, provide a greater torque or advancing force to the cutting member while, owing to the faster retracting rate, reduce the time required for the surgeon to retract the cutting member. In various embodiments, as described above, the surgical instrument can include a switching mechanism configured to selectively engage one of a first drive system and a second drive system with a rotatable drive shaft. In at least one such embodiment, the first drive system can include a first gear having a first pitch radius and the second drive system can include a second gear having a different pitch radius where the first and second gears can rotate the drive shaft at different rates.

In at least one form of the invention, a surgical instrument can include a trigger which can be configured to close a jaw member onto soft tissue, for example, upon a first actuation of the trigger and advance a staple driver and/or cutting member upon a subsequent, or second, actuation of the trigger. In various embodiments, such a surgical instrument can allow a surgeon to position the surgical instrument in a surgical site and close the jaw member with an initial actuation of the trigger without deploying any staples into, or incising, the tissue. In such embodiments, as a result, the surgeon can manipulate the position of the surgical instrument and then actuate the trigger a second time to deploy staples into, and/or incise, the tissue. In at least one such embodiment, the first actuation of the trigger which closes the jaw member can also unlock a firing drive configured to advance the staple driver and cutting member during the second actuation of the trigger. In various embodiments, the surgical instrument can include a switching mechanism which can allow the surgeon to reopen the jaw member and, if they so choose, to reposition the jaw member in a more suitable position.

BRIEF DESCRIPTION OF THE DRAWINGS

The above-mentioned and other features and advantages of the various embodiments of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

In various embodiments, a surgical instrument in accordance with the present invention can include systems for inserting surgical staples into soft tissue, for example. In at least one embodiment, the surgical instrument can include a staple cartridge configured to removably store staples therein and an anvil for deforming the staples as they are deployed from the staple cartridge. In order to deploy the staples, the surgical instrument can include a staple driver configured to traverse the staple cartridge and a firing drive for advancing the staple driver within the staple cartridge. In various embodiments, the firing drive can include a drive bar which is translated in a substantially linear direction by a trigger operably engaged therewith. In other embodiments, the firing drive can include a drive shaft which is rotated by the trigger. In such embodiments, the surgical instrument can include a shaft assembly which can convert the rotary motion of the drive shaft into linear motion and translate the staple driver within the staple cartridge. While the exemplary embodiment illustrated in FIGS. 1-20 and described below includes a firing drive having a rotary drive shaft, the present invention is not so limited. Furthermore, while a general description of a firing drive having a rotary drive shaft is provided below, other such devices are described and illustrated in greater detail in the commonly-owned, co-pending U.S. patent application Ser. No. 11/475,412, entitled MANUALLY DRIVEN SURGICAL CUTTING AND FASTENING INSTRUMENT and filed on Jun. 27, 2006, the entire disclosure of which is hereby incorporated by reference herein.

Figure 1:
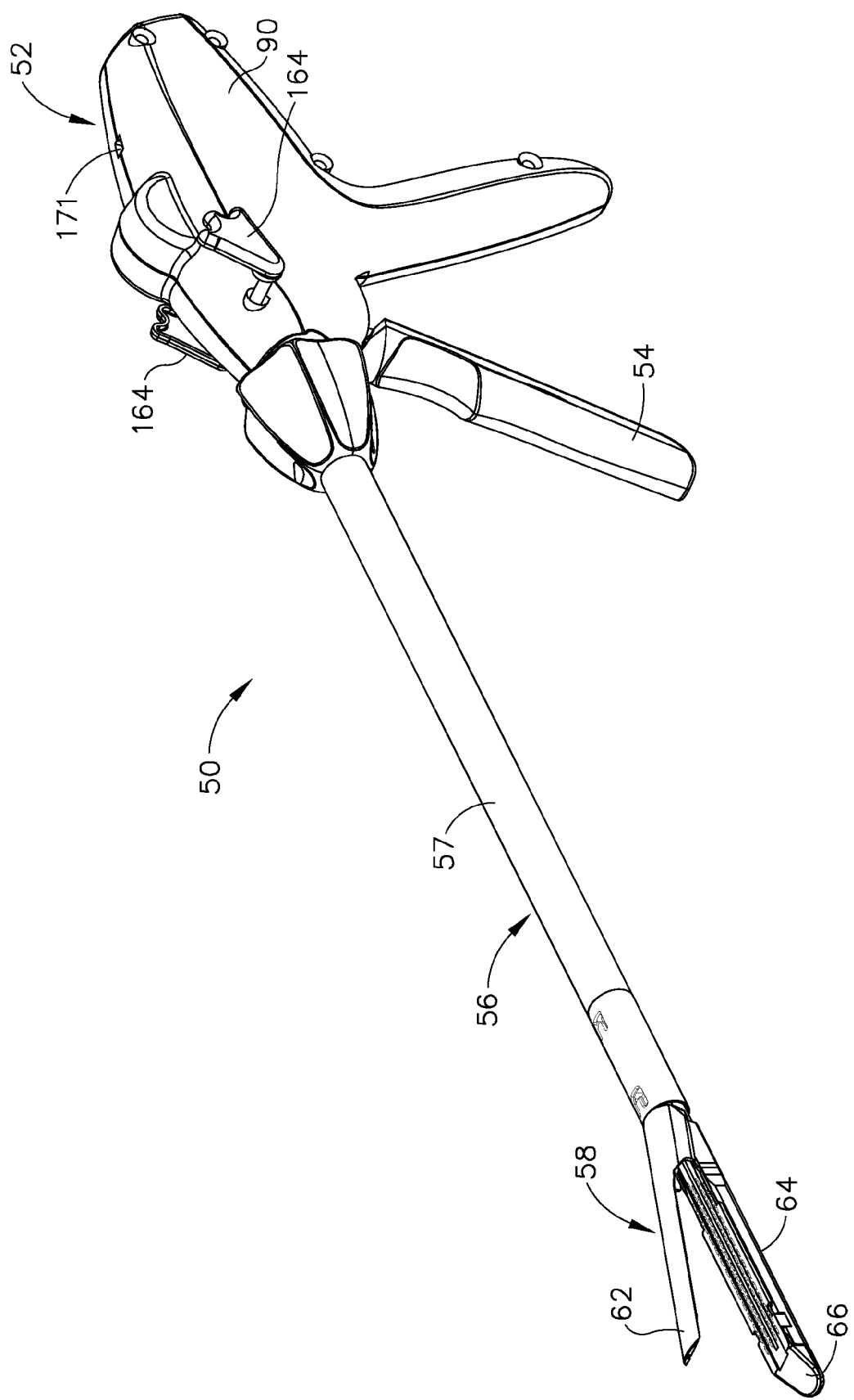
FIG. 1 is a perspective view of a surgical instrument in accordance with an embodiment of the present invention.
Figure 8:
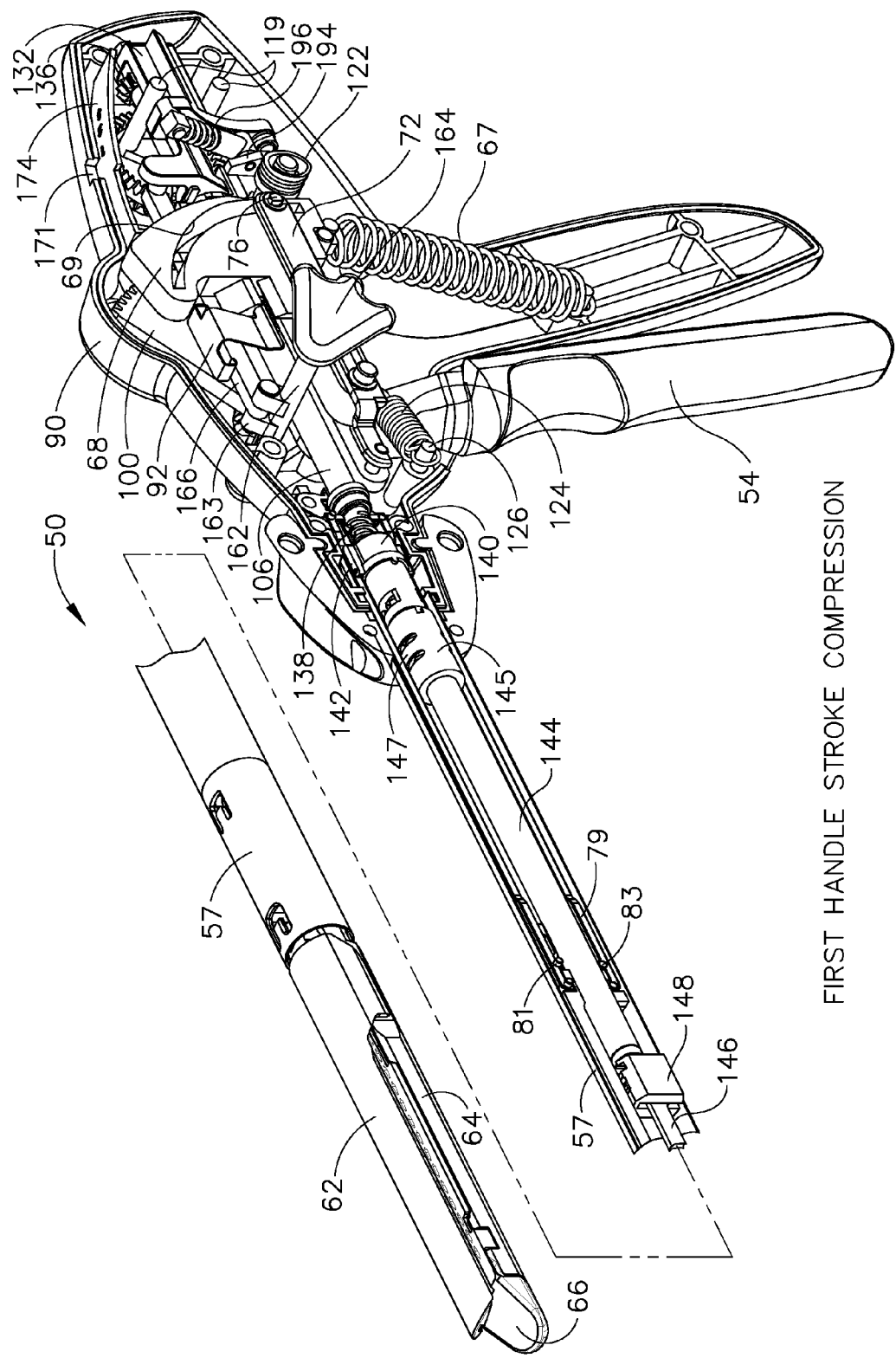
FIG. 8 is a perspective view of the surgical instrument of FIG. 1 illustrating the configuration of the surgical instrument upon the first actuation of the trigger.

Referring to FIG. 1, surgical instrument 50 can include handle portion 52, trigger 54, elongate shaft assembly 56, and end-effector 58. In various embodiments, end-effector 58 can include anvil 62 and staple cartridge channel 64, where channel 64 can be configured to receive staple cartridge 66 and anvil 62 can be pivotably connected to channel 64. In at least one embodiment, at least one of anvil 62 and channel 64 can be operably connected to trigger 54 such that, upon an actuation of trigger 54, anvil 62 can be rotated into a closed position as illustrated in FIG. 8. In various embodiments, referring to FIGS. 2-4, trigger 54 can be operably engaged with a closure drive system configured to translate both anvil 62 and channel 64 relative to outer sheath 57 of elongate shaft assembly 56. Referring primarily to FIG. 4, the closure drive can include cam 68 operably engaged with trigger 54 such that a first actuation of trigger 54 can rotate cam 68 about pin 70 and drive closure links 72 in a substantially linear direction. More particularly, trigger 54 can include lift pin 55 (FIG. 3) extending therefrom which can be configured to contact surface 71 of cam 68 and lift cam 68 into the position illustrated in FIG. 8. Cam 68 can further include cam slot 69 where, when cam 68 is rotated from its position illustrated in FIG. 4 to its position illustrated in FIG. 8, the side walls of cam slot 69 can engage closure link pin 76 and, in the present embodiment, slide closure links 72 in a direction illustrated by arrow A (FIG. 4).

Figure 2:
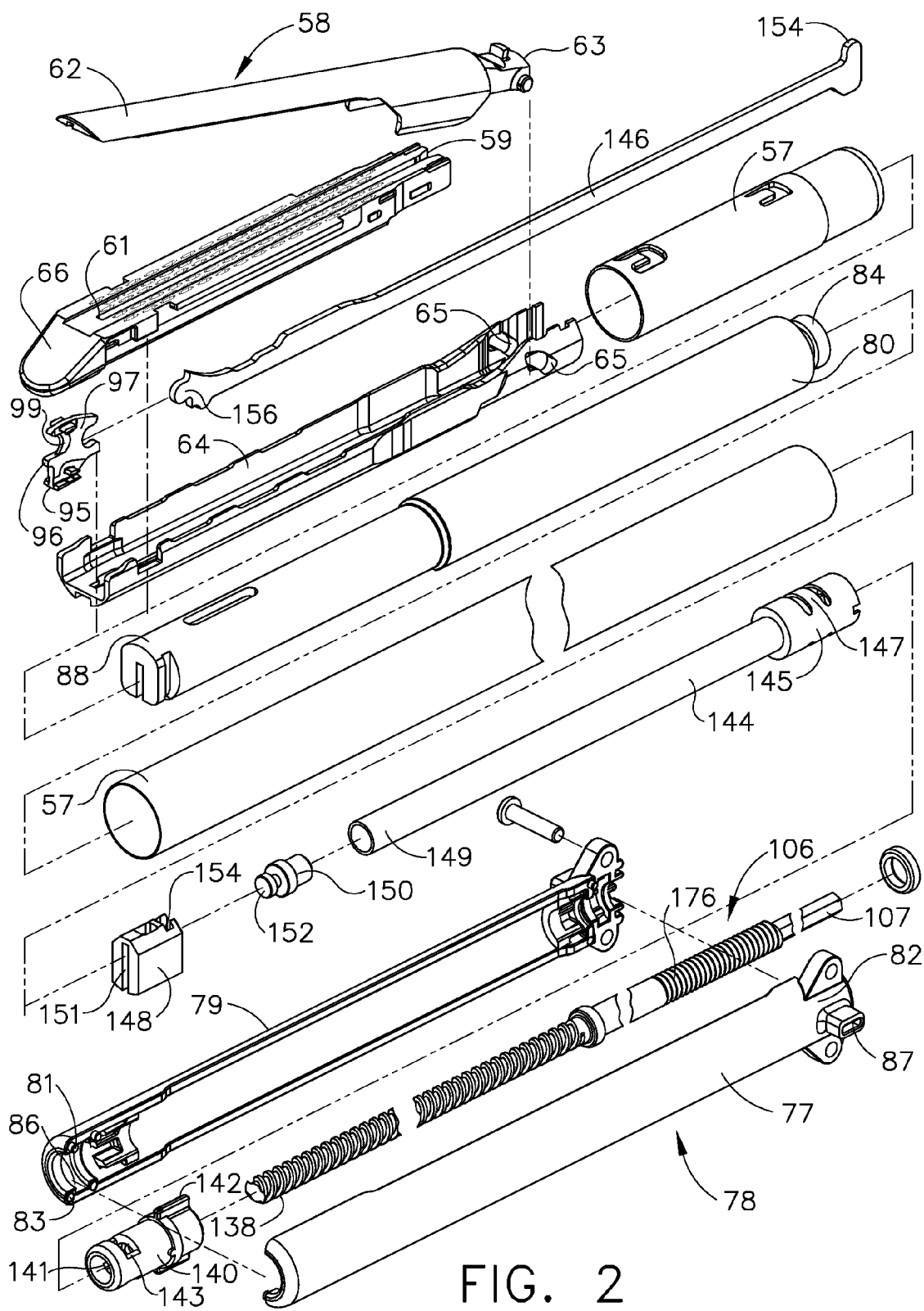
FIG. 2 is an exploded view of a shaft portion and end effector of the surgical instrument of FIG. 1.

Referring to FIGS. 2 and 4, surgical instrument 50 can further include a spine assembly within elongate shaft assembly 56 (FIG. 1), where the spine assembly can include proximal channel portion 78 and distal channel portion 80. In various embodiments, channel portions 78 and 80 can be interconnected by the cooperative engagement of projection, or tongue, 84 and groove 86. More particularly, referring to FIG. 2, proximal channel portion 78 can include, in various embodiments, first half 77 and second half 79 which can be assembled to distal channel portion 80 such that projection 84 is secured within groove 86. In at least one embodiment, proximal channel portion halves 77 and 79 can include projections 81 and/or apertures 83 configured to provide a snap-fit or press-fit engagement between proximal channel portion halves 77 and 79. In various other embodiments, channel portions 78 and 80 can be interconnected by any suitable means and, in at least one embodiment, although not illustrated, portions 78 and 80 can be integrally formed. Similar to the above, referring to FIG. 2, distal channel portion 80 can include distal end 88 which can be connected to staple cartridge channel 64. More particularly, distal channel portion 80 and staple cartridge channel 64 can include cooperating tongue and groove features, for example, which can provide a press-fit or snap-fit interconnection therebetween, although any other suitable interconnection therebetween can be used.

Referring to FIG. 4, proximal end 82 of channel portion 78 can be coupled to closure links 72 by pin 53 such that, when closures links 72 are translated by cam 68, channel portion 78 is translated within elongate shaft assembly 56. In at least one embodiment, channel portion 78 can further include projections 87 extending therefrom which can be configured to slide within recesses 85 (FIG. 3) in housing portions 90 and substantially limit the translation of channel portion 78 along an axis. As staple cartridge channel 64 is connected to proximal channel portion 78 via distal channel portion 80, channel 64, and anvil 62 pivotably connected thereto, can be moved in direction A when cam 68 is rotated by trigger 54 as described above. In at least one embodiment, referring to FIG. 2, proximal end 63 of anvil 62 can be configured to abut outer sheath 57 of elongate shaft assembly 56 when channel 64 and anvil 62 are translated relative to sheath 57. After proximal end 63 of anvil 62 contacts outer sheath 57, anvil 62 can be configured to rotate toward channel 64 and staple cartridge 66 in order to close anvil 62 as illustrated in FIG. 8. In various embodiments, referring to FIG. 2, channel 64 can include slots 65 therein which can be configured to guide anvil 62 as it is pivoted relative to channel 64. Once anvil 62 is closed, the surgical instrument can further include a lock which holds anvil 62 in its closed position. In various embodiments, referring to FIGS. 9-11, surgical instrument 50 can include spring lock 92 mounted to housing 90, where spring lock 92 can be configured to releasably hold cam 68 in position which, as a result, locks closure links 72, channel portions 78 and 80, channel 64, and anvil 62 in position until a surgeon desires to open anvil 62 as described in detail further below.

In various embodiments, after anvil 62 has been placed into its closed position, trigger 54 can be actuated a second time to operate a firing drive which advances cutting member 96 within end effector 58. In at least one embodiment, the firing drive can be disengaged from trigger 54 prior to the first actuation of trigger 54. In such embodiments, the first actuation of trigger 54 can operably engage trigger 54 with the firing drive and/or release a component of the firing drive such that the firing drive becomes operably engaged with trigger 54. In the illustrated embodiment, referring to FIGS. 3 and 4, the firing drive can include trigger gear portion 100 extending from trigger 54, gear train 102, gear carriage 130, and rotatable drive shaft 106 which can be configured to advance cutting member 96 within end effector 58 as described in greater detail below. As illustrated in FIGS. 3-7, gear train 102 can include ratchet gear 108, main drive gear 110, bevel drive gear 112, and bevel gear 114 where, prior to the first actuation of trigger 54, cam 68 can be configured to bias ratchet gear 108 out of engagement with main drive gear 110. More particularly, referring to FIG. 3, ratchet gear 108 can include shaft 116 and collar 118 where cam 68 can be configured to contact collar 118 and bias ratchet gear 108 away from main drive gear 112 such that ratchet face 109 on ratchet gear 108 is not engaged with ratchet face 111 on main drive gear 110.

Upon the first actuation of trigger 54, as described above, cam 68 can be rotated into the position illustrated in FIG. 8 and, as a result of such rotation, groove 120 (FIGS. 4 and 5) in cam 68 can be configured to release ratchet gear 108. More particularly, referring to FIGS. 5-7, groove 120 can be dimensioned such that, when the rotation of cam 68 aligns groove 120 with collar 118, collar 118 can slide past cam 68 and allow ratchet spring 122 to bias ratchet gear 108 into operative engagement with main drive gear 110. Thereafter, trigger 54 can be released and then returned to its starting position by trigger spring 124 where trigger spring 124 can be connected to pin 126 extending from housing 90 and pin 128 extending from trigger 54. Notably, eventhough trigger 54 can be returned to its starting position, cam 68 can remain locked in its second position by lock 92, as described above, thereby maintaining the alignment between groove 120 and collar 118. With ratchet gear 108 now operably engaged with drive gear 110, a second actuation of trigger 54 can advance cutting member 96 and the staple driver within end effector 58.

Figure 3:
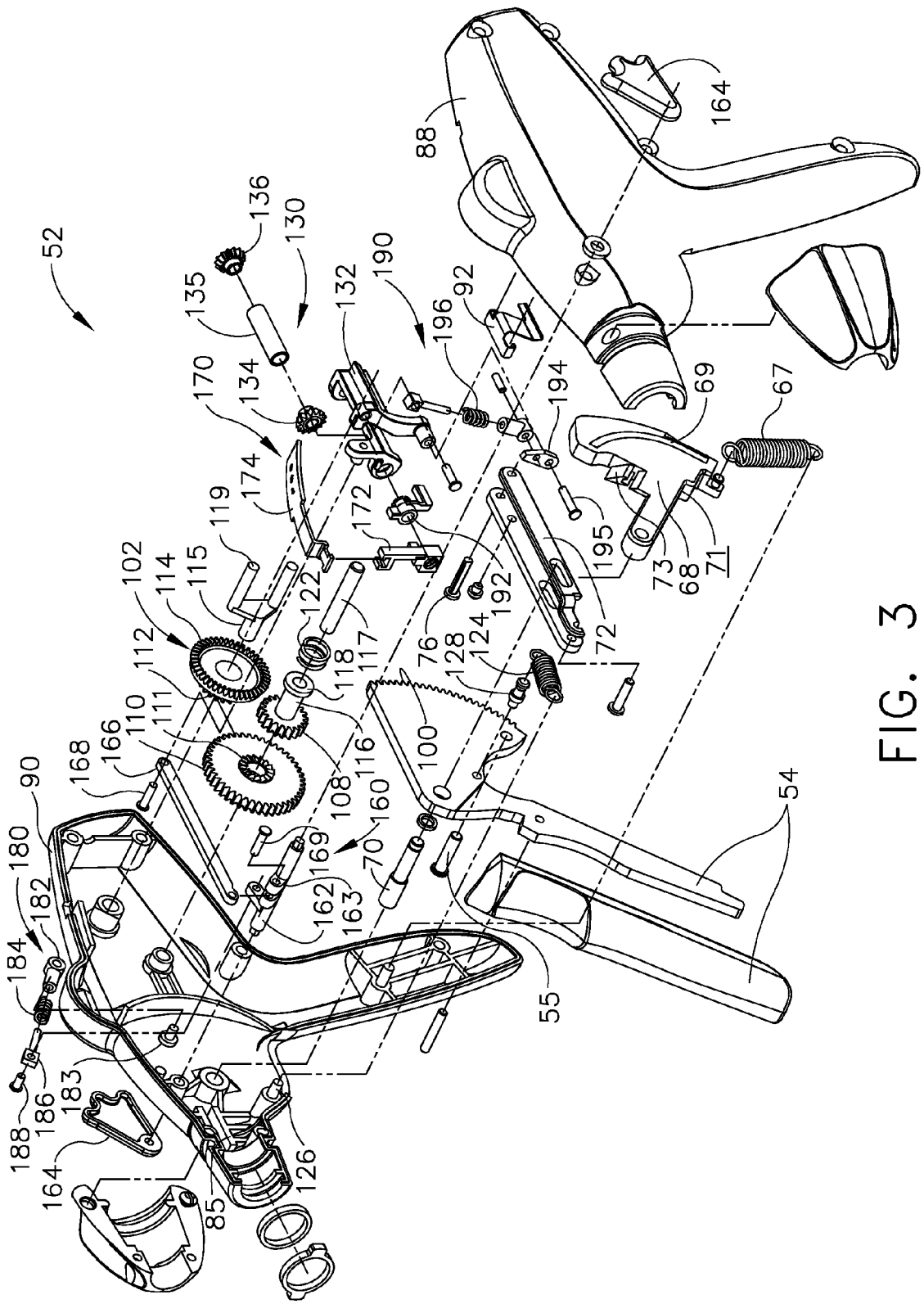
FIG. 3 is an exploded view of a handle portion of the surgical instrument of FIG. 1.
Figure 4:
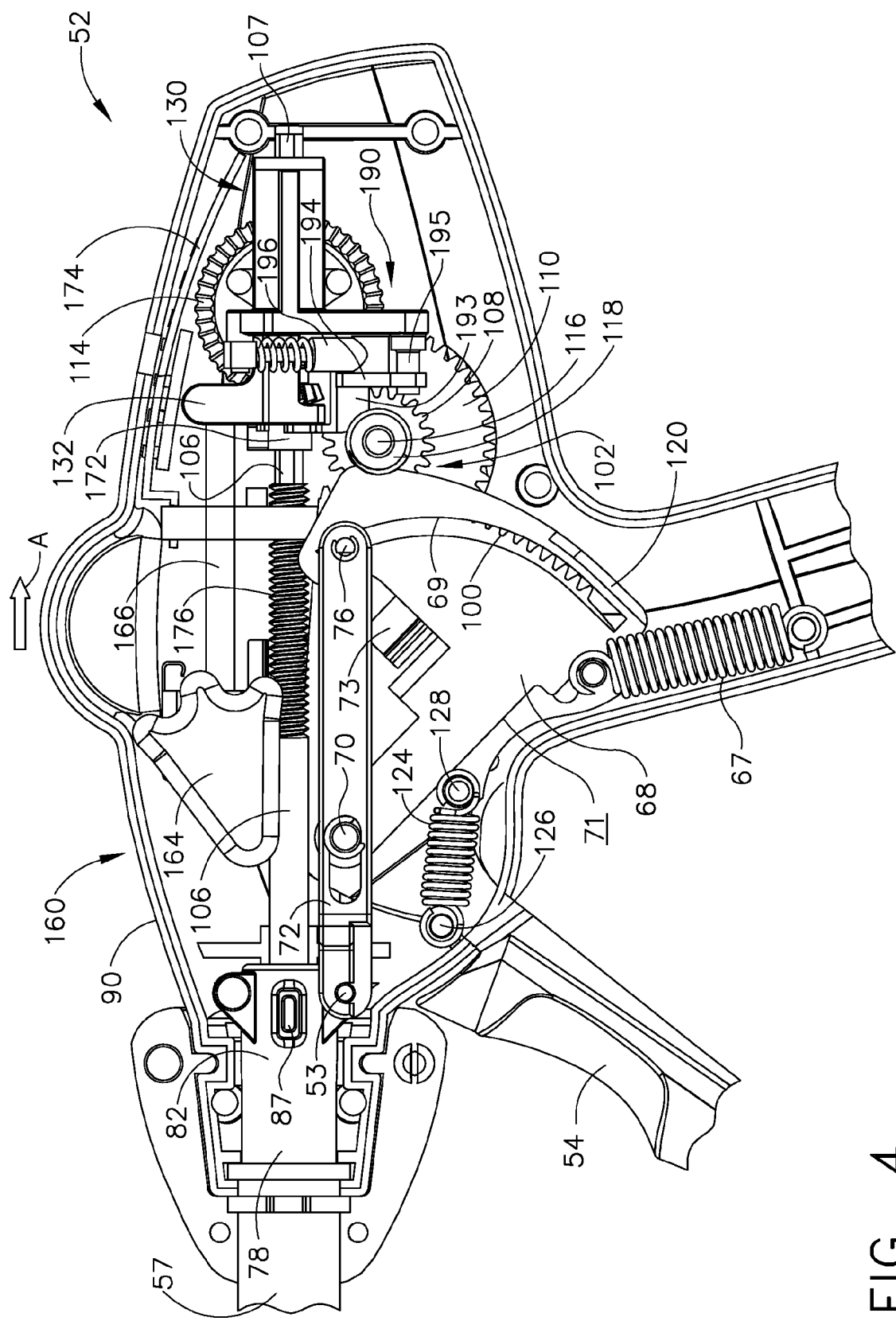
FIG. 4 is partial side view of the handle portion of FIG. 3 with some components of the surgical instrument removed.

Referring primarily to FIGS. 3 and 4, an actuation of trigger 54 can rotate trigger gear portion 100 about an axis defined by pin 70. Trigger gear portion 100 can include gear teeth extending along the perimeter thereof which can, referring to FIGS. 5 and 6, be engaged with gear teeth extending around the circumference, for example, of ratchet gear 108. In use, as a result, the actuation, or rotation, of trigger 54 can rotate ratchet gear 108 about an axis defined by shaft 116 and pin 117 (FIG. 3). As described above, ratchet gear 108 can, referring to FIGS. 5 and 6, include ratchet face 109 which can be configured to engage ratchet face 111 of main drive gear 110. In at least one embodiment, ratchet faces 109 and 111 can be configured to transmit the rotational motion of trigger 54 to main drive gear 110 upon the second actuation, or other subsequent actuation, of trigger 54 but also permit relative sliding movement therebetween when trigger 54 is released and returned to its unactuated position. In effect, ratchet faces 109 and 111 can be configured to transmit rotational motion to main drive gear 110 when ratchet gear 108 is rotated in one direction but not transmit rotational motion to main drive gear 110 when ratchet gear 108 is rotated in the opposite direction. Although a ratchet mechanism has been described and illustrated herein, any other suitable mechanism for transmitting motion between trigger 54 and main drive gear 110 can be used. Furthermore, although trigger 54 has been described and illustrated as a lever, any other suitable device can be used to motivate the firing and closing drives described herein.

Figure 5:
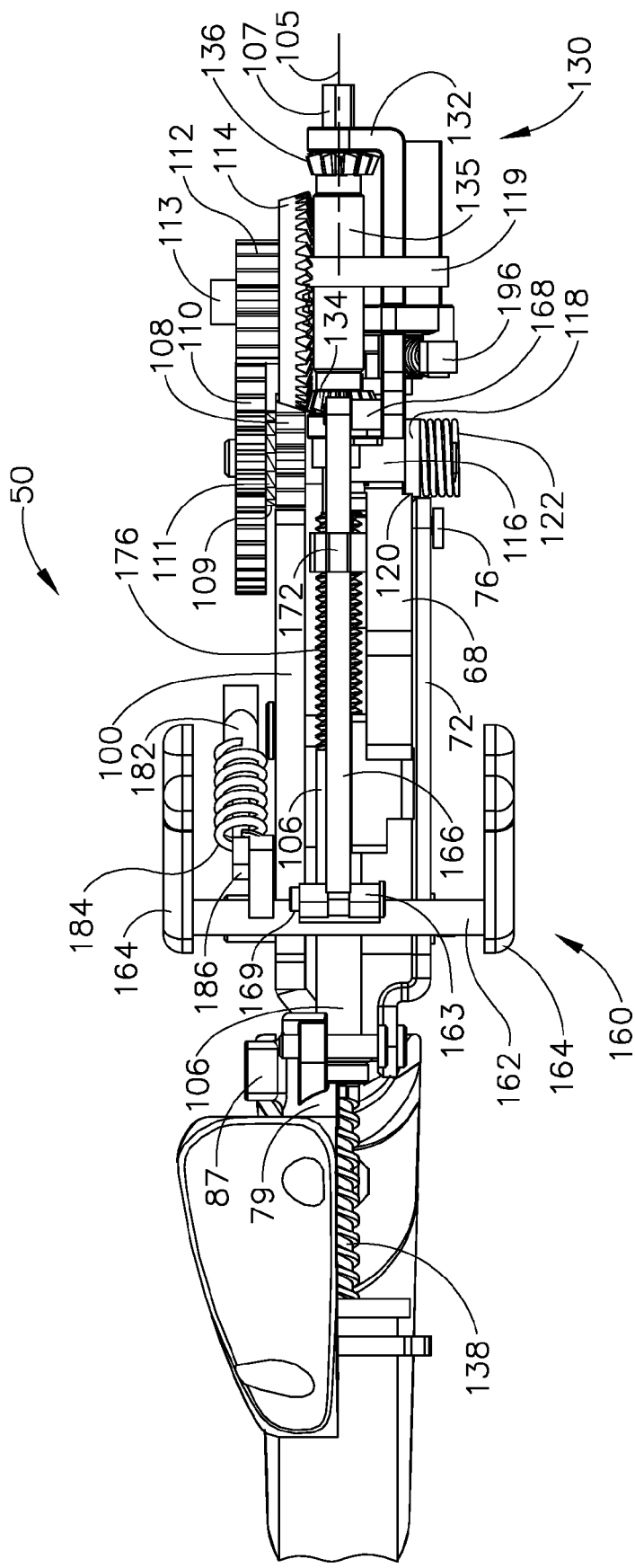
FIG. 5 is a top view of the handle portion of FIG. 3 with some components of the surgical instrument removed illustrating the surgical instrument in a configuration for advancing a cutting member in the end effector.
Figure 6:
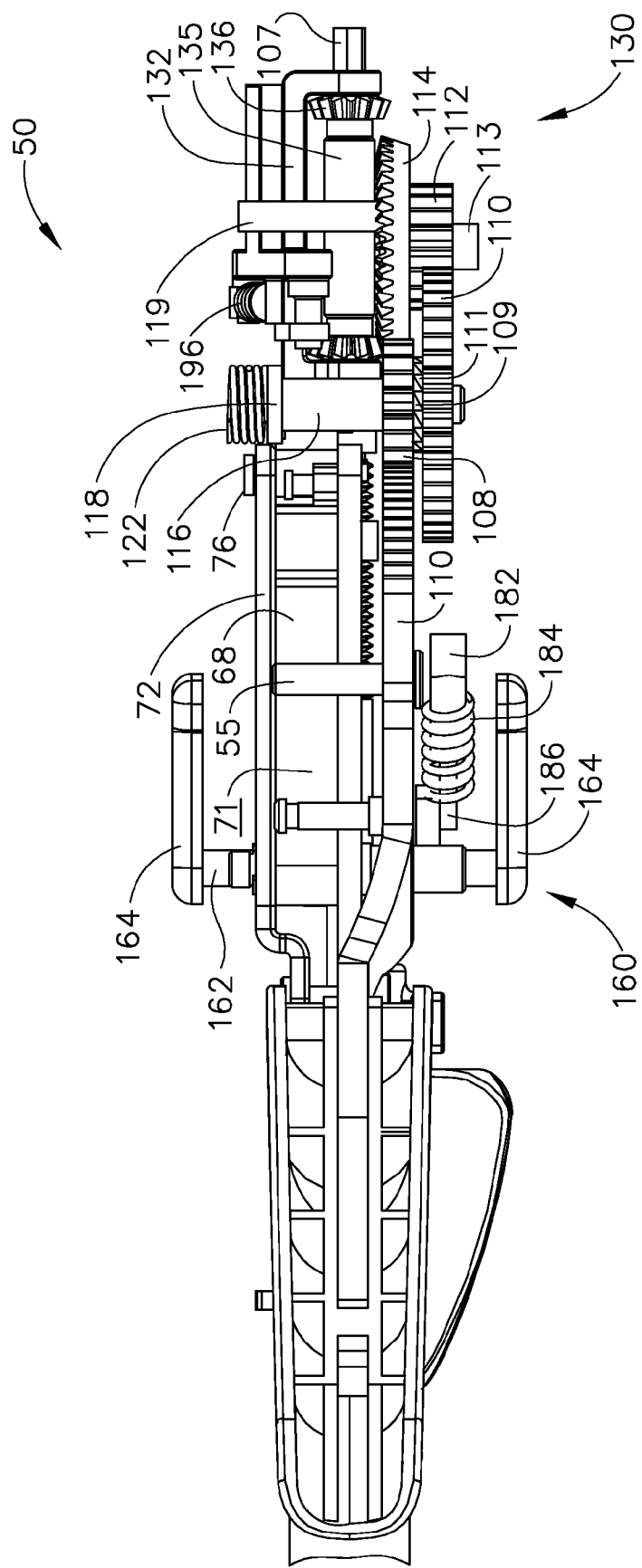
FIG. 6 is a bottom view of the handle portion of FIG. 3 with some components of the surgical instrument removed illustrating the surgical instrument in a configuration for advancing a cutting member in the end effector.
Figure 7:
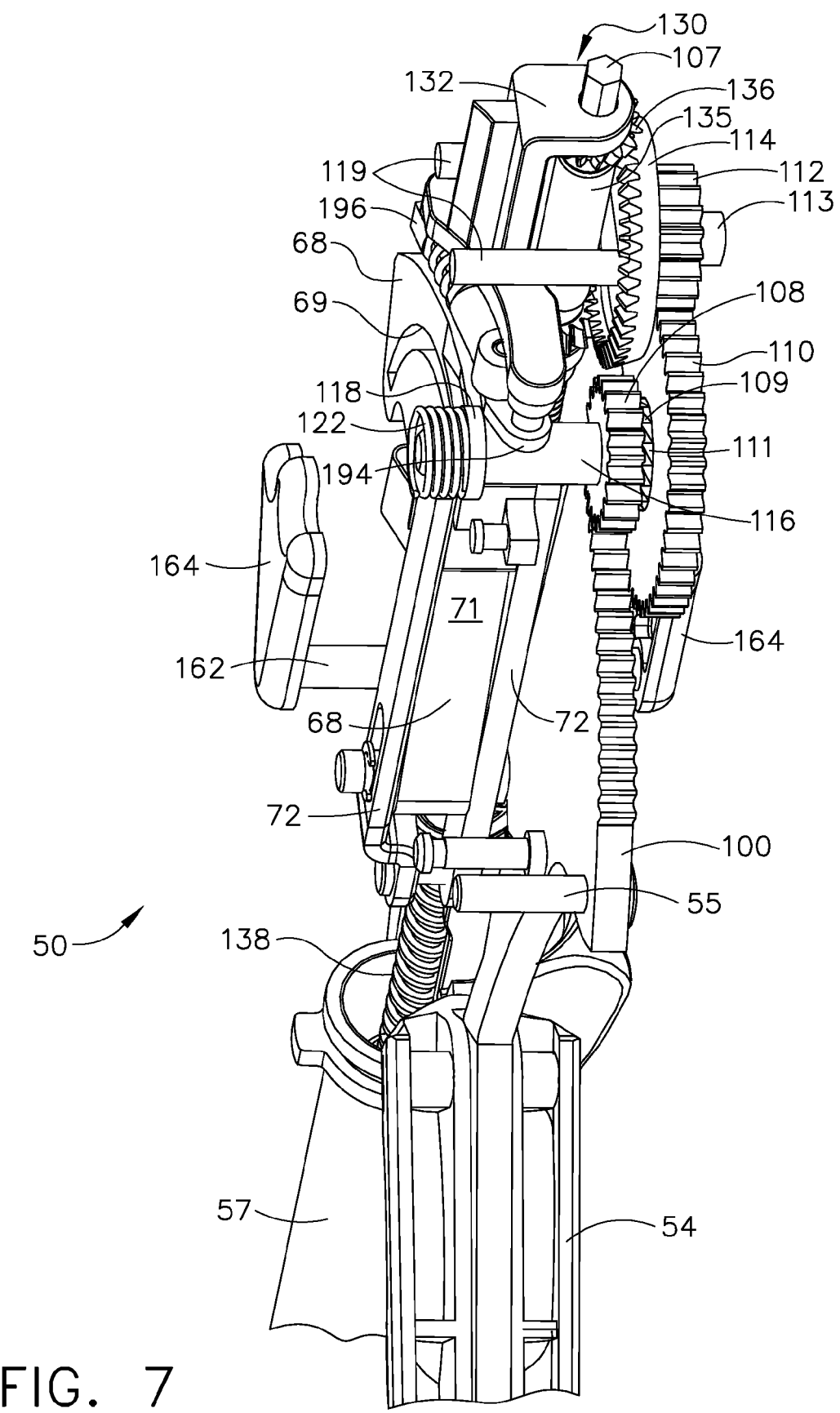
FIG. 7 is a partial perspective view of the handle portion of FIG. 3 with some components of the surgical instrument removed.

Referring primarily to FIGS. 5-7, main drive gear 110 can include gear teeth extending around the circumference thereof, for example, which can be engaged with gear teeth extending around the perimeter, for example, of bevel drive gear 112. In use, as a result, the rotational motion transmitted to main drive gear 110 from ratchet gear 108, for example, can be transmitted to bevel drive gear 112. In various embodiments, bevel drive gear 112 can be mounted to or integrally formed with shaft 113, where shaft 113 can define an axis about which bevel drive gear 112 can be rotated. In at least one embodiment, referring to FIG. 3, surgical instrument 50 can further include bracket 115 about which bevel drive gear 112 and shaft 113 can be rotated. As described in greater detail below, bracket 115 can also include supports 119 which can be configured to slidably support at least a portion of gear carriage 130. In various embodiments, referring to FIGS. 5-7, bevel gear 114 can be attached to bevel drive gear 112 or, alternatively, bevel gear 114 can be mounted to or integrally formed with shaft 113. In either event, the rotational motion transmitted to bevel drive gear 112 can be transmitted to bevel gear 114.

In various embodiments, although not illustrated, bevel gear 114 could be directly engaged with drive shaft 106 via cooperating bevel gear teeth. In at least one such embodiment, bevel gear 114 could rotate drive shaft 106 in a clockwise direction, for example, and advance cutting member 96 within end effector 58 as described below. In such embodiments, the actuation of trigger 54 could advance cutting member 96 within end effector 58, however, cutting member 96 would have to be retracted either manually or via an additional retraction system. In the illustrated embodiment of the present invention, referring to FIGS. 3 and 5-7, surgical instrument 50 can further include a switching mechanism which can allow drive shaft 106 to be rotated in either a clockwise or counter-clockwise direction and, correspondingly, allow cutting member 96 to be advanced or retracted via the actuation of trigger 54. In various embodiments, referring primarily to FIGS. 5 and 6, the switching mechanism can include gear carriage 130 which can be shifted between a first position in which the rotational motion of bevel gear 114 rotates drive shaft 106 in a clockwise direction, for example, and a second position in which the rotational motion of bevel gear 114 rotates drive shaft 106 in a counter-clockwise direction.

In various embodiments, referring to FIGS. 5-7, gear carriage 130 can include housing 132, forward gear 134, and reversing gear 136 where forward gear 134 and reversing gear 136 can be rotatably mounted to housing 132. In at least one embodiment, drive shaft 106 can include substantially hex-shaped end 107, for example, which can be received within apertures (not illustrated) in forward gear 134 and reversing gear 136 such that gears 134 and 134 are rotatably engaged with drive shaft 106. In other various embodiments, end 107 can include any other suitable shape or configuration such that gears 134 and 136 are rotatably engaged with drive shaft 106. In either event, referring to FIG. 5, gear carriage 130 can be slid along end 107 such that either forward gear 134 or reversing gear 136 can be engaged with bevel gear 114. In use, when forward gear 134 is engaged with bevel gear 114, for example, the rotational motion of bevel gear 114 can be transmitted to forward gear 134 and, owing to cooperating geometries of end 107 and the aperture in forward gear 134, the rotational motion of gear 134 can be transmitted to drive shaft 106. In order to rotate drive shaft in the opposite direction, gear carriage 130 can be slid proximally, or rearward, such that reversing gear 136 engages bevel gear 114. A mechanism for motivating gear carriage 130 in this manner is described further below.

In various embodiments, when forward gear 134 is engaged with bevel gear 114, as illustrated in FIG. 5, reversing gear 136 can be disengaged from bevel gear 114 such that reversing gear 136 is free to rotate with drive shaft 106. In at least one embodiment, gear carriage 130 can further include spacer 135 which can be configured to rotatably support and align gears 134 and 136 yet permit gears 134 and 136 to rotate independent of one another. In some embodiments, gear carriage 130 can be placed in a position intermediate the forward and rearward positions such that both gears 134 and 136 engage bevel gear 114 and hold drive shaft 106 in a 'locked-out' condition such that trigger 54 cannot be actuated. In other various embodiments, gear carriage 130 can be placed in an intermediate position such that neither gears 134 and 136 engage bevel gear 114. In such embodiments, the firing drive is in a 'free' condition and the rotational motion of bevel gear 114 is not transmitted to drive shaft 106.

In various embodiments, referring primarily to FIG. 2, drive shaft 106 can further include threaded drive portion 138 which can be operably engaged with firing nut 140. In at least one embodiment, threaded drive portion 138 can be configured to slidably advance and/or retract firing nut 140 in response to rotational motion of drive shaft 106. More particularly, firing nut 140 can include threaded aperture 141 which can be configured to threadably receive threaded drive portion 138 such that the rotation of drive shaft 106 produces a rectional force which advances firing nut 140 distally. In at least one embodiment, firing nut 140 can include projection 142 extending therefrom which can be configured to extend through a slot defined between proximal channel portion halves 77 and 79 in order to constrain the movement of firing nut 140 along an axis. In effect, the slot can prevent firing nut 140 from rotating with drive shaft 106 and can define a path for projection 142 as firing nut 140 is translated within channel portion 78.

In various embodiments, referring to FIG. 2, cutting member 96 can be operably engaged with firing nut 140 such that the translation of firing nut 140, as described above, can result in the translation of cutting member 96 within end effector 58. In at least one embodiment, surgical instrument 50 can further include firing rod 144 connected to firing nut 140, drive bar 146 connected to cutting member 96, and adapter 148 configured to connect drive bar 146 to firing rod 144. In various embodiments, firing rod 144 can include proximal end 145 which can include an aperture configured to receive at least a portion of firing nut 140 in a press-fit manner. In at least one embodiment, proximal end 145 of firing rod 144 can include deformable member 147 which can be configured to engage recess 143 in firing nut 140 after deformable member 147 has been depressed or deformed inwardly toward recess 143. In either event, firing rod 144 can further include distal end 149 which can be configured to receive plug 150 in a press-fit manner, for example, where plug 150 can include projection 152 extending therefrom which can be received within slot 154 in adapter 148. In various embodiments, adapter 148 can further include slot 151, where slot 151 can be configured to receive connector tab 154 of drive bar 146 such that, when adapter 148 is translated by firing rod 144, drive bar 146 can be translated within distal retainer section 80. In at least one embodiment, drive bar 146 can further include distal end 156 which can be configured to engage recess 97 in cutting member 96 and advance and/or retract cutting member 96 within end effector 58. As described above, cutting member 96 can include knife 99 which can be configured to incise tissue positioned between anvil 62 and staple cartridge 66 as cutting member 96 is advanced within end effector 58. Further, as described above, cutting member 96 can include portion 95, where portion 95 can be configured to push a staple driver (not illustrated) within staple cartridge 66 to deploy staples (not illustrated) removably stored therein.

In various embodiments, the surgical instrument can be configured to advance cutting member 96 a desired distance upon a single actuation of trigger 54, i.e., the second overall actuation of trigger 54 in embodiments where the first actuation of trigger 54 closes anvil 62 as described above. In other embodiments, however, more than one actuation of trigger 54 can be used to advance cutting member 96 a desired distance. In at least one such embodiment, referring to FIGS. 12-16, trigger 54 can be actuated three times to advance cutting member 96 from proximal end 59 to distal end 61 of end effector 58. The quantity of such actuations in other embodiments, however, will depend largely upon the overall distance that cutting member 96 is to be displaced and the displacement of cutting member 96 as a result of each actuation. Notably, prior to the second actuation of trigger 54, cutting member 96 can be positioned in proximal end 59 of end effector 58 and firing nut 140 can be positioned in its most proximal position. Upon the second actuation of trigger 54, referring to FIGS. 13 and 14, cutting member 96 can be advanced approximately one-third of the distance between proximal end 59 and distal end 61 and, similarly, firing nut 140 can be advanced distally along drive shaft 106. Thereafter, referring to FIG. 15, cutting member can be advanced an additional one-third of the distance between proximal end 59 and distal end 61 upon the third actuation of trigger 54 and, similarly, referring to FIG. 16, cutting member 96 can be advanced into distal end 61 of end effector 58 upon the fourth actuation of trigger 54.

In various embodiments, in order to assist a surgeon in monitoring the amount of times that trigger 54 has been actuated, surgical instrument 50 can include a counting mechanism which can be configured to display the amount of times that trigger 54 has been actuated and/or the amount of actuations remaining to deploy all of the staples in the staple cartridge. In either event, referring primarily to FIGS. 3 and 9, one embodiment of counting mechanism 170 can include indicator nut 172, indicator plate 174, and indictor window 171 (FIG. 1) in housing 90. In at least one embodiment, indicator plate 174 can include indicia thereon which can communicate to the surgeon the amount of times that trigger 54 has been actuated to advance cutting member 96. In such embodiments, indicator plate 174 can include blank portion 173 which is visible through window 171 before and after the first actuation of trigger 54, i.e., the actuation of trigger 54 which closes anvil 62 as described above. Upon the second actuation of trigger 54, the rotation of drive shaft 106 can advance indicator nut 172 and indicator plate 174, which is mounted to indicator nut 172, distally such that the numeral "1" or other appropriate indicia on indicator plate 174 can be seen through indicator window 171. Accordingly, such an indicium can indicate to the surgeon that cutting member 96 has been advanced by one actuation of trigger 54. Similar to firing nut 140, indicator nut 172 can include a threaded aperture which can be threadably engaged with threaded portion 176 of drive shaft 106 such that the rotation of drive shaft 106 applies a rectional force to indicator nut 172 and advances it distally. Subsequent actuations of trigger 54 can move the numerals '2' and '3' beneath indicator window 171.

Figure 17:
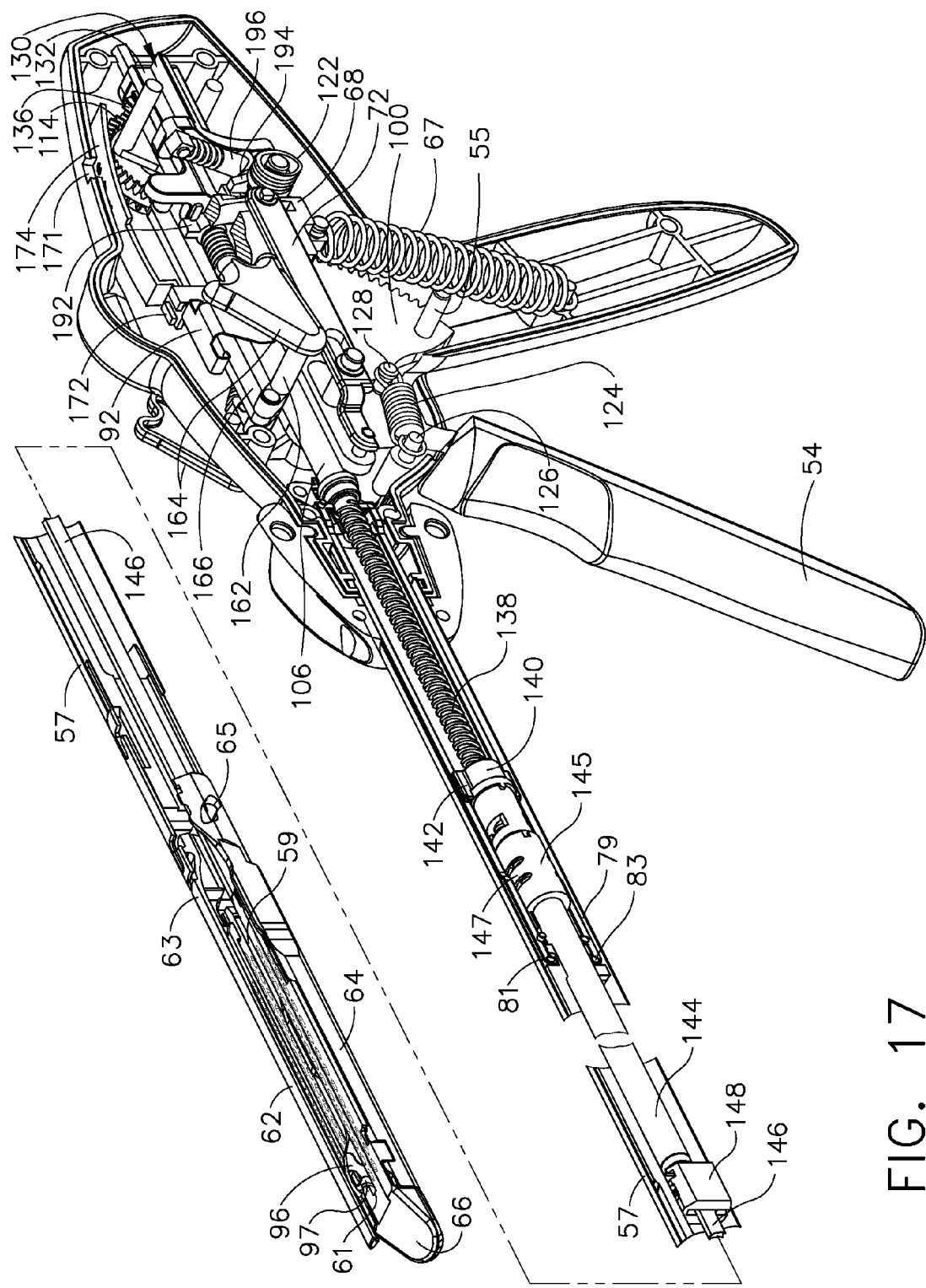
FIG. 17 is a perspective view of the surgical instrument of FIG. 1 illustrating the configuration of the surgical instrument after the trigger has been released after the fourth actuation of the trigger and the switching mechanism of the surgical instrument has been operated.
Figure 18:
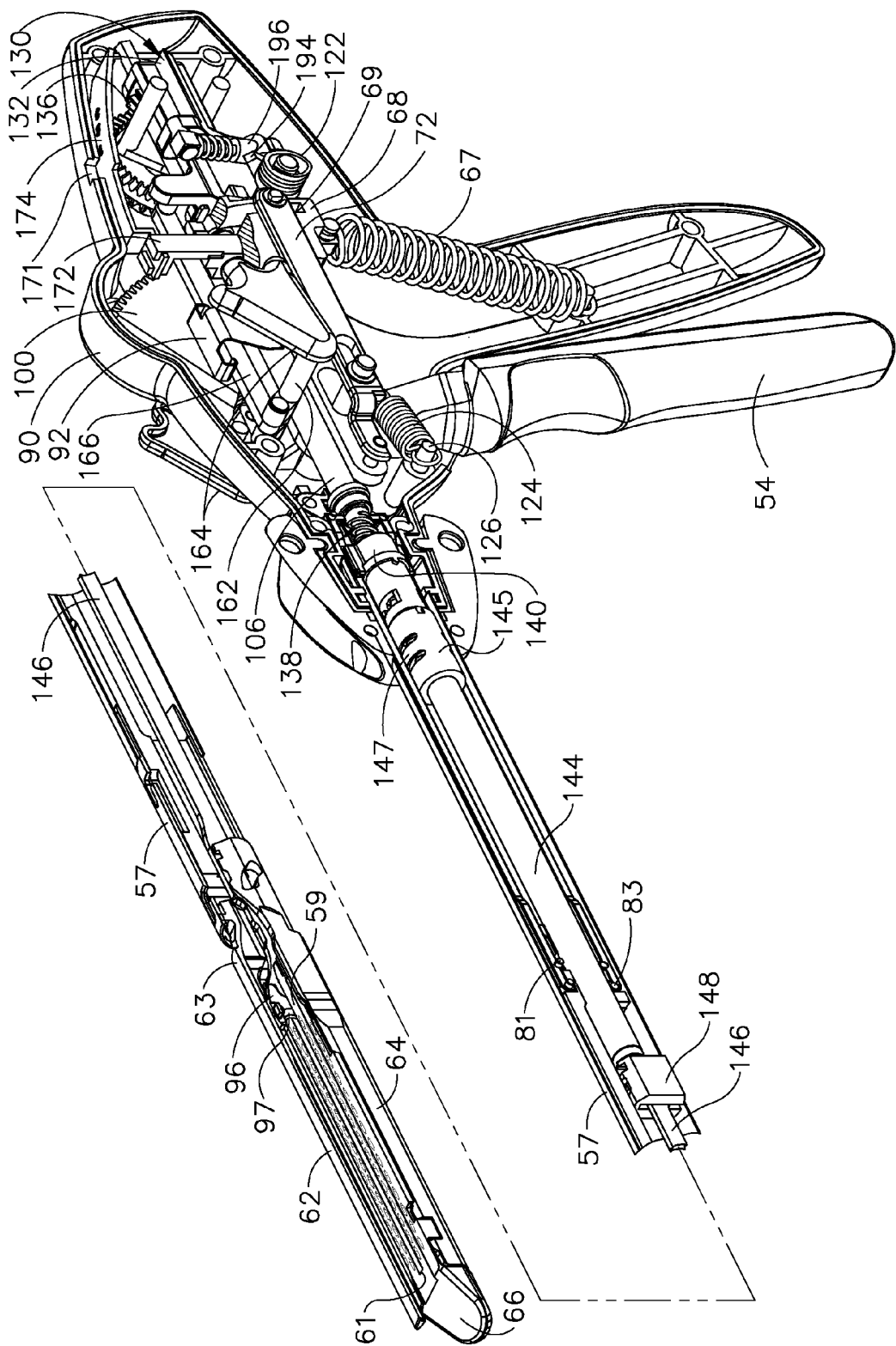
FIG. 18 is a perspective view of the surgical instrument of FIG. 1 illustrating the configuration of the surgical instrument upon the seventh actuation of the trigger with the cutting member fully retracted.
Figure 19:
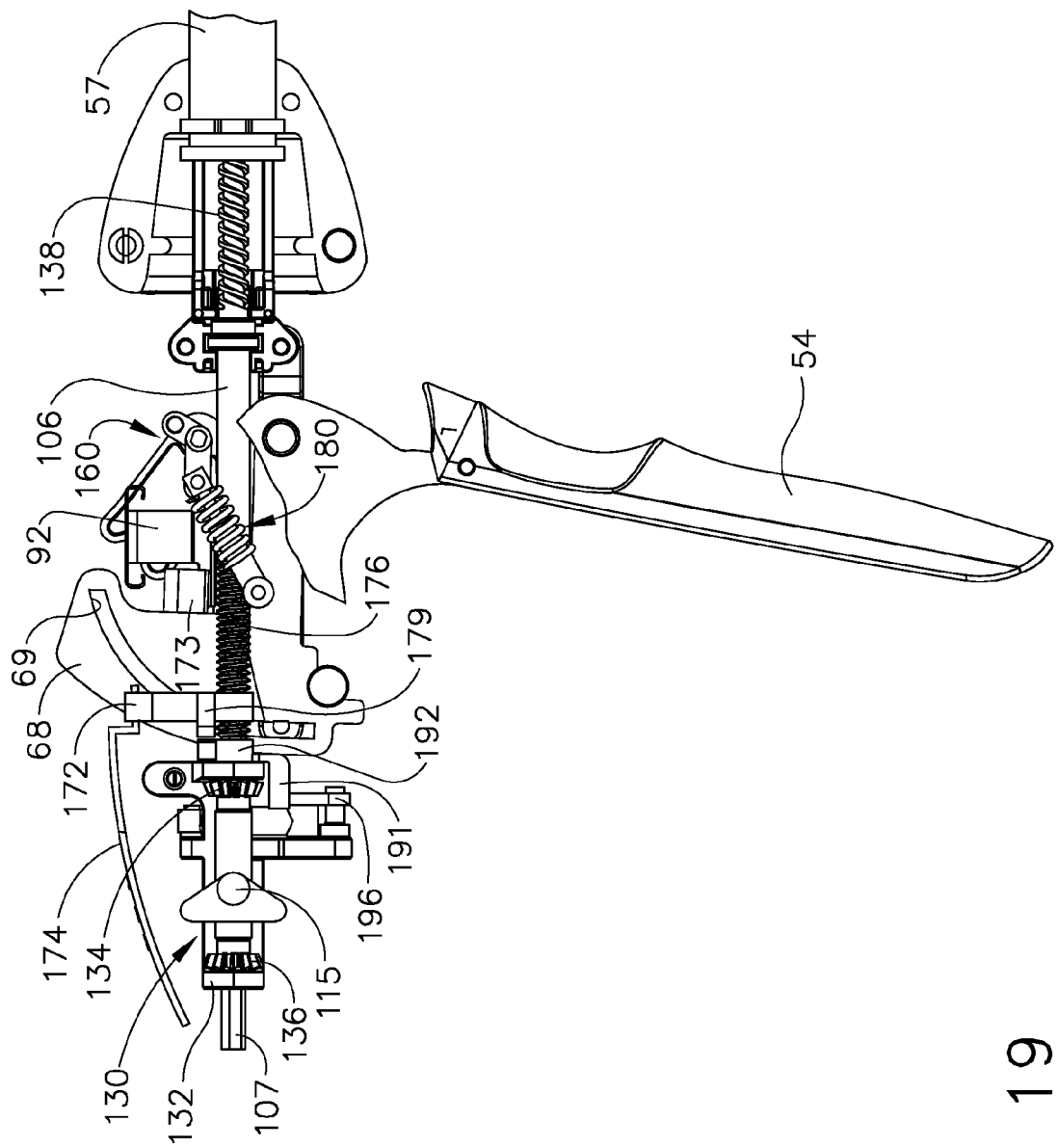
FIG. 19 is a partial elevational view of the surgical instrument of FIG. 1 illustrated in the configuration of FIG. 18 with components of the surgical instrument removed.

In order to retract cutting member 96, as outlined above, gear carriage 130 can be shifted such that forward gear 134 is disengaged from bevel gear 114 and, referring to FIGS. 17 and 18, reversing gear 136 is engaged with bevel gear 114. Thereafter, subsequent actuations of trigger 54 can rotate drive shaft 106 in the opposite direction and translate firing nut 140 proximally. More particularly, owing to the threaded engagement between firing nut 140 and threaded portion 138 of drive shaft 106, the rotation of shaft 106 in the opposite direction applies a rectional force to firing nut 140 which displaces firing nut 140 in the proximal direction. Accordingly, firing rod 144, drive bar 146 and cutting member 96, which can be connected to firing nut 140 as described above, are also displaced in the proximal direction thereby retracting cutting member 96 within end effector 58. Similarly, the rotation of shaft 106 in the opposite direction can displace indictor nut 172 of indicator assembly 170 proximally as well. More particularly, the first actuation of trigger 54 after gear carriage 130 has been shifted, i.e., the fifth overall actuation of trigger 54, can cause drive shaft 106 to apply a rectional force to indicator nut 172 and move nut 172 proximally. In such circumstances, indicator nut 172 can move indicator plate 174 relative to window 171 such that the numeral '2' is visible through indicator window 171 which can remind the surgeon that two more actuations of trigger 54 are required to fully retract cutting member 96.

Although trigger 54 is actuated three times to advance and/or retract cutting member 96 in the present embodiment, the actuations required to advance cutting member 96 can be different than the actuations required to retract cutting member 96 in other embodiments. Exemplary embodiments including features for advancing and retracting cutting member 96 at different rates are described in detail further below. Furthermore, in at least one embodiment, portion 95 of cutting member 96 can be engaged with the staple driver such the retraction of cutting member 96 also retracts the staple driver. In other embodiments, however, the staple driver can be left behind in the staple cartridge and only the cutting member 96 is retracted. Such embodiments may be utilized where a spent staple cartridge assembly is replaced with a new staple cartridge assembly which includes its own staple driver therein and, as a result, it may be desirable to leave the used staple driver in the spent cartridge.

In order to motivate gear carriage 130 as described above, surgical instrument 50 can include, referring to FIGS. 3-5, switching mechanism 160. In at least one embodiment, switching mechanism 160 can include shaft switch 162, shifter handles 164 extending therefrom, and shifter link 166, where shifter link 166 can be connected to shaft 162 via shifter pin 169 and gear carriage housing 132 via pin 168. In order to slide gear carriage 130 relative to drive shaft 106 as described above, shifter handles 164 can be configured to rotate shaft 162 such that crank arm 163 extending from shaft 162 displaces shifter link 166 and drives gear carriage 130 along axis 105 of drive shaft 106. In the illustrated embodiment, when shifter handles 164 are oriented in a substantially downward direction, as illustrated in FIG. 8, crank arm 163 is oriented in a substantially upward direction. In this configuration, referring to FIG. 5, gear carriage 130 is positioned in its most rearward, or proximal, position such that forward gear 134 is operably engaged with bevel gear 114. In order to shift surgical instrument 50 into a configuration in which cutting member 96 is retracted, shifter handles 164 can be rotated upwardly, as illustrated in FIG. 17, to rotate crank arm 163 forward, or distally. Correspondingly, crank arm 163 can be configured to displace link arm 166 distally and pull gear carriage 130 into its most distal position, thereby engaging reversing gear 136 with bevel gear 114. In the event that the surgeon desires to advance cutting member 96 after at least partially retracting cutting member 96, the surgeon can rotate shifter handles 164 downwardly and re-engage forward gear 134 with bevel gear 114.

In various embodiments, referring to FIGS. 3 and 5, surgical instrument 50 can further include a bistable compliant mechanism for biasing switching mechanism 160 into a configuration where one of gears 134 or 136 is engaged with bevel gear 114. Stated another way, the bistable compliant mechanism can cause switching mechanism 160 to become dynamically unstable when a surgeon only partially rotates shifter handles 164. In such circumstances, the bistable compliant mechanism can bias switching mechanism 160 into one of two configurations where it is stable, i.e., the forward and reversing configurations. In various embodiments, bistable compliant mechanism 180, referring primarily to FIG. 3, can include receiver 182, spring 184, plunger 186 and toggle pin 188. In at least one embodiment, toggle pin 188 can connect plunger 186 to switch shaft 162 and receiver 182 can be connected to projection 183 extending from housing 90. In use, spring 184 can be configured to apply a biasing force to shaft 162 via plunger 186 and can be configured to rotate shaft 162 in the event that shaft 162 is only partially rotated between its forward and reversing orientations.

In various embodiments, once cutting member 96 has been fully retracted, the end effector closing system and the staple firing system can be reset so that the spent staple cartridge can be removed from surgical instrument 50, a new staple cartridge 66 can be positioned within staple cartridge channel 64, and surgical instrument 50 can be used to further staple and cut tissue as described above. In the illustrated embodiment, cam 68 can be released from lock 92 to open anvil 62 and reset the end effector closure system. Similarly, ratchet gear 108 can be disengaged from main drive gear 110 to disengage trigger 54 from gear train 102 and reset the staple firing system. In at least one embodiment, cam 68 and ratchet gear 108 can be manually reset, however, referring primarily to FIGS. 3-5, 9, 10, 19 and 20, surgical instrument 50 can include a reset system which can automatically reset the end effector closure system and staple firing system described above. In various embodiments, the final return actuation of trigger 54 can reset these systems as described in detail below.

As outlined above, the first actuation of trigger 54 can rotate cam 68 into the position illustrated in FIG. 8 and spring lock 92 can be configured to hold cam 68 in place as the firing drive is operated by subsequent actuations of trigger 54. As also illustrated in FIG. 8, surgical instrument 50 can further include cam spring 67 which can be configured to bias cam 68 downwardly and, referring to FIGS. 9 and 10, hold cam lock arm 73 extending from cam 68 against spring lock 92. In such embodiments, cam lock arm 73 can include recess 74 which can be configured to receive at least a portion of spring lock 92. In order to assist cam spring 67 in keeping cam 68 from lifting upwardly during subsequent actuations of trigger 54 and becoming disengaged from cam spring 92, indicator nut 174 can be configured to contact cam rail 75 and hold cam lock arm 73 against spring lock 92. More particularly, as indicator nut 174 is advanced distally, as described above, indicator nut 174 can be slid along contact rail 75 providing a positive stop against which cam 68 cannot rotate. Once indicator nut 174 is returned to its most proximal position, however, indicator nut 174 can become aligned with ramp 89 and, as a result, the third return actuation of trigger 54 can cause cam 68 to rotate upward slightly, thereby disengaging lock arm 73 from spring lock 92 as illustrated in FIG. 10.

After cam 68 has been released from lock 92, cam return spring 67 can be configured to rotate cam 68 downwardly and return it to its original position. As cam 68 is rotated downwardly, the walls of cam slot 69 can be configured to drive closure links 72 distally and, correspondingly, drive channel portions 78 and 80 and staple cartridge channel 64 distally as well. In at least one embodiment, end effector 58 can further include a spring (not illustrated) configured to bias anvil 62 upwardly as staple cartridge channel 64 is slid distally, i.e., away from outer sheath 57 of elongate shaft assembly 56. In other various embodiments, although not illustrated, surgical instrument 50 can further include an actuator in which a surgeon can operate to pull or push anvil 62 into an open position. In either event, in at least one embodiment, cam return spring 67 can assert a force sufficient for cam 68 to displace ratchet gear 108 out of engagement with main drive gear 110 and, as a result, reset the firing drive. In other various embodiments, cam return spring 67 may not be strong enough to pull cam 68 downwardly with sufficient force to disengage ratchet gear 108 from main drive gear 110. In at least one such embodiment, surgical instrument 50 can further include, referring to FIGS. 3-5 and 19, a toggle switch assembly which can selectively bias ratchet gear 108 away from main drive gear 110.

Figure 9:
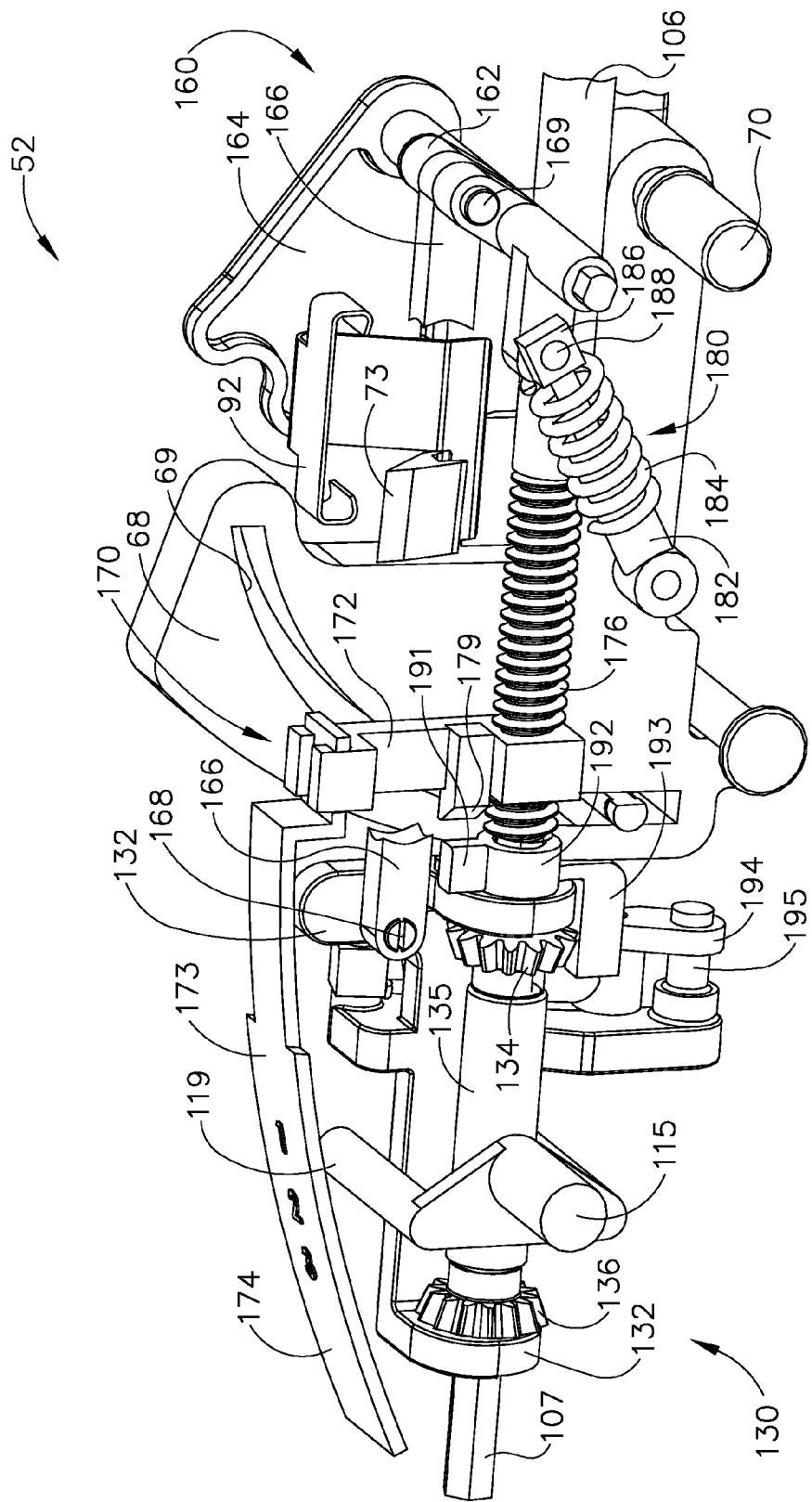
FIG. 9 is a partial perspective view of the surgical instrument of FIG. 1 in the configuration illustrated in FIG. 8 with some components of the surgical instrument removed.
Figure 11:
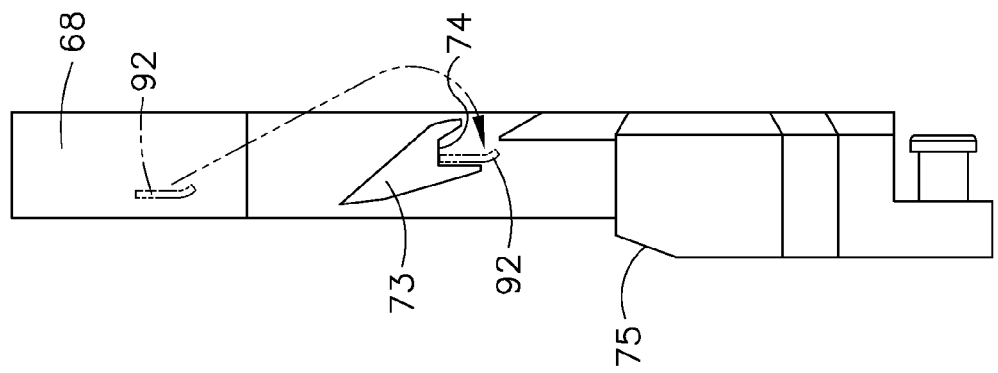
FIG. 11 is an elevational view of the cam of FIG. 10 illustrating various relative positions of a lock of the anvil closure system.
Figure 10:
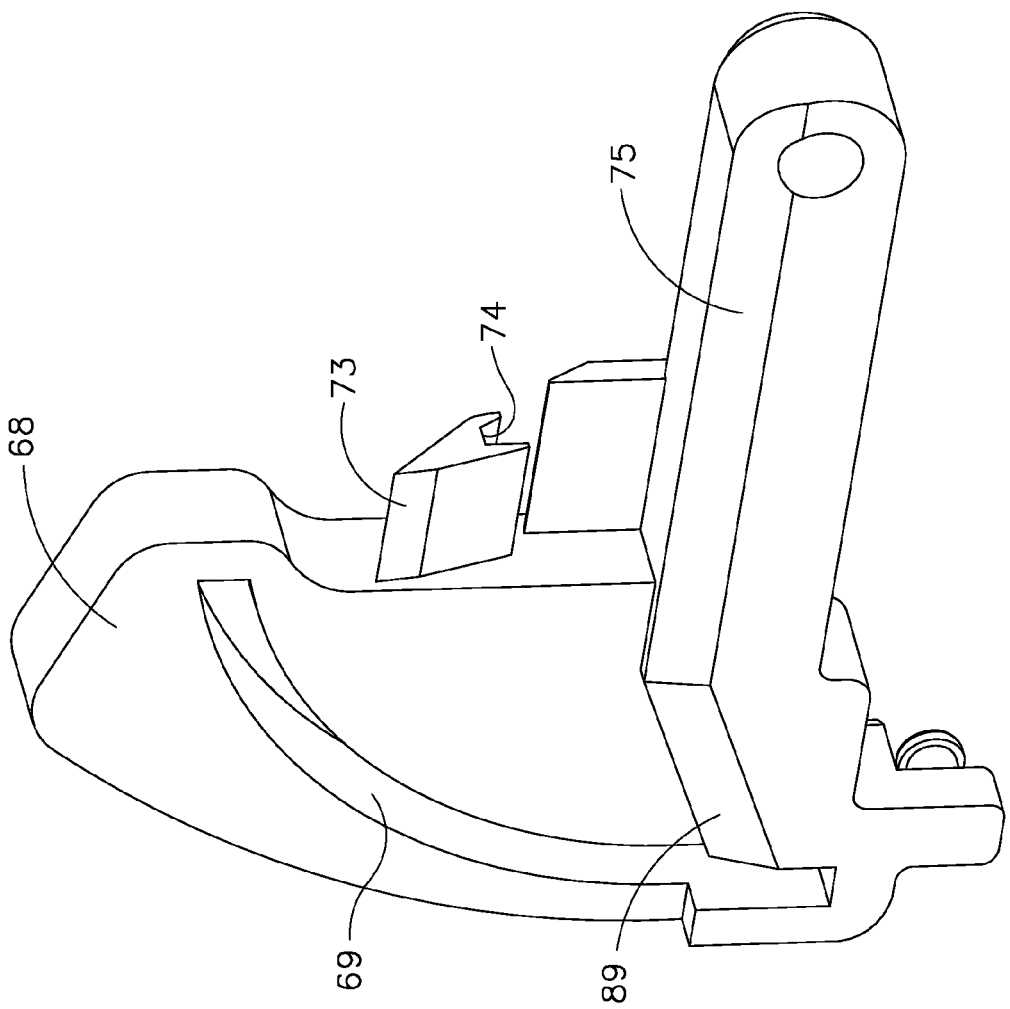
FIG. 10 is a perspective view of a cam of the end effector closure system of the surgical instrument of FIG. 1.
Figure 12:
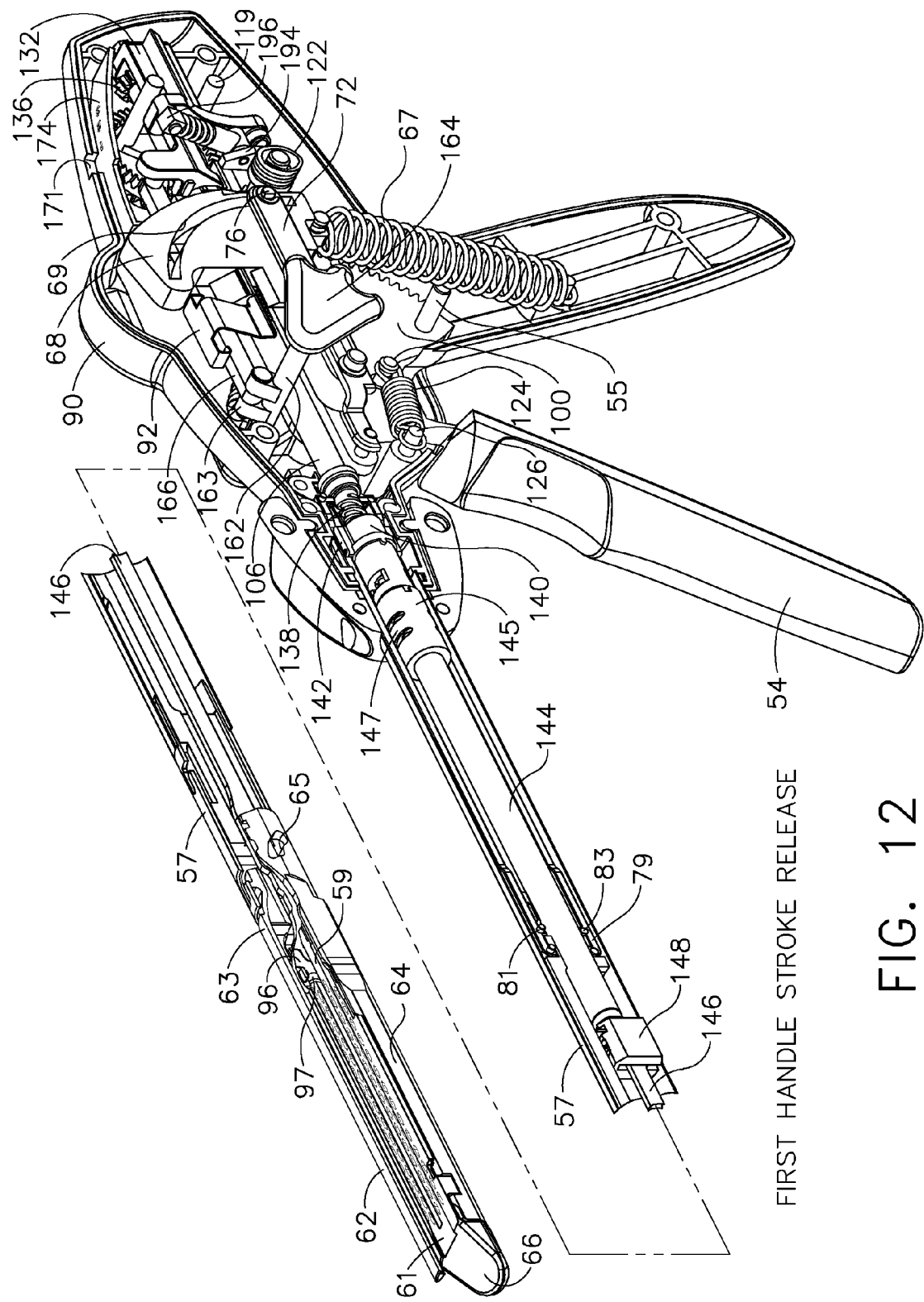
FIG. 12 is a perspective view of the surgical instrument of FIG. 1 illustrating the configuration of the surgical instrument after the trigger has been released after the first actuation of the trigger.
Figure 13:
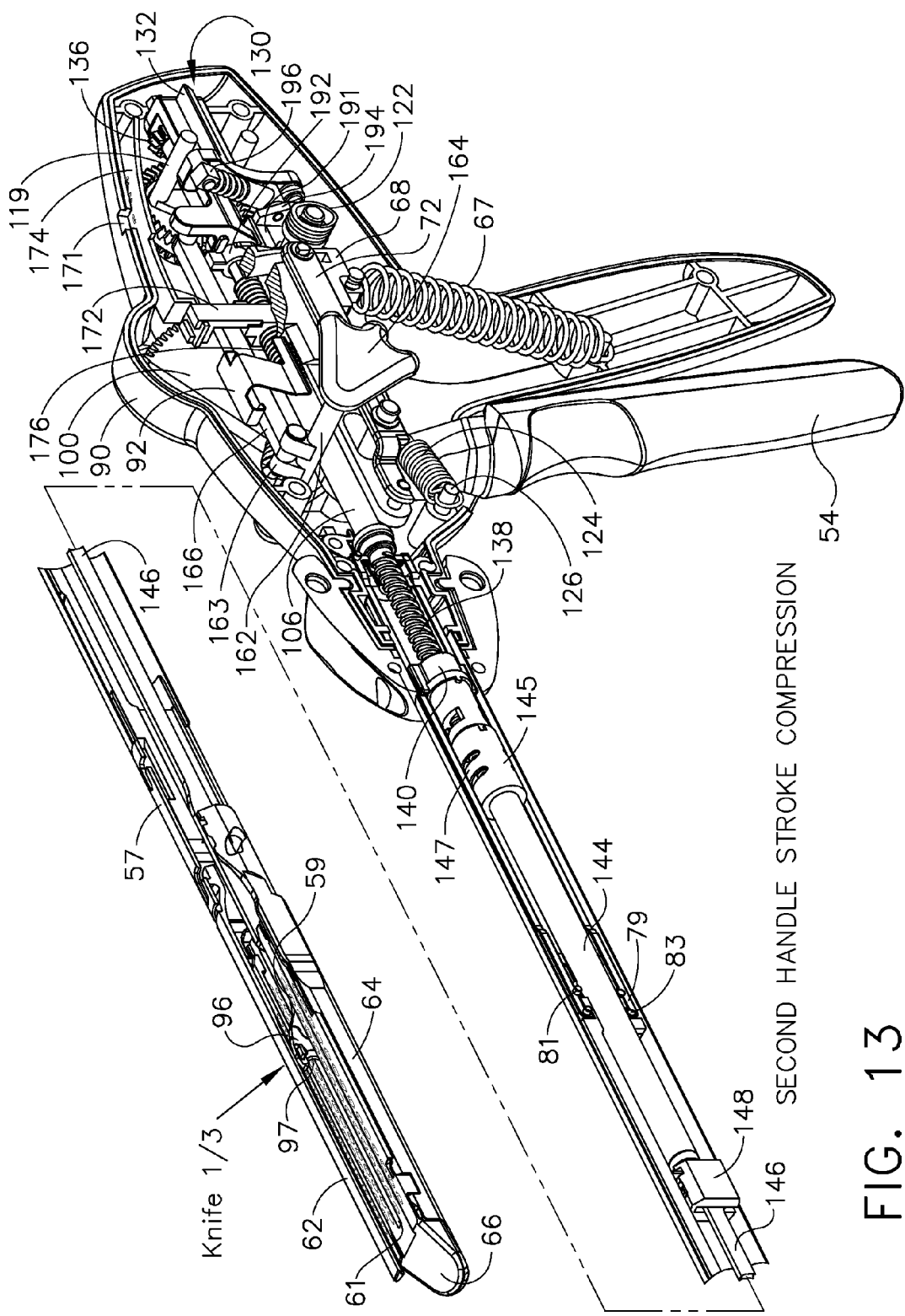
FIG. 13 is a perspective view of the surgical instrument of FIG. 1 illustrating the configuration of the surgical instrument upon the second actuation of the trigger.
Figure 14:
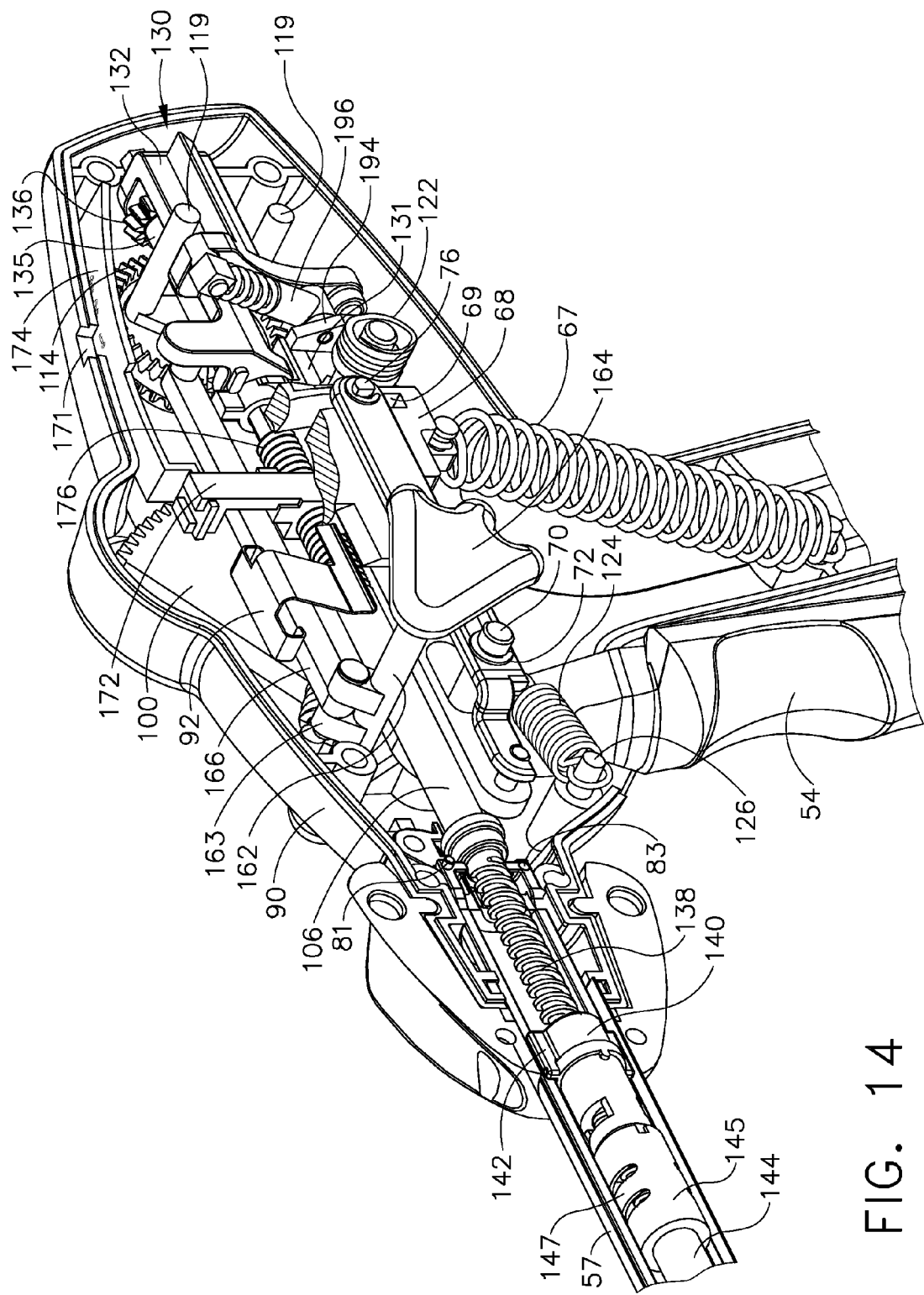
FIG. 14 is a partial perspective view of the surgical instrument of FIG. 1 in the configuration illustrated in FIG. 13.
Figure 15:
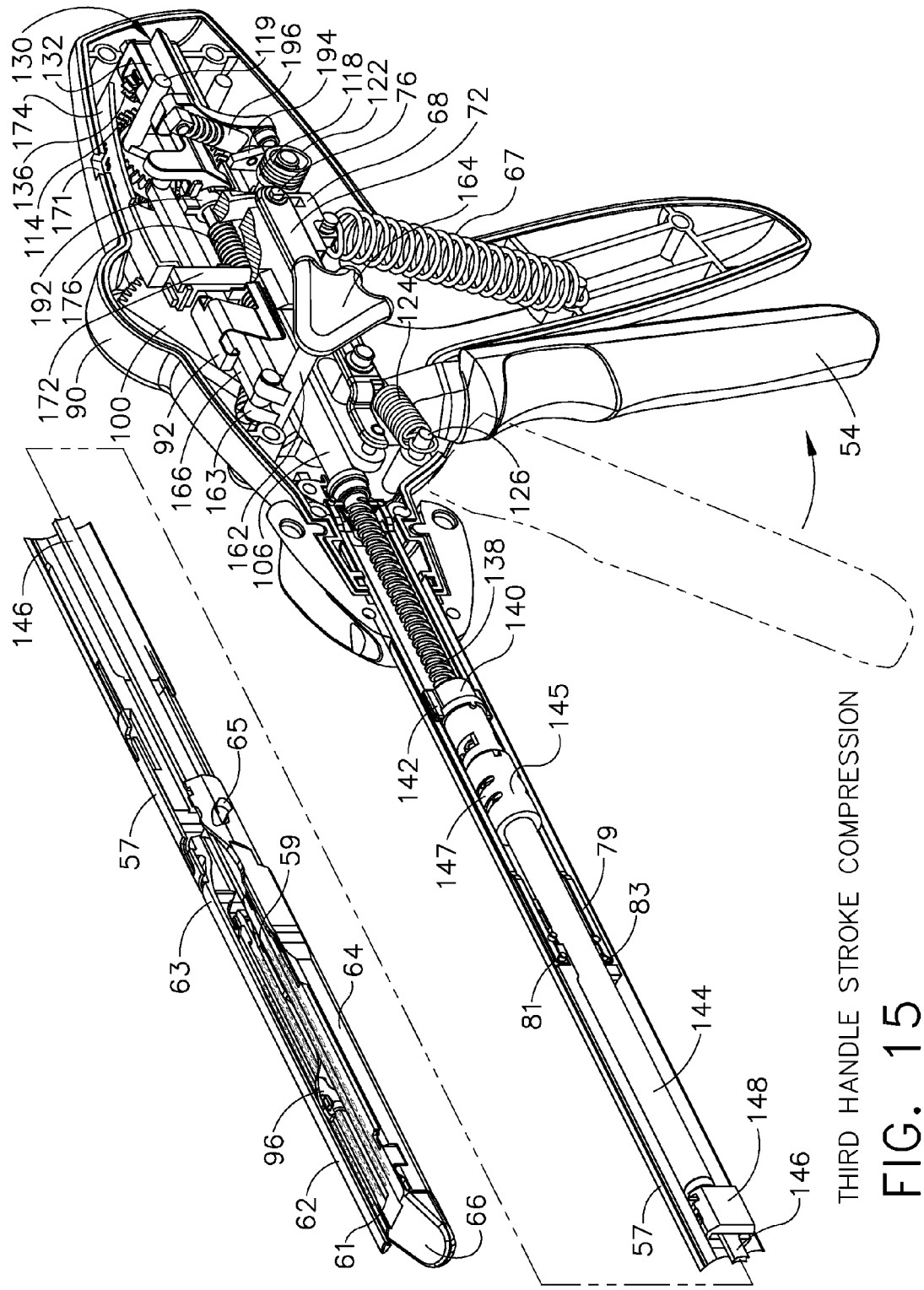
FIG. 15 is a perspective view of the surgical instrument of FIG. 1 illustrating the configuration of the surgical instrument upon the third actuation of the trigger.
Figure 16:
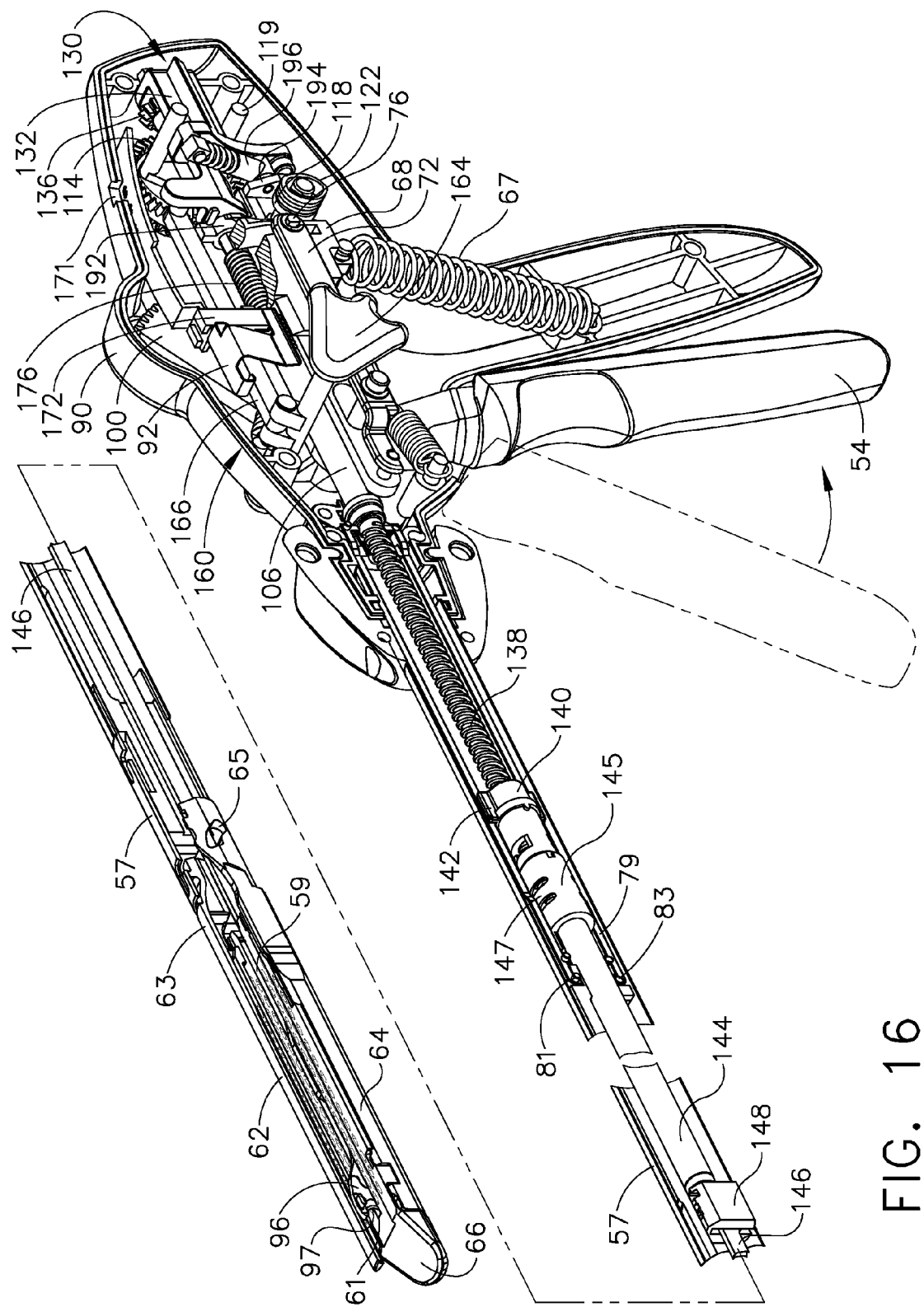
FIG. 16 is a perspective view of the surgical instrument of FIG. 1 illustrating the configuration of the surgical instrument upon the fourth actuation of the trigger.

In various embodiments, referring primarily to FIGS. 3, 4, and 9, toggle switch assembly 190 can include toggle actuator 192 mounted to drive shaft 106, where toggle actuator 192 can include toggle arm 193 extending therefrom. Upon the final return actuation of trigger 54, in at least one embodiment, indicator nut 172 can contact toggle actuator 192 and rotate it about drive shaft 106 such that toggle arm 193 is rotated toward ratchet gear 108. In at least one such embodiment, referring to FIG. 9, indicator nut 172 can further include ramp 179 which can be configured to engage projection 191 extending from toggle actuator 192 and rotate toggle actuator 192 clockwise about drive shaft 106. In various embodiments, toggle arm 193 can be configured to contact ratchet gear 108 as it is rotated about drive shaft 106 and displace ratchet gear 108 away from main drive gear 110. In at least one embodiment, ratchet gear 108 can be sufficiently displaced away from drive gear 110 to allow cam return spring 67 to position cam 68 adjacent collar 118. Thereafter, cam 68 can hold ratchet gear 108 in this position until cam 68 is rotated upwardly as described above.

Figure 20:
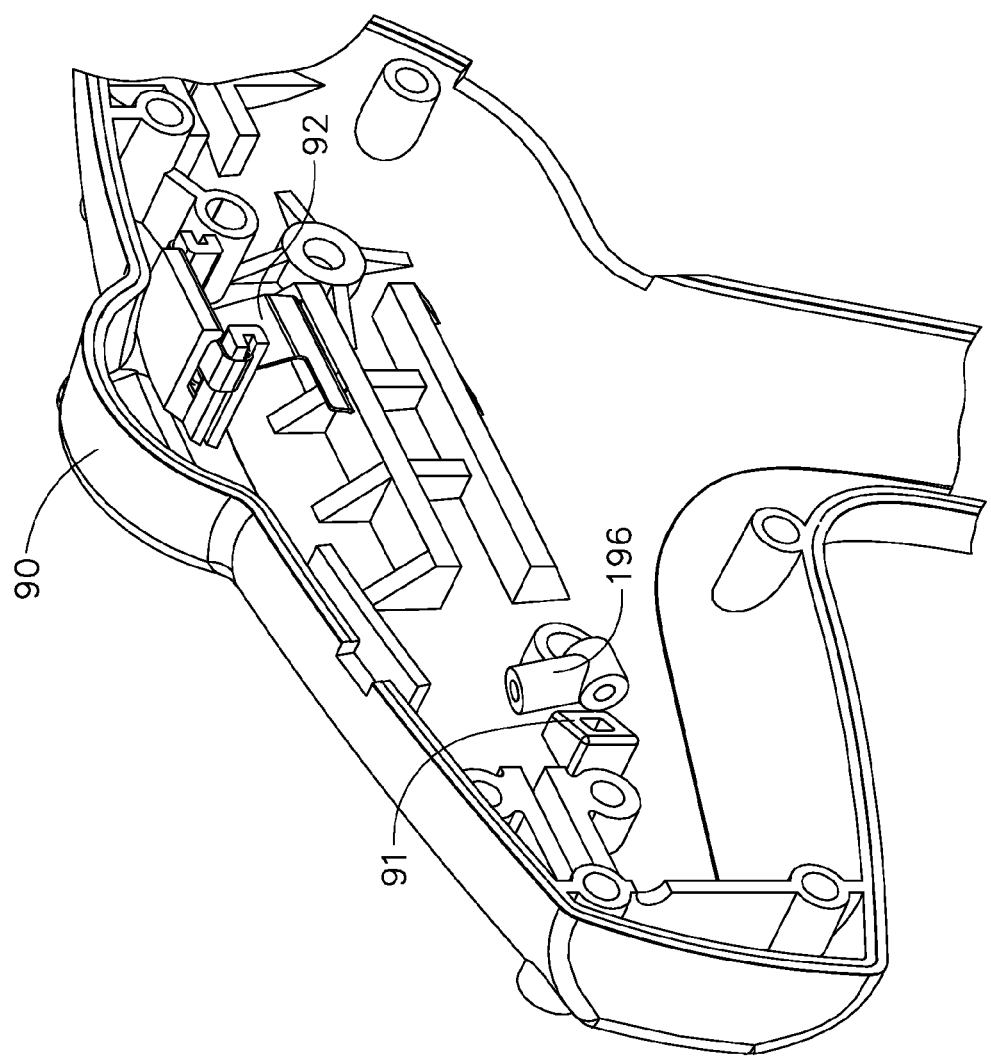
FIG. 20 is a partial perspective view of the housing of the surgical instrument of FIG. 1 illustrating the interaction of the firing drive and the housing after the seventh actuation of the trigger.

Although the above-described mechanisms can reset cam 68 and ratchet gear 108 into their initial positions, toggle arm 193 of toggle actuator 192, at least in the illustrated embodiment, can remain positioned against collar 118 of ratchet gear 108. Accordingly, even if cam 68 is rotated upwardly such that groove 120 is aligned with collar 118 upon the first actuation of trigger 54, ratchet gear 108 may not be released to engage main drive gear 110 as described above. In view of this, in at least one embodiment, surgical instrument 50 can include a reset mechanism for rotating toggle arm 193 out of engagement with ratchet gear 108. Such a mechanism can, in various embodiments, be manually operated and/or automatically operated in response to an actuation of trigger 54, for example. In at least one embodiment, as illustrated in FIG. 20, housing 90 can include projection 91 extending therefrom which can be configured to rotate toggle actuator 192 about drive shaft 106 and return it to its original, unactuated position as illustrated in FIG. 9. More particularly, in various embodiments, projection 91 can be configured to engage toggle link 194 (FIG. 3) as gear carriage 130 is moved from its distal position in which reversing gear 136 is engaged with bevel gear 114 to its proximal position in which forward gear 134 is engaged with bevel gear 114. Such movement can be effected by switching mechanism 160 when shifter handles 164 are rotated downwardly to move gear carriage 130 proximally and place surgical instrument 50 in its 'advancing' configuration described above. As a result of the contact between toggle link 194 and projection 91, toggle link 194 can be rotated about pin 195 such that toggle link 194 contacts actuator arm 193 and rotates toggle actuator 192 counterclockwise about drive shaft 106. In various embodiments, toggle switch assembly 190 can further include bistable compliant mechanism 196, which can assist in assuring that toggle switch assembly 190 does not become stuck in an intermediate configuration.

As described above, surgical instruments in accordance with the present invention can include a single trigger for actuating both an end effector closure system and a staple firing system. While the above-described features were described in connection with such single trigger surgical instruments, several of the features described above can be used in surgical instruments having a first trigger for actuating an end effector closure system and a second trigger for actuating a staple firing system. Referring to FIGS. 23-30, for example, surgical instrument 200 can include trigger 201 for actuating an end effector closure system and trigger 204 for actuating a staple firing system. In various embodiments, referring to FIG. 25, the end effector closure system can include closure link 203 operably engaged with closure trigger 201 via pin 209. The end effector closure system can further include slider 205 and closure tube 207 (FIG. 23), where closure tube 207 can be operably connected to closure link 203 via slider 205 and pin 211. More particularly, referring to FIG. 29, closure tube 207 can include flange 213 at its most proximal end which can be configured to be received within slot 215 in slider 205 such that the sliding motion of slider 205 is transmitted to closure tube 207.

Figure 29:
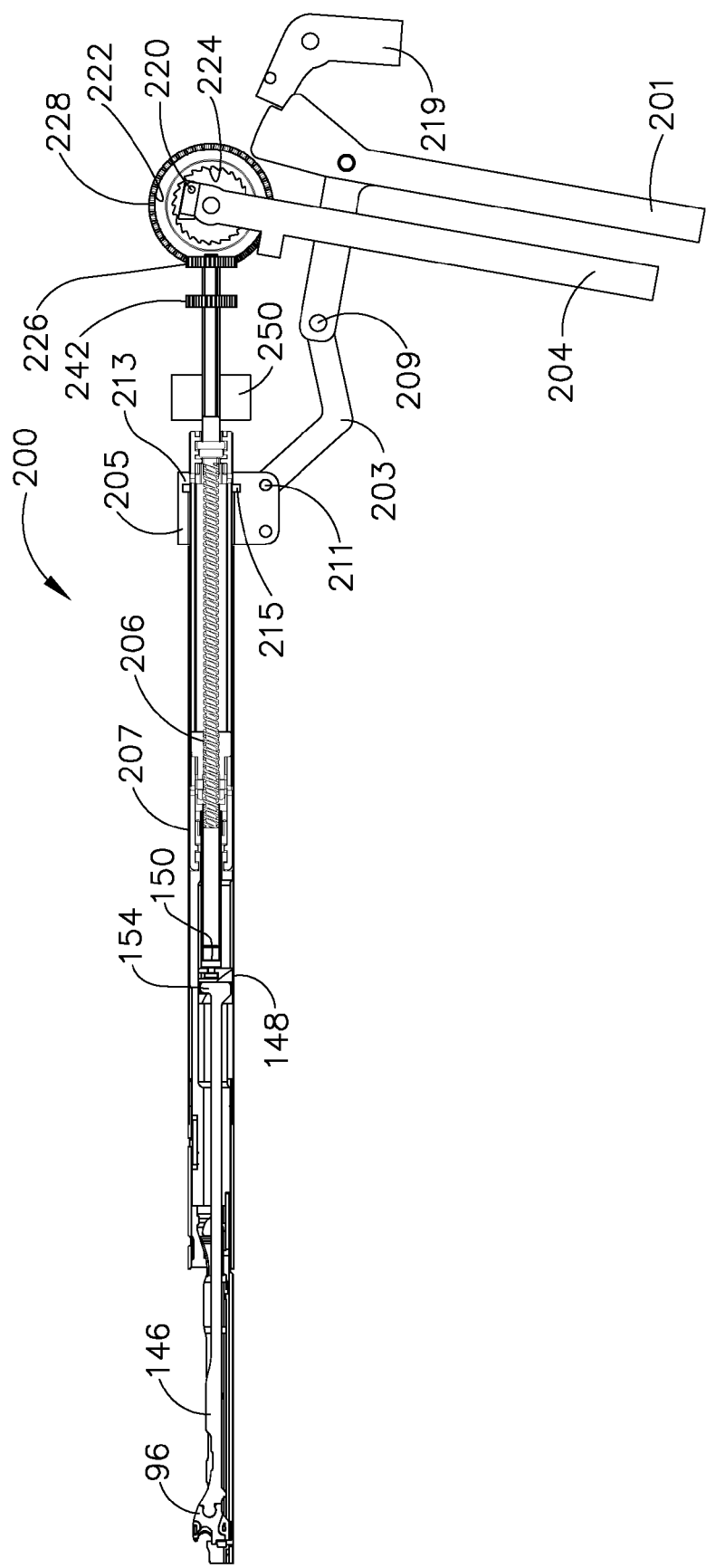
FIG. 29 is a side view of the surgical instrument of FIG. 23 configured to advance a cutting member within the end effector.
Figure 30:
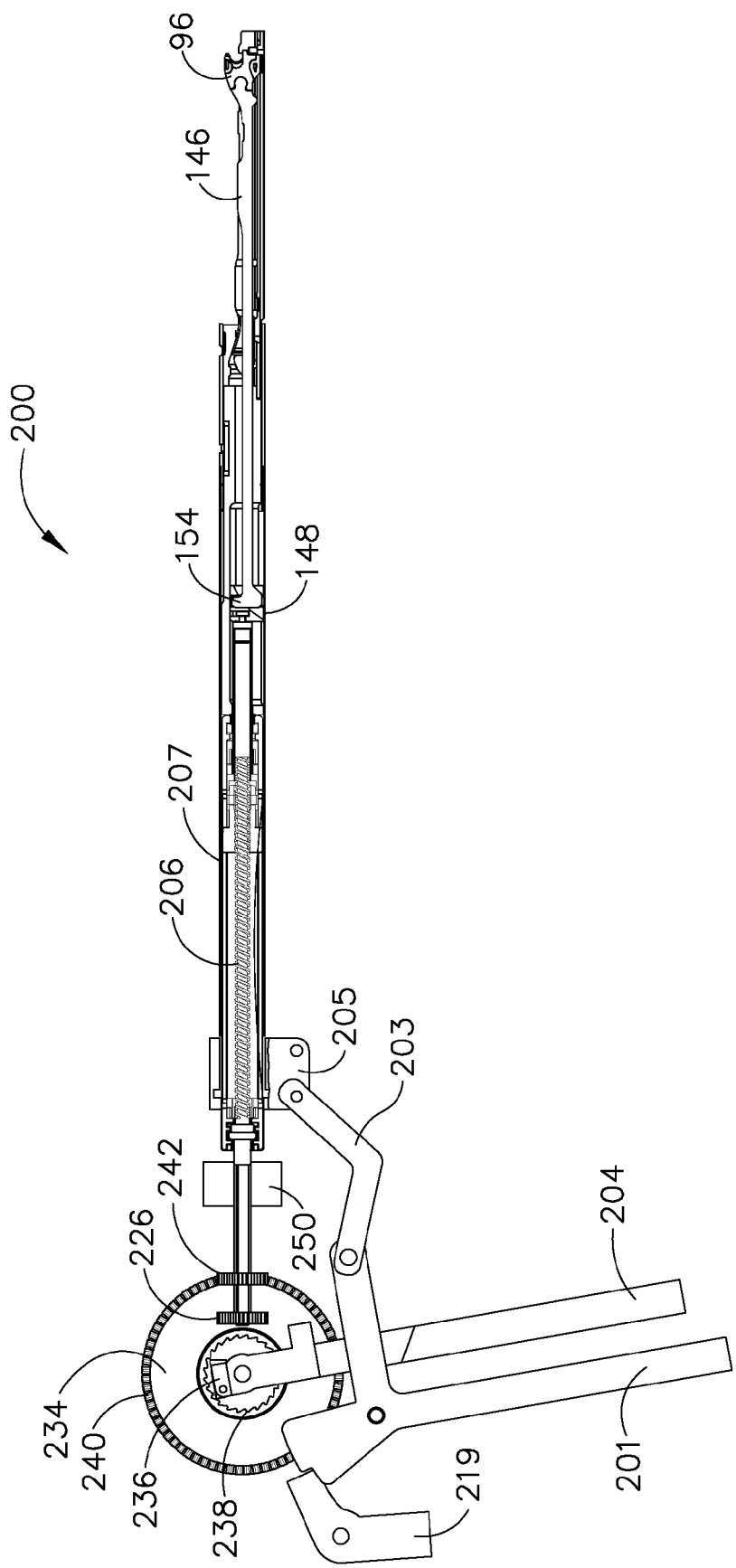
FIG. 30 is a side view of the surgical instrument of FIG. 23 configured to retract the cutting member within the end effector.

In use, referring primarily to FIGS. 29 and 30, the actuation of trigger 201 can translate closure link 203 distally and, correspondingly, translate slider 205 and closure tube 207 distally as well. In various embodiments, closure tube 207 can include features which are cooperatively engaged with anvil 62 such that translation of closure tube 207 causes anvil 62 to rotate toward staple cartridge channel 64. More particularly, referring to FIG. 24, anvil 62 can include projection 51 extending therefrom which can be received within aperture 217 of closure tube 207 such that sidewalls of aperture 217 can abut projection 51 and rotate anvil 62 downwardly. To guide anvil 62, as outlined above, staple cartridge channel 64 can include slots 65 which can define a path for anvil 62 as it is rotated. Surgical instrument 200 can further include lock 219 which can be configured to hold trigger 201 in an actuated position thereby holding anvil 62 in a closed position. To open anvil 62, lock 219 (FIG. 28) can be disengaged from trigger 201 such that trigger 201 can be returned to its unactuated position. As trigger 201 is returned to its unactuated position, trigger 201 can drive slider 205 and closure tube 207 proximally and, owing to the operative engagement between projection 51 and aperture 217, rotate anvil 62 upwardly.

As indicated above, surgical instruments in accordance with the present invention can include a firing drive which can be configured to advance a cutting member, for example, at a first rate and retract the cutting member at a different rate. In various embodiments, referring to FIGS. 23-30, surgical instrument 200 can include firing drive 202 which can comprise trigger 204, drive shaft 206, first ratchet assembly 210, and second ratchet assembly 212. In at least one embodiment, ratchet assemblies 210 and 212 can be configured to rotate drive shaft 206 in clockwise and counter-clockwise directions, respectively, in order to advance or retract cutting member 96 within end effector 58. In various embodiments, referring to FIG. 25, trigger 204 can be selectively engageable with ratchet assemblies 210 and 212 such that, when trigger 204 is actuated, only one of ratchet assemblies 210 and 212 is driven by trigger 204. In at least one such embodiment, trigger 204 can be slidable along pin 214 in order to engage trigger 204 with one of ratchet assemblies 210 and 212. In the illustrated embodiment, pin 214 can be rotatably received in apertures 216 in housing portions 218 and provide an axis of rotation for trigger 204.

Figure 25:
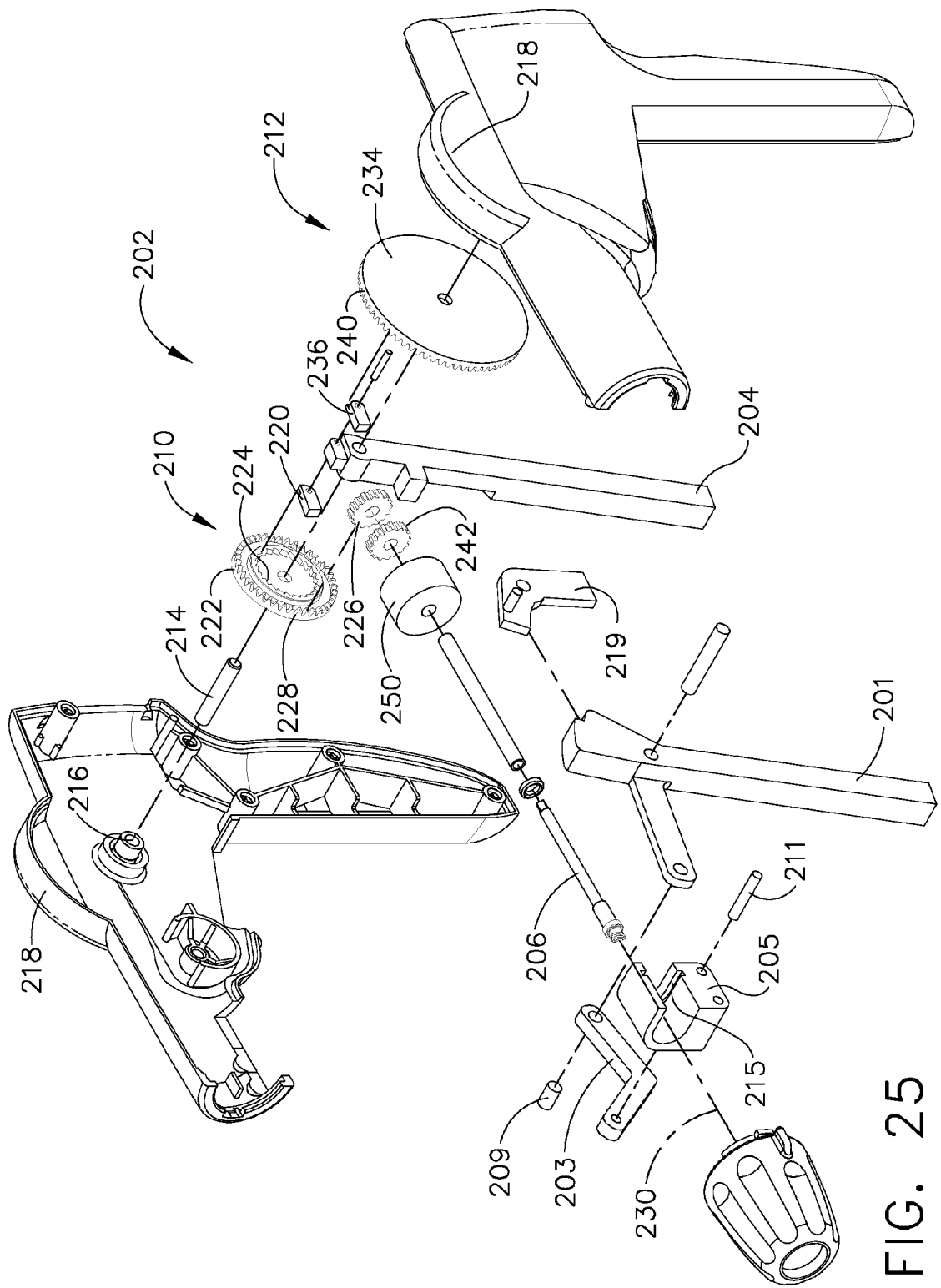
FIG. 25 is an exploded view of the handle portion of the surgical instrument of FIG. 23.
Figure 26:
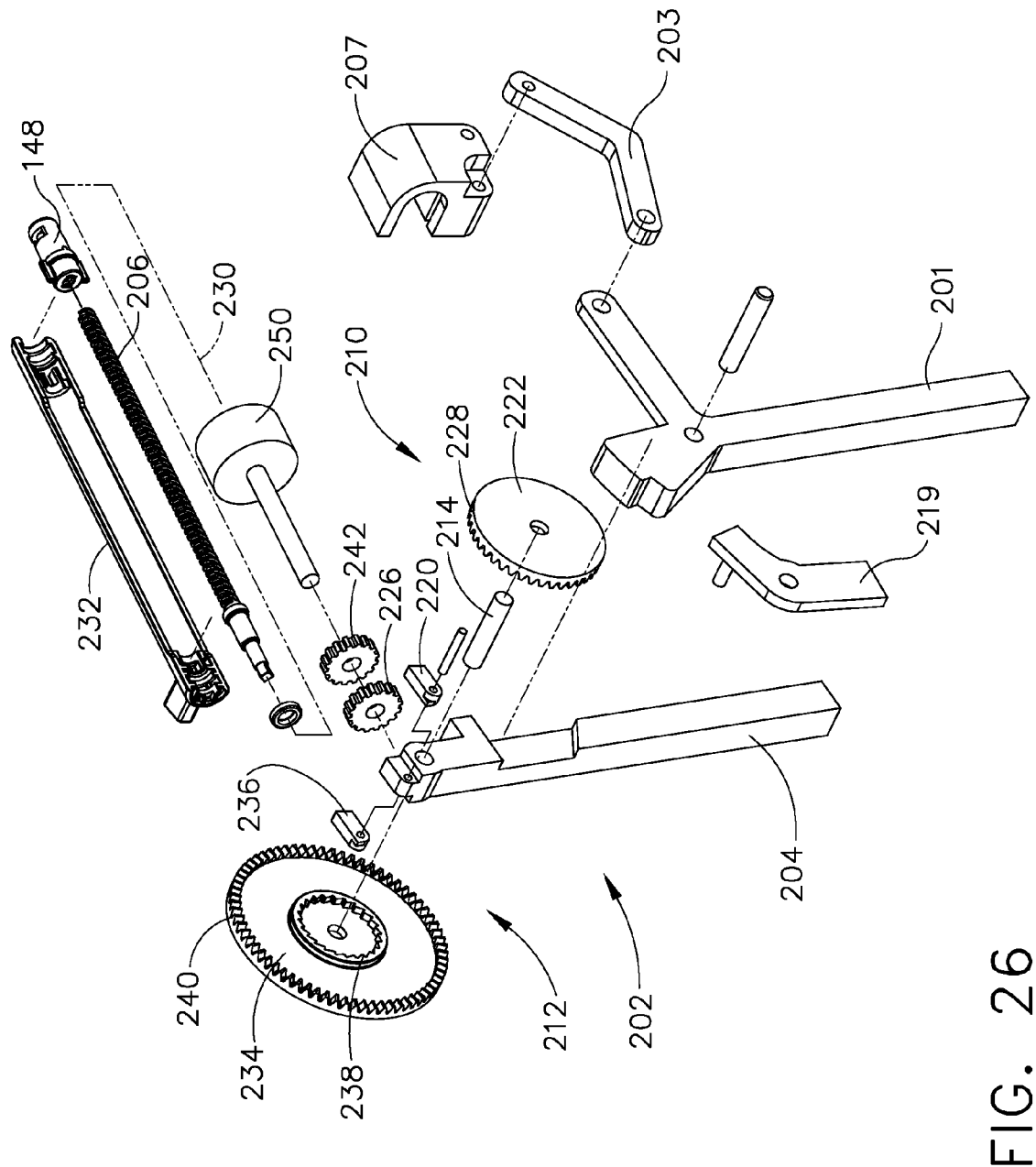
FIG. 26 is an exploded view of the surgical instrument of FIG. 23 with components of the surgical instrument removed.
Figure 27:
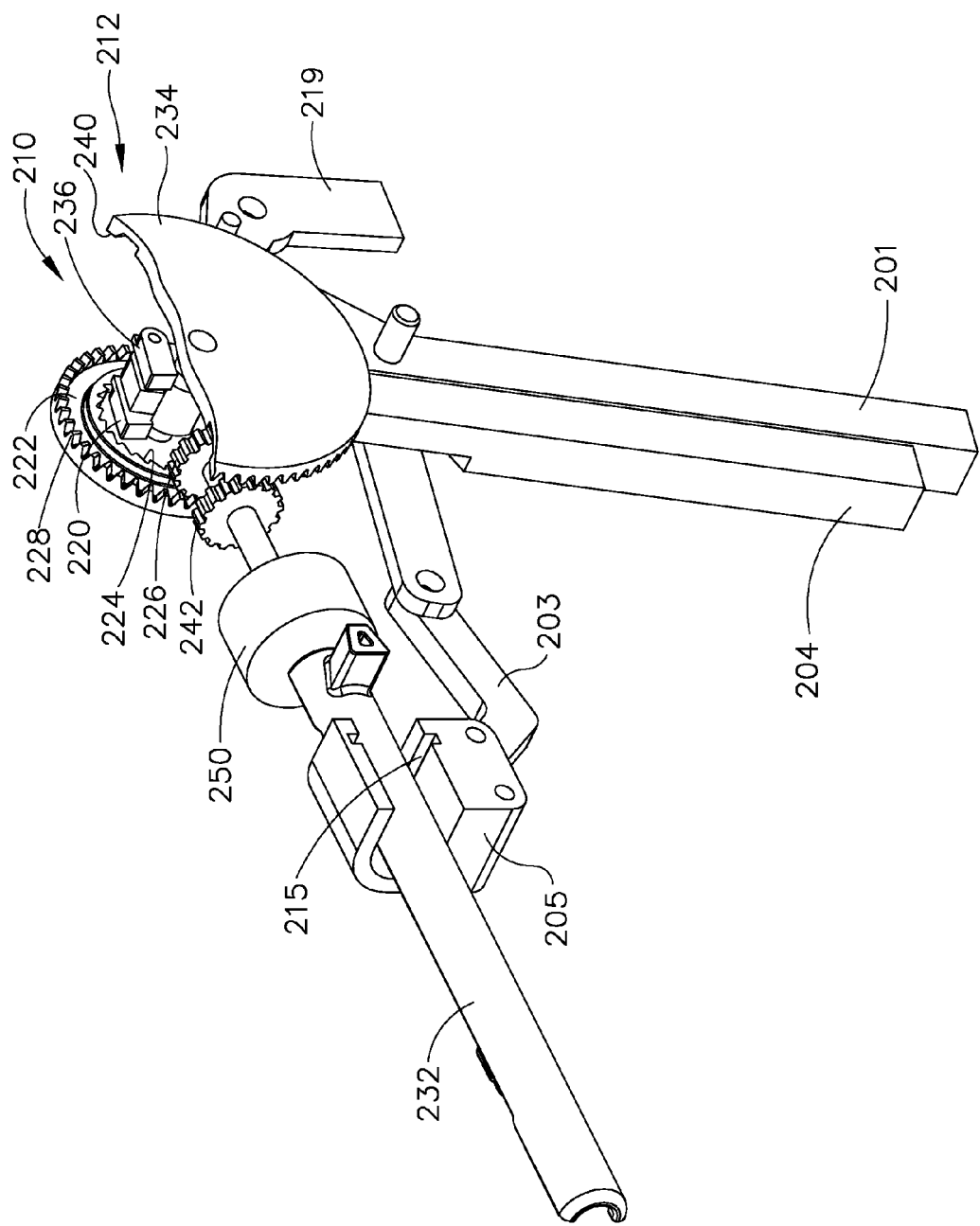
FIG. 27 is a perspective view of the surgical instrument of FIG. 23 with components of the surgical instrument removed.
Figure 28:
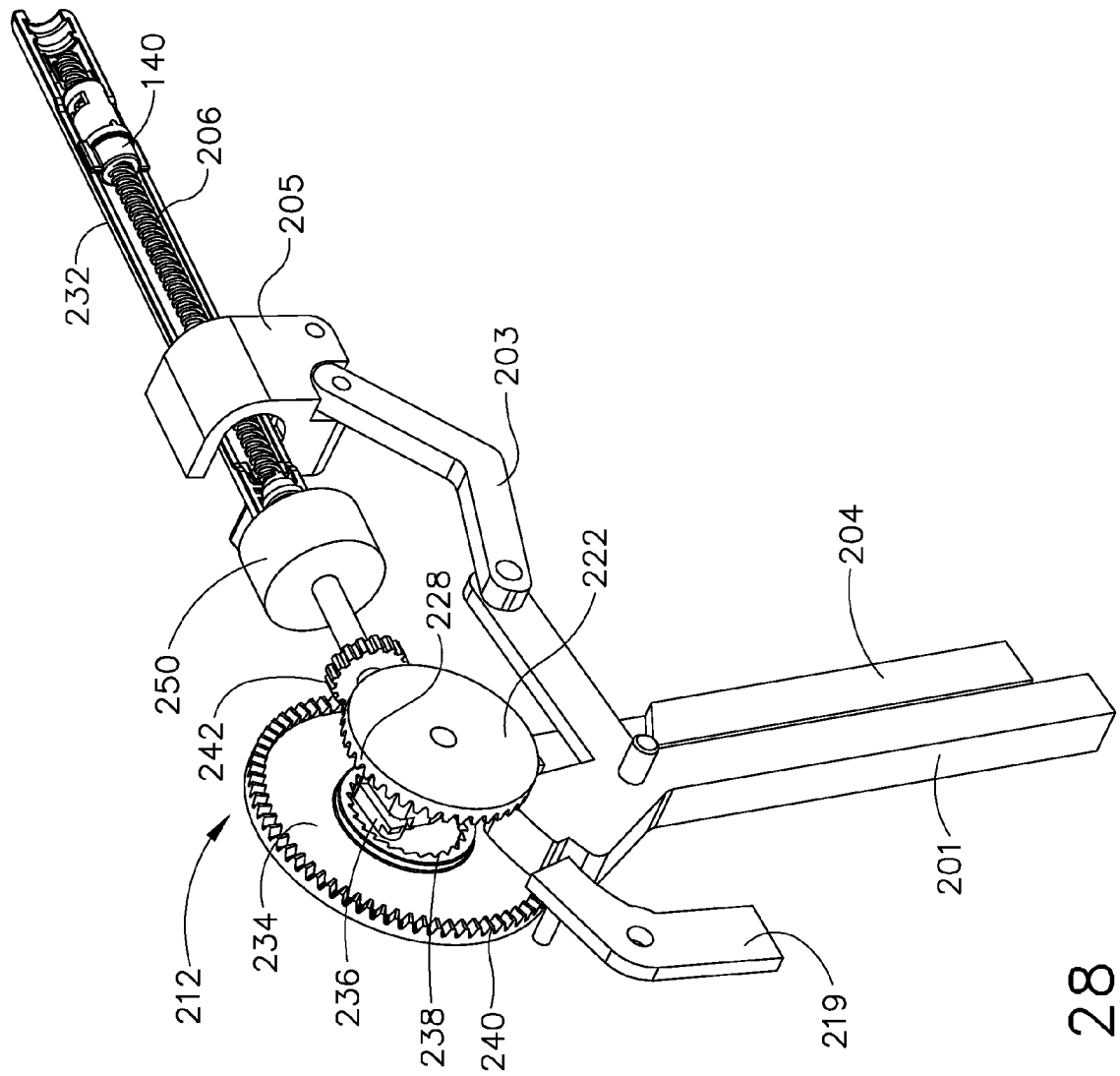
FIG. 28 is a second perspective view of the surgical instrument of FIG. 23 with components of the surgical instrument removed.

In various embodiments, referring to FIG. 27, trigger 204 can be positioned such that pawl 220, which can be pivotably mounted to trigger 204, is engaged with ratchet wheel 222 and, upon the actuation of trigger 204, ratchet wheel 222 is rotated about pin 214 by pawl 220. Upon the release of trigger 204, pawl 220 can slide over ratchet teeth 224 of ratchet wheel 222 permitting relative movement therebetween. In at least one embodiment, ratchet assembly 210 can further include a pawl spring (not illustrated) configured to bias pawl 220 into engagement with ratchet teeth 224 and re-engage pawl 220 with ratchet teeth 224 when trigger 204 is reactuated. In order to transmit the rotation of ratchet wheel 222 to drive shaft 206, drive shaft 206 can include forward gear 226 connected thereto. More particularly, in at least one embodiment, ratchet wheel 222 can further include gear teeth 228 which can be operably engaged with forward gear 226 such that the rotation of ratchet wheel 222 rotates forward gear 226 and drive shaft 206 about axis 230 (FIG. 25). In various embodiments, forward gear 226 can be press-fit, for example, onto drive shaft 206 or, in other various embodiments, forward gear 226 can be integrally formed with drive shaft 206.

In various embodiments, similar to the surgical instruments described above, drive shaft 206 can, referring to FIG. 24, be operably engaged with firing nut 140 in order to translate firing nut 140 within proximal retainer portion 232. As also described above, the translation of firing nut 140 can be transmitted to cutting member 96 via drive bar 146 in order to advance cutting member 96 within end effector 58. In order to retract cutting member 96 within end effector 58, in at least one embodiment, trigger 204 can be slid into engagement with second ratchet assembly 212 such that drive shaft 206 is rotated in the opposite direction when trigger 204 is actuated. Similar to ratchet assembly 210, referring to FIG. 28, ratchet assembly 212 can include ratchet wheel 234 and pawl 236 where pawl 236 can be pivotably mounted to trigger 204 and can be operatively engaged with ratchet wheel 234 via ratchet teeth 238. Similar to ratchet wheel 222, ratchet wheel 234 can include gear teeth 240 which can be operably engaged with reversing gear 242 mounted to drive shaft 206. As ratchet wheels 222 and 234 engage drive shaft 206 on substantially opposite sides, ratchet wheels 222 and 234 can rotate drive shaft 206 in opposite directions, i.e. clockwise and counter-clockwise directions, respectively. Thus, in order to select whether cutting member 96 is advanced or retracted within end effector 58, trigger 204 can be slid into operative engagement with either first ratchet assembly 210 or second ratchet assembly 212.

In various embodiments, although not illustrated, first ratchet wheel 222 and second ratchet wheel 234 can have substantially the same diameter, or pitch radius. Stated another way, the distance between the center, or axis of rotation, of the ratchet wheels and the gear teeth of the ratchet wheels can be the same. In such embodiments, the distance that cutting member 96 is advanced per actuation of trigger 204 will be substantially the same distance that cutting member 96 is retracted per actuation of trigger 204. While suitable in some circumstances, such embodiments may require a surgeon to actuate trigger 204 several times before cutting member 96 is completely retracted. In view of the above, in various embodiments, first ratchet wheel 222 can have a pitch radius which is different than the pitch radius of second ratchet wheel 234. In at least one embodiment, second ratchet wheel 234 can have a larger pitch radius than first ratchet wheel 222 such that cutting member 96 is retracted a distance per actuation of trigger 204 which is greater than the distance that cutting member 96 is advanced per actuation of trigger 204. Stated another way, second ratchet assembly 212 can, at least in these embodiments, retract cutting member 96 at a rate which is greater than which it is advanced. In such embodiments, first ratchet assembly 210 can, owing to the slower advancing rate, provide a greater torque or advancing force to cutting member 96 while second ratchet assembly 212 can, owing to the faster retracting rate, reduce the time required for the surgeon to retract the cutting member.

While the term 'rate', as used above, is used to describe the distance that cutting member 96 can be advanced or retracted per actuation of trigger 204, the term 'rate' is not so limited. In at least one embodiment, the term 'rate' can be used to describe the velocity and/or acceleration in which the cutting member is moved. In such embodiments, it may be desirable to have a cutting member which is advanced at a lower velocity and/or acceleration to better control the cutting member and retracted at a greater velocity and/or acceleration to reduce the time required to retract the cutting member. Furthermore, while the illustrated embodiments include ratchet assemblies for providing the different advancing and retracting rates, the invention is not so limited. On the contrary, other embodiments are envisioned which include spur gear trains, bevel gears, and/or other motion transmission devices.

Figure 21:
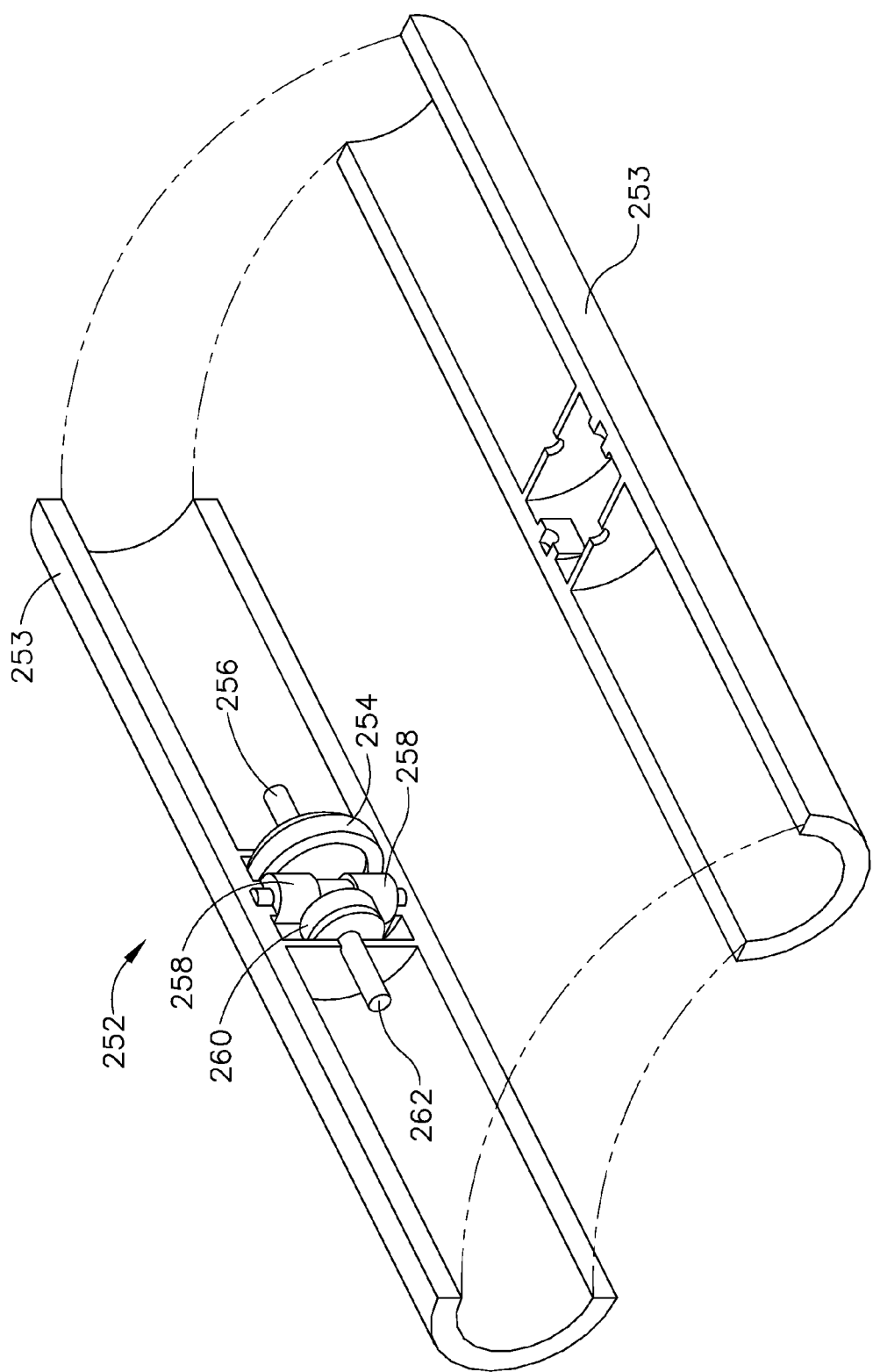
FIG. 21 is a perspective view of a gear reduction mechanism for a surgical instrument in accordance with an alternative embodiment of the present invention with a portion of the gear reduction housing disassembled.
Figure 22:
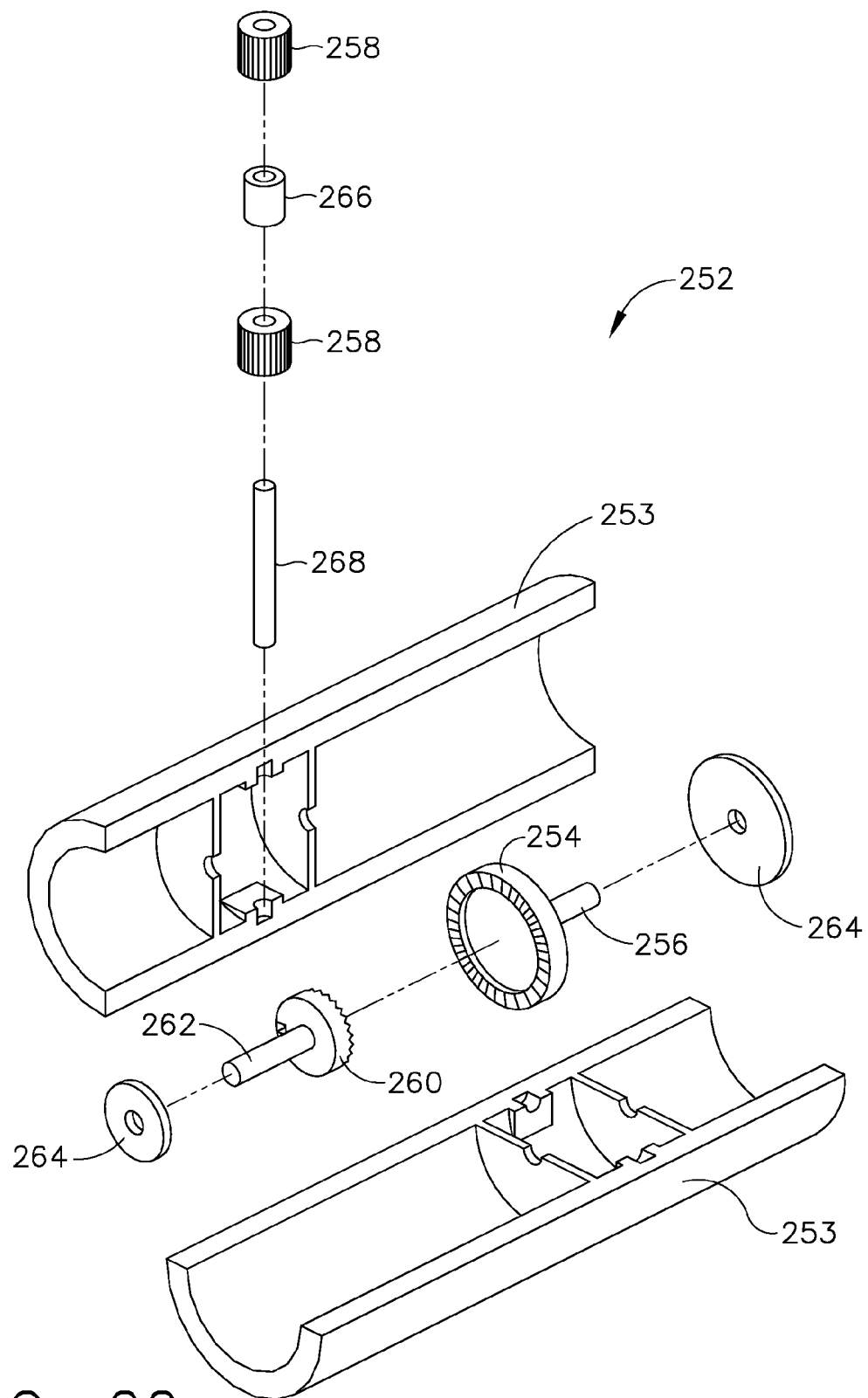
FIG. 22 is an exploded view of the gear reduction mechanism of FIG. 21.
Figure 23:
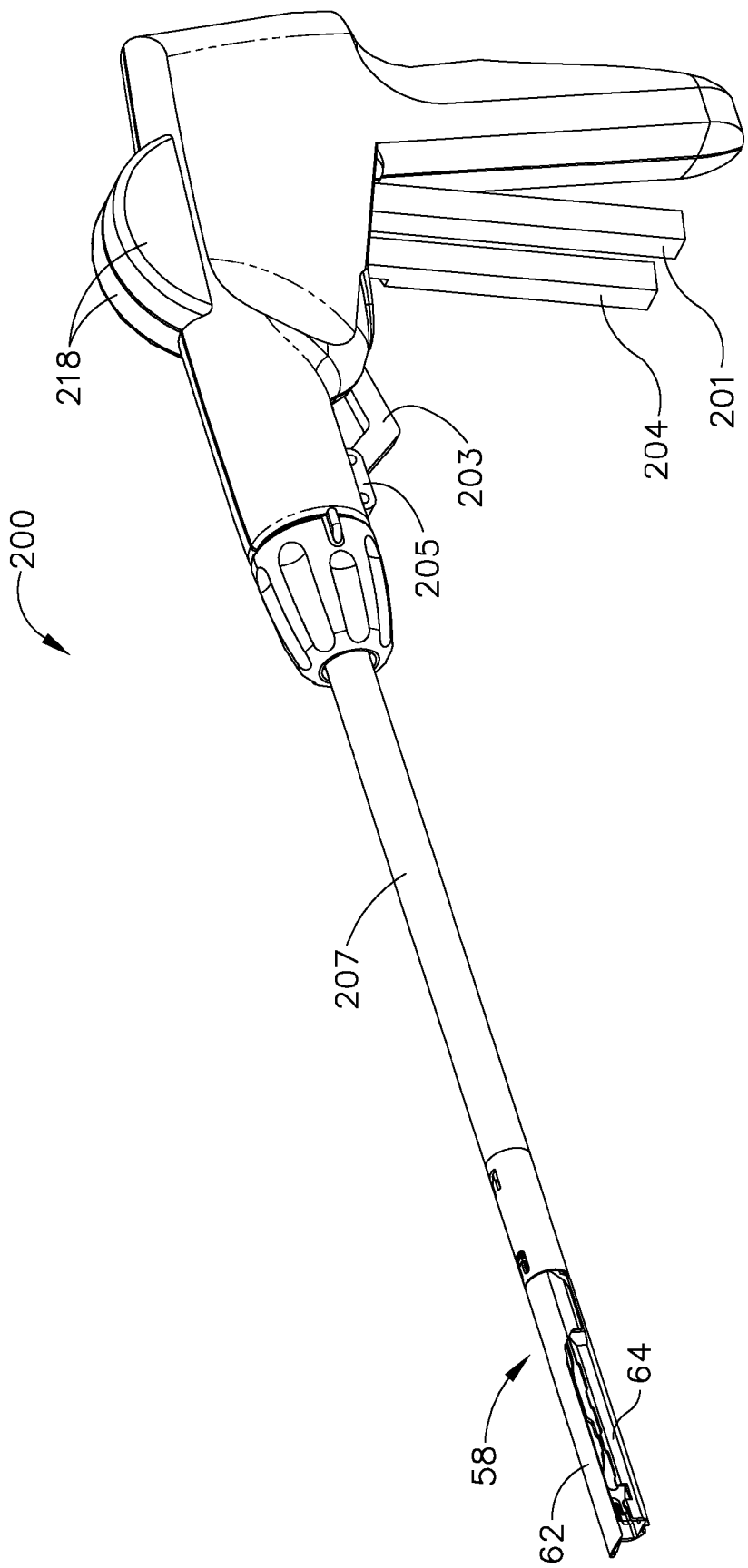
FIG. 23 is a perspective view of a surgical instrument in accordance with an alternative embodiment of the present invention.
Figure 24:
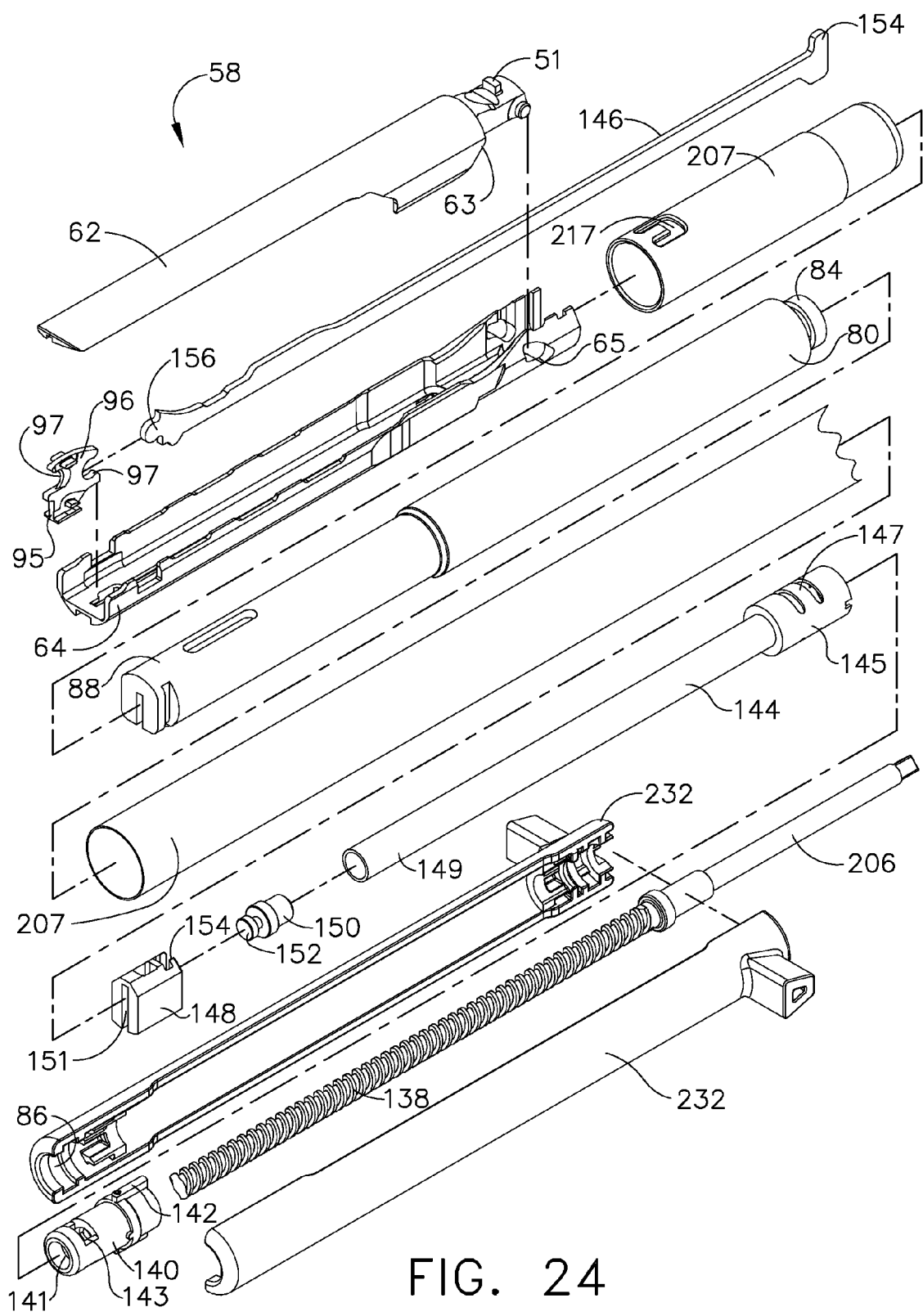
FIG. 24 is an exploded view of the end effector and shaft assembly of the surgical instrument of FIG. 23.

In various embodiments, surgical instruments in accordance with the present invention may include a gearbox for increasing or decreasing the rotational speed of the drive shaft. In at least one embodiment, referring to FIG. 25, surgical instrument 200 can further include gearbox 250 which can be operably positioned intermediate drive shaft 206 and ratchet assemblies 210 and 212. In various embodiments, gearbox 250 can be used to 'gear down' the speed of drive shaft 206 such that shaft 206 turns at a slower speed than if gearbox 250 were not utilized. In alternative embodiments, a gearbox can be used to 'gear up' the speed of drive shaft 206 such that drive shaft 206 turns at a faster speed. In at least one embodiment, gearbox 250 can include at least one set of planetary gears for changing the speed of drive shaft 206. In other various embodiments, a gearbox, such as gearbox 252 illustrated in FIGS. 21 and 22, can include housing 253, input gear 254 mounted to input shaft 256, pinion gears 258, and output gear 260 mounted to output shaft 262. In such embodiments, owing to the different pitch radii of input gear 254 and output gear 260, input shaft 256 and output shaft 262 will rotate at different speeds. To facilitate the rotational movement of gears 254, 258, and 260 within housing 253, gearbox 252 can further include various support plates 264, spacers 266, and pins 268 as illustrated in FIG. 22. In addition to the above, gearbox 252 can also be used to convert the clockwise motion of input shaft 256, for example, into counter-clockwise motion of output shaft 262.

In various embodiments described above, trigger 204 of surgical instrument 200 can be slid between a first position in which it is operatively engaged with first ratchet assembly 210 and a second position in which it is operatively engaged with second ratchet assembly 212. In at least one embodiment, firing drive 202 can be configured such that first pawl 220, for example, is disengaged from first ratchet wheel 222 before second pawl 236 is engaged with second ratchet wheel 234. In such embodiments, trigger 204 may be positioned in an intermediate position where it is not operably engaged with either first ratchet assembly 210 or second ratchet assembly 212. In various embodiments, as a result, firing drive 202 can be in a 'free' state where the actuation of trigger 204 does not result in the rotation of drive shaft 206. In alternative embodiments, firing drive 202 can be configured such that second pawl 236, for example, is engaged with second ratchet wheel 234 before first pawl 220 is operatively disengaged from first ratchet wheel 222. In such embodiments, trigger 204 may be positioned in an intermediate 'locked' state where trigger 204 cannot be actuated, thereby indicating to the surgeon that trigger 204 is not completely engaged with either one of the ratchet assemblies and trigger 204 requires further adjustment.

Figure 33:
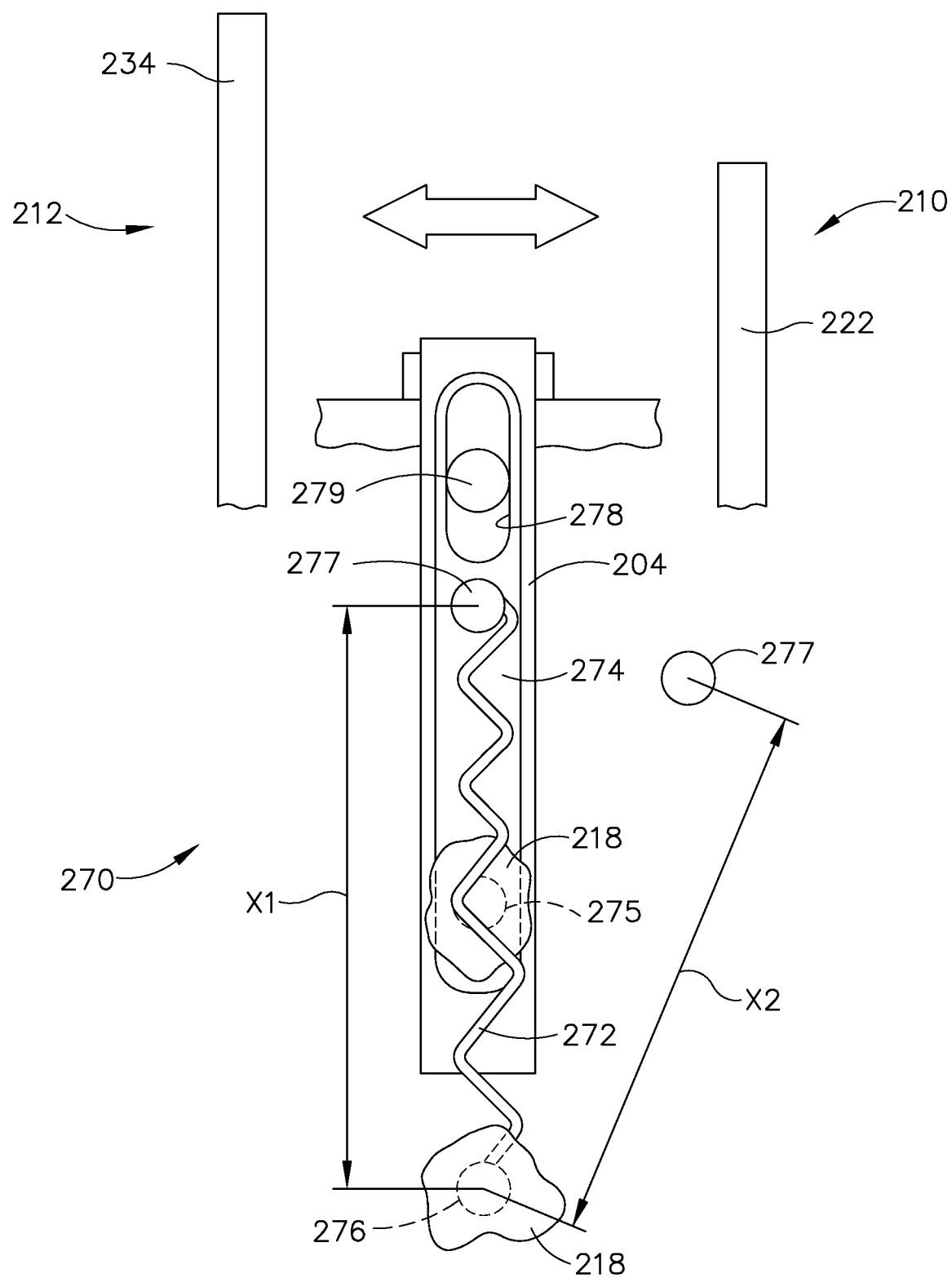
FIG. 33 is a diagram of a bistable compliant mechanism in accordance with an alternative embodiment of the present invention.

In various embodiments, surgical instrument 200 can include a device which biases trigger 204 into engagement with one of first ratchet assembly 210 and second ratchet assembly 212. In at least one embodiment, referring to FIG. 33, surgical instrument 200 can further include bistable compliant mechanism 270 which can bias trigger 204 out of an intermediate position described above and into engagement with either first ratchet assembly 210 and second ratchet assembly 212. In various embodiments, bistable compliant mechanism 270 can include spring 272 and link 274, where spring 272 can apply a biasing force to trigger 204 via link 274 such that the biasing force acts to move trigger 204 out of its intermediate position illustrated in FIG. 33 and into engagement with either first ratchet wheel 222 or second ratchet wheel 234. More particularly, when trigger 204 is positioned in its intermediate position, spring 272 can be stretched to a length X1 and, owing to the resiliency of spring 272, spring 272 can seek to shorten itself to its unstretched length, or at least a length shorter than X1, such as length X2 for example. In order for spring 272 to shorten itself to length X2, spring 272 can rotate link 274 about pin 275 where pin 275 can extend from and pivotably mount link 274 to surgical instrument housing 218. More particularly, as the first end of spring 272 is mounted to pin 276 extending from housing 218 and the second end of spring 272 is mounted to pin 277 extending from link 274, spring 272 can shorten itself by moving pin 277 closer to pin 276 which is most easily accomplished by rotating link 274 about pin 275. As link 274 is rotated about pin 275, the side walls of slot 278 in link 274 can be configured to engage pin 279 extending from trigger 204 and slide trigger 204 into engagement with first ratchet wheel 222 or second ratchet wheel 234. In effect, the intermediate position of trigger 204 illustrated in FIG. 33 represents a dynamically unstable position and the positions of trigger 204 where trigger 204 is engaged with ratchet wheels 222 and 234 represent the dynamically stable positions of the firing drive system.

Figure 31:
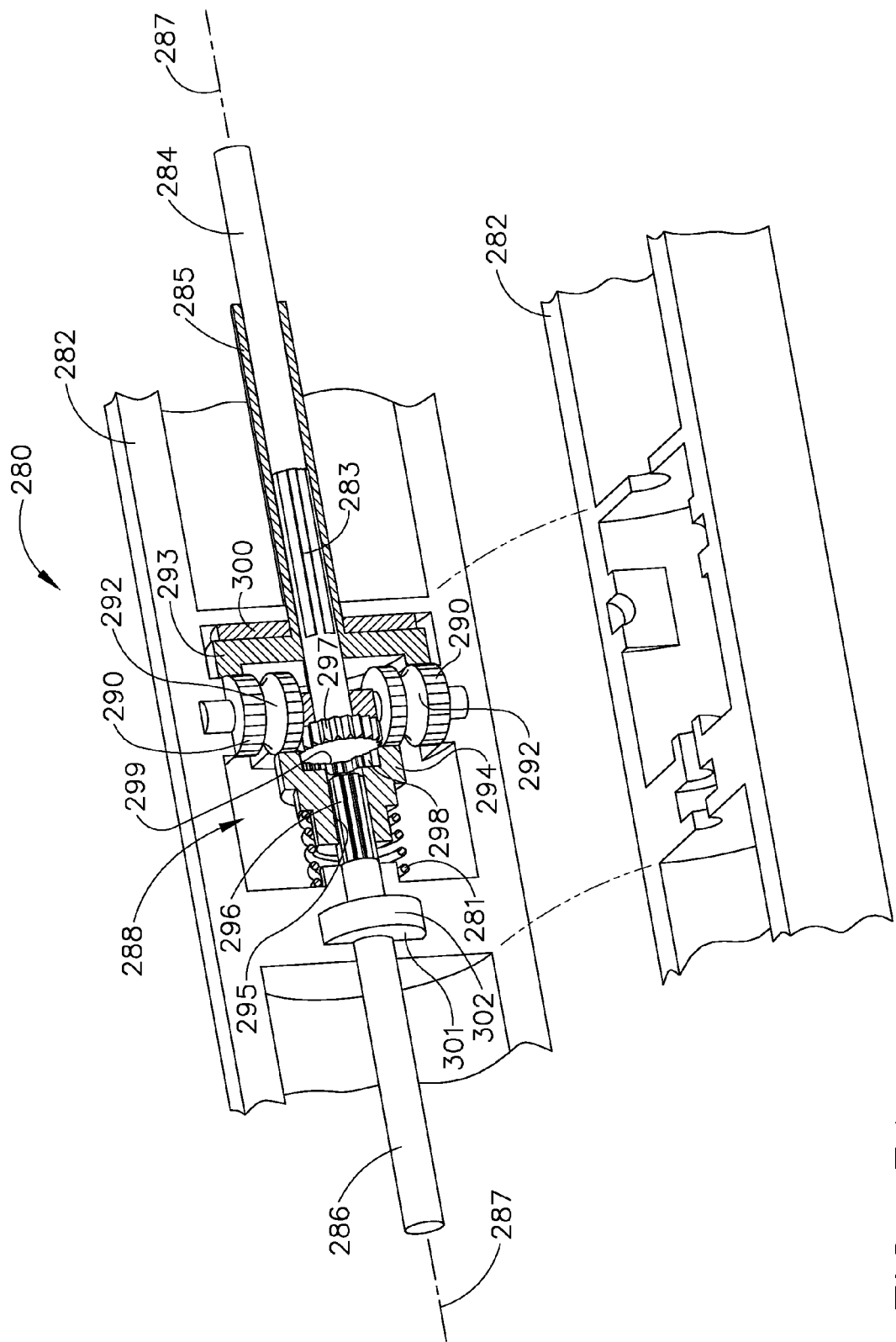
FIG. 31 is a perspective view of a directional switching mechanism in accordance with an alternative embodiment of the present invention with some components disassembled and other components illustrated in cross-section.
Figure 32:
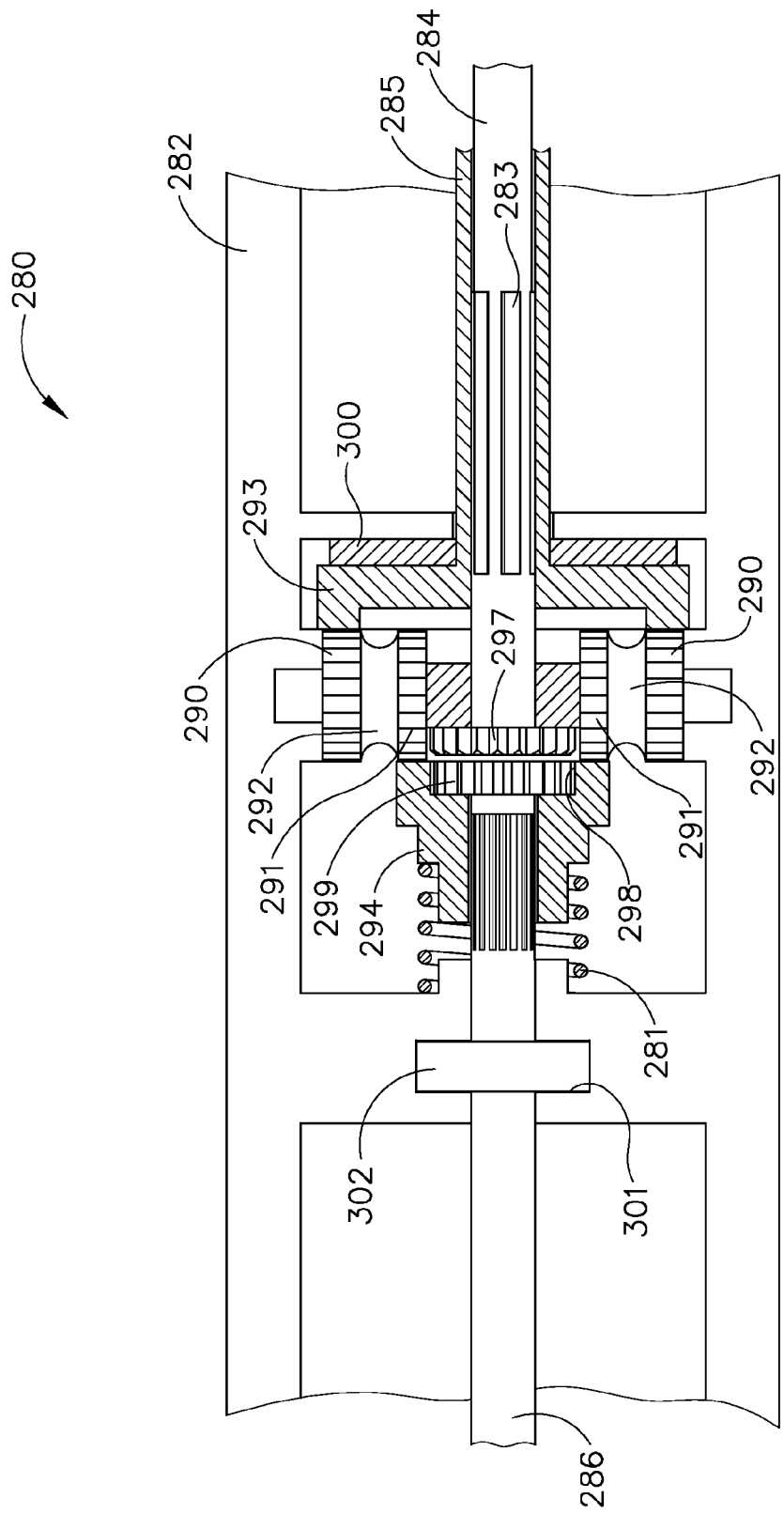
FIG. 32 is a plan view of the directional switching mechanism of FIG. 31 with some components removed and other components illustrated in cross-section.

In various embodiments, as described above, surgical instruments in accordance with the present invention can include devices for rotating a drive shaft in a first direction in which the drive shaft advances a cutting member within an end effector, for example, and a second direction in which the drive shaft retracts the cutting member. In at least one embodiment, referring to FIGS. 31 and 32, a surgical instrument can include transmission 280, for example, which can allow a surgeon to select whether the drive shaft advances or retracts the cutting member. In various embodiments, transmission 280 can include housing 282, internal input shaft 284, external input shaft 285, output drive shaft 286, and switching mechanism 288, where switching mechanism 288 can be configured to selectively engage internal input shaft 284 and external input shaft 285 with output shaft 286. Although not illustrated, the surgical instrument can further include a trigger, for example, which is operatively engaged with external drive shaft 285 in order to rotate drive shaft 285 about axis 287 in a clockwise direction, for example. In at least one embodiment, transmission 280 can include pinion gears 292 rotatably mounted within housing 282, input gear 293 fixedly mounted to external input shaft 285, and output gear 294 mounted to output drive shaft 286, where input gear 293 can be operably engaged with outer gear teeth 290 of pinion gears 292 such that the rotation of external shaft 285 is transmitted to pinion gears 292.

In a first configuration of transmission 280, output gear 294 can be operatively engaged with inner gear teeth 291 of pinion gears 292 such that the rotation of pinion gears 292 is transmitted to output drive shaft 286. More particularly, output gear 294 can be operably engaged with output drive shaft 286 via splined end 296 such that output gear 294 drives output drive shaft 286 about axis 287. In this first configuration, a clockwise rotation of external input shaft 285, for example, can be converted into a counter-clockwise motion of output drive shaft 286. In a second configuration of transmission 280, output gear 294 can be disengaged from pinion gears 292 such that the rotation of external input shaft 285 is not transmitted to output drive shaft 286 via pinion gears 292. In order to disengage output gear 294 from pinion gears 292, internal drive shaft 284 can be slid relative to external drive shaft 285 such that input gear 297 contacts recess 298 in output gear 294 and pushes output gear 294 away from pinion gears 292. In at least one embodiment, recess 298 can include teeth 299 which can be operatively engaged with input gear 297 of internal input shaft 284 such that the rotation of internal input shaft 284 is transmitted to output drive shaft 286. In this second configuration of transmission 280, a clockwise rotation of internal input shaft 284 can be directly transmitted to output drive shaft 286 such that output shaft 286 rotates in a clockwise direction as well. In order to reengage output gear 294 with pinion gears 292, internal input gear 284 can be disengaged from output gear 294 to allow spring 281 to slide output gear 294 along splined end 296.

In the embodiments described above, a surgeon can selectively move internal input shaft 284 relative to external input shaft 285 to place transmission 280 in either a forward or reversing configuration. In order to move input shaft 284, in various embodiments, the surgical instrument can further include an actuator or trigger configured to translate internal input shaft 284. In at least one embodiment, the surgical instrument can include a first actuator or trigger for rotating external input shaft 285 and a second actuator or trigger for translating internal shaft 284 relative to external shaft 285. In such embodiments, internal input shaft 284 can include splines 283 which can be slidably engaged with external input shaft 285 such that the rotation of external shaft 285 is transmitted to internal shaft 284 yet sliding motion is permitted therebetween. In at least one embodiment, transmission 280 can further include bearing 300 which can rotatably support input gear 293 and, when compressed between input gear 293 and housing 282, provide a biasing force to keep input gear 293 operably engaged with pinion gears 292. In various embodiments, output shaft 286 can include member 302 extending therefrom which can be configured to be received within recess 301 of housing 282 in order to reduce, or even eliminate, relative movement between output shaft 286 and housing 282. In at least one embodiment, although not illustrated, transmission 280 may only have one pinion gear 292 and still operate in the manner described above.

In various embodiments, transmission 280 can also be configured to advance cutting member 96, for example, at a different rate than which it is retracted. In at least one embodiment, referring to FIGS. 31 and 32, the operative engagement between internal input shaft 284 and output shaft 286 can be used to advance cutting member 96 and, owing to the direct engagement between input gear 297 and output gear 294, internal input shaft 284 and output shaft 286 can rotate in a 1:1 ratio, i.e., for every rotation of internal input shaft 284, output shaft 286 is rotated once. In various embodiments, the operative engagement between external input shaft 285 and output shaft 286 can be used to retract cutting member 96 and, owing to the different pitch radii of input gear 293 and output gear 294 and their operative engagement with pinions 292, external input shaft 285 and output shaft 286 can rotate in a ratio different than 1:1. In the illustrated embodiment, output shaft 286 can rotate at a faster speed than external input shaft 285 when they are mated via pinions 292. In various embodiments, as a result, cutting member 96 can be translated at a faster rate when external input shaft 285 is operably engaged with output shaft 286 than when internal input shaft 284 is operably engaged with output shaft 286.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical instrument comprising:
    an end effector having a selectively reciprocatable implement movably supported therein, said implement being selectively advanceable in a distal direction upon application of a rotary actuation motion thereto and retractable in a proximal direction upon application of a rotary retraction motion thereto;
    an elongate shaft assembly coupled to said end effector and including a rotatable drive shaft operably engaged with said reciprocatable implement for transmitting said rotary actuation motion and rotary retraction motion thereto, said rotatable drive shaft including a first gear and a second gear; and
    a firing drive comprising:
        a first rotary drive member including a plurality of first gear teeth selectively interfacing with said first gear to apply said rotary actuation motion thereto when activated; and
        a second rotary drive member including a plurality of second gear teeth operably engaged with said second gear to apply said rotary retraction motion thereto when said first rotary drive member is deactivated and said second rotary drive member is activated.

2. The surgical instrument of claim 1 wherein said end effector comprises:
    an elongate channel configured to operably support a staple cartridge therein; and
    an anvil movably coupled to said elongate channel and wherein said reciprocatable implement comprises a cutting member operably supported within said elongate channel.

3. The surgical instrument of claim 2, further comprising a closure drive configured to selectively generate a closing motion and an opening motion, wherein said anvil is operably engaged with said closure drive and is movably responsive to said opening motion and said closing motion.

4. The surgical instrument of claim 1, wherein said drive shaft defines an axis, wherein said first rotary drive member is positioned on a first side of said axis and is configured to rotate said drive shaft about said axis in a first direction, and wherein said second rotary drive member is positioned on a second side of said axis to rotate said drive shaft about said axis in a second direction, wherein said second direction is opposite said first direction.

5. The surgical instrument of claim 1 wherein said end effector comprises:
    an elongate channel configured to operably support a staple cartridge therein; and
    an anvil movably coupled to said elongate channel and wherein said reciprocatable implement comprises a cutting member operably supported within said elongate channel.

6. The surgical instrument of claim 5 further comprising a closure drive configured to selectively generate a closing motion and an opening motion, wherein said anvil is operably engaged with said closure drive and is movably responsive to said opening motion and said closing motion.

7. A surgical instrument, comprising:
    an end effector having a selectively reciprocatable implement movably supported therein and being selectively advanceable in a distal direction upon application of a rotary actuation motion thereto and retractable in a proximal direction upon application of a rotary retraction motion thereto;
    an elongate shaft assembly coupled to said end effector and configured to transmit said rotary actuation motion and rotary retraction motion to said reciprocatable implement; and
    a firing drive interfacing with said elongate shaft to apply said rotary actuation and rotary retraction motions thereto, said firing drive comprising:
        a first ratchet assembly, comprising:
            a first ratchet wheel having a plurality of ratchet teeth; and
            a first pawl pivotably connected to an actuator device, wherein said first pawl is selectively engageable with said ratchet teeth of said first ratchet wheel to apply said rotary actuation motion to said elongate shaft; and
        a second ratchet assembly, comprising:

a second ratchet wheel having a plurality of ratchet teeth; and
a second pawl pivotably connected to said actuator device, wherein said second pawl is selectively engageable with said ratchet teeth of said second ratchet wheel to apply said rotary retraction motion to said elongate shaft.

8. The surgical instrument of claim 7, further comprising:
a first spring configured to effect ratcheting engagement between said first pawl and said ratchet teeth of said first ratchet wheel; and
a second spring configured to effect ratcheting engagement between said second pawl and said ratchet teeth of said second ratchet wheel.

9. The surgical instrument of claim 8, wherein said drive shaft defines an axis, wherein said first ratchet wheel is positioned on a first side of said axis and is configured to rotate said drive shaft about said axis in a first direction, and wherein said second ratchet wheel is positioned on a second side of said axis to rotate said drive shaft about said axis in a second direction, wherein said second direction is opposite said first direction.

10. The surgical instrument of claim 7, wherein said first ratchet wheel further includes a plurality of first gear teeth positioned about a first diameter, wherein said second ratchet wheel includes a plurality of second gear teeth positioned about a second diameter, wherein said second diameter is greater than said first diameter, wherein said elongate shaft assembly includes a rotatable drive shaft operably engaged with said cutting member, and wherein said drive shaft includes a first gear operably engaged with said first gear teeth and a second gear operably engaged with said second gear teeth.

11. The surgical instrument of claim 7, further comprising:
a frame;
a slidable member mounted to said first pawl and said second pawl; and
a spring operably engaged with said slidable member and said frame, and wherein said spring is configured to motivate said slidable member such that either said first pawl is engaged with said first ratchet wheel or said second pawl is engaged with said second ratchet wheel.

12. The surgical instrument of claim 7, wherein, when said first pawl is engaged with said first ratchet wheel, said second pawl is not engaged with said second ratchet wheel, and wherein, when said second pawl is engaged with said second ratchet wheel, said first pawl is not engaged with said first ratchet wheel.

13. The surgical instrument of claim 7, wherein said first pawl can be engaged with said first ratchet wheel at the same time as said second pawl is engaged with said second ratchet wheel such that said firing drive is prevented from generating said rotary firing motion and said rotary retraction motion.

14. A surgical instrument, comprising:
an end effector having a selectively reciprocatable implement member movably supported therein and being selectively advanceable in a distal direction upon application of a rotary actuation motion thereto and is retractable in a proximal direction upon application of a rotary retraction motion thereto;
an elongate shaft assembly comprising:
an output shaft coupled to said end effector and configured to transmit said rotary actuation motion and rotary retraction motion to said reciprocatable implement;
a first input shaft; and
a second input shaft movable relative to said first input shaft and wherein said surgical instrument further comprises:
a transmission configurable in a first configuration for facilitating rotation of said output shaft about an axis in a first direction and a second configuration for rotating said output shaft about said axis in a direction opposite said first direction, said transmission comprising a switching mechanism communicating with said first and second input shafts such that when said switching mechanism is in a first position, rotation of said first input shaft is transferred to said output shaft and when said switching mechanism is in a second position, rotation of said second input shaft is transferred to said output shaft.

15. The surgical instrument of claim 14 wherein said end effector comprises:
an elongate channel configured to operably support a staple cartridge therein; and
an anvil movably coupled to said elongate channel and wherein said reciprocatable implement comprises a cutting member operably supported within said elongate channel.

16. The surgical instrument of claim 15, further comprising a closure drive configured to selectively generate a closing motion and an opening motion, wherein said anvil is operably engaged with said closure drive and is movably responsive to said opening motion and said closing motion.

17. The surgical instrument of claim 14 wherein said transmission further comprises pinion gears in meshing engagement with said first input shaft.

18. The surgical instrument of claim 17 wherein said switching mechanism further comprises an output gear operably interfacing with said output shaft and configured for selective meshing engagement with said pinion gears.

19. The surgical instrument of claim 18 wherein said transmission further comprises an input gear operably coupled to said second input shaft and wherein said second input shaft is axially movable relative to said first input shaft such that when said second input shaft is in said first position, said pinion gears are in meshing engagement with said output gear and when said second input shaft is in said second position, said pinion gears are disengaged from said output gear and said input gear is in meshing engagement with said output gear such that rotation of said second input shaft relative to said first input shaft is transferred to said output gear.

* * * * *